US010190160B2

(12) United States Patent
Szallasi et al.

(10) Patent No.: US 10,190,160 B2
(45) Date of Patent: *Jan. 29, 2019

(54) METHODS FOR PREDICTING ANTI-CANCER RESPONSE

(71) Applicants: Children's Medical Center Corporation, Boston, MA (US); The Technical University of Denmark, Lyngby (DK); Dana-Farber Cancer Institute, Inc., Boston, MA (US); The Brigham and Women's Hospital, Inc., Boston, MA (US)

(72) Inventors: Zoltan Szallasi, Boston, MA (US); Nicolai Juul Birkbak, København Ø (DK); Aron Eklund, København Ø (DK); Daniel Silver, Wayland, MA (US); Zhigang Wang, Chestnut Hill, MA (US); Andrea Richardson, Chestnut Hill, MA (US)

(73) Assignees: Children's Medical Center Corporation, Boston, MA (US); The Technical University of Denmark, Lyngby (DK); Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/466,208

(22) Filed: Aug. 22, 2014

(65) Prior Publication Data
US 2015/0038340 A1 Feb. 5, 2015

Related U.S. Application Data

(63) Continuation of application No. PCT/US2013/027295, filed on Feb. 22, 2013.

(60) Provisional application No. 61/602,460, filed on Feb. 23, 2012, provisional application No. 61/604,810, filed on Feb. 29, 2012.

(51) Int. Cl.
*C12Q 1/6886* (2018.01)
*C12P 19/34* (2006.01)
*A61K 38/00* (2006.01)
*C07D 487/00* (2006.01)
*C12Q 1/6874* (2018.01)

(52) U.S. Cl.
CPC ........ *C12Q 1/6874* (2013.01); *C12Q 1/6886* (2013.01); *C12Q 2600/106* (2013.01); *C12Q 2600/154* (2013.01); *C12Q 2600/156* (2013.01); *C12Q 2600/158* (2013.01); *G01N 2800/52* (2013.01)

(58) Field of Classification Search
CPC ............ C12Q 1/6886; C12Q 2600/156; C12Q 2600/154; G01N 2800/52
See application file for complete search history.

(56) References Cited

U.S. PATENT DOCUMENTS

| | | | |
|---|---|---|---|
| 3,590,028 A | 6/1971 | Arcamone et al. |
| 3,892,790 A | 7/1975 | Tobe et al. |
| 3,904,663 A | 9/1975 | Tobe et al. |
| 4,138,480 A | 2/1979 | Gosalvez et al. |
| 4,946,954 A | 8/1990 | Talebian et al. |
| 4,950,738 A | 8/1990 | King et al. |
| 4,996,337 A | 2/1991 | Bitha et al. |
| 5,091,521 A | 2/1992 | Kolar et al. |
| 5,177,075 A | 1/1993 | Suto et al. |
| 5,295,944 A | 3/1994 | Teicher et al. |
| 5,434,256 A | 7/1995 | Khokhar et al. |
| 5,445,934 A | 8/1995 | Fodor et al. |
| 5,510,270 A | 4/1996 | Fodor et al. |
| 5,527,905 A | 6/1996 | Sugimura et al. |
| 5,539,083 A | 7/1996 | Cook et al. |
| 5,556,752 A | 9/1996 | Lockhart et al. |
| 5,578,832 A | 11/1996 | Trulson et al. |
| 5,633,016 A | 5/1997 | Johnson et al. |
| 5,633,243 A | 5/1997 | Sugimura et al. |
| 5,744,305 A | 4/1998 | Fodor et al. |
| RE36,397 E | 11/1999 | Zhang et al. |
| 6,040,138 A | 3/2000 | Lockhart et al. |
| 6,087,340 A | 7/2000 | Gatti et al. |
| 6,210,891 B1 | 4/2001 | Nyren et al. |
| 6,214,821 B1 | 4/2001 | Daoud |
| 6,258,568 B1 | 7/2001 | Nyren et al. |
| 6,274,320 B1 | 8/2001 | Rothberg et al. |
| 6,403,563 B1 | 6/2002 | Geroni et al. |
| 6,455,258 B2 | 9/2002 | Bastian et al. |

(Continued)

FOREIGN PATENT DOCUMENTS

EP 0430402 6/1991
KR 100925337 B1 11/2009
(Continued)

OTHER PUBLICATIONS

Juul, N. et al. Annals of Oncology, vol. 21, suppl May 4, 2010, Abstract Book of the IMPAKT 2010 Breast Cancer Conference, Brussels, Belgium, May 6-8, 2010, Abstract 33P.*
(Continued)

*Primary Examiner* — Stephen T Kapushoc
(74) *Attorney, Agent, or Firm* — David S. Resnick; Mark J. FitzGerald; Nixon Peabody LLP

(57) ABSTRACT

The present invention is based, in part, on the identification of novel methods for defining predictive biomarkers of response to anti-cancer drugs.

7 Claims, 27 Drawing Sheets

(56) References Cited

U.S. PATENT DOCUMENTS

| | | | |
|---|---|---|---|
| 6,465,177 | B1 | 10/2002 | Hoon |
| 6,534,293 | B1 | 3/2003 | Barany et al. |
| 7,351,701 | B2 | 4/2008 | Helleday et al. |
| 7,485,707 | B2 | 2/2009 | Matvienko et al. |
| 7,732,491 | B2 | 6/2010 | Sherman et al. |
| 7,754,684 | B2 | 7/2010 | Stewart et al. |
| 7,759,488 | B2 | 7/2010 | Xiao et al. |
| 7,759,510 | B2 | 7/2010 | Kay et al. |
| 7,858,331 | B2 | 12/2010 | D'Andrea et al. |
| 7,860,840 | B2 | 12/2010 | Johnson et al. |
| 7,868,040 | B2 | 1/2011 | Wilson et al. |
| 7,915,280 | B2 | 3/2011 | Ferraris et al. |
| 9,279,156 | B2 | 3/2016 | Gutin et al. |
| 2003/0049613 | A1 | 3/2003 | Perucho et al. |
| 2005/0112604 | A1 | 5/2005 | Fujimoto et al. |
| 2006/0088870 | A1 | 4/2006 | Finkelstein et al. |
| 2007/0004621 | A1 | 1/2007 | Shridhar et al. |
| 2007/0070349 | A1 | 3/2007 | Harris et al. |
| 2008/0108057 | A1 | 5/2008 | Griffith et al. |
| 2009/0081237 | A1 | 3/2009 | D'Andrea et al. |
| 2009/0246789 | A1 | 10/2009 | Buckhaults et al. |
| 2010/0145894 | A1 | 6/2010 | Semizarov et al. |
| 2010/0159466 | A1 | 6/2010 | Eng et al. |
| 2012/0015050 | A1 | 1/2012 | Abkevich et al. |
| 2013/0281312 | A1* | 10/2013 | Richardson .......... C12Q 1/6886 506/9 |
| 2015/0080260 | A1 | 3/2015 | Abkevich et al. |

FOREIGN PATENT DOCUMENTS

| | | |
|---|---|---|
| WO | 9841531 | 9/1998 |
| WO | 99054498 | 10/1999 |
| WO | 9520952 | 11/1999 |
| WO | 0024933 | 4/2000 |
| WO | 2003074723 | 9/2003 |
| WO | 2004042032 A2 | 5/2004 |
| WO | 2004/075833 A2 | 9/2004 |
| WO | 2006098978 A1 | 9/2006 |
| WO | 2006/110855 A2 | 10/2006 |
| WO | 2006/116341 A1 | 11/2006 |
| WO | 2006128195 | 11/2006 |
| WO | 2007035893 | 3/2007 |
| WO | 2009033178 | 3/2009 |
| WO | 2009/073869 A1 | 6/2009 |
| WO | 2009148528 | 12/2009 |
| WO | 2010051318 | 5/2010 |
| WO | 2011048495 | 4/2011 |
| WO | 2011106541 | 12/2011 |
| WO | 2011160063 | 12/2011 |
| WO | 2012019000 | 2/2012 |
| WO | 2012027224 | 3/2012 |
| WO | 2012/092426 A1 | 7/2012 |
| WO | 2013/096843 A1 | 6/2013 |
| WO | 2013/130347 A1 | 9/2013 |
| WO | 2013182645 | 12/2013 |
| WO | 2014/165785 A2 | 10/2014 |
| WO | 2015/086473 A1 | 6/2015 |
| WO | 2015/108986 A1 | 7/2015 |

OTHER PUBLICATIONS

Juul, N. et al. Cancer Research, vol. 69 Issue 24 Supplement, pp. 111, "A Genomic-Profile Derived Summary Measure of Chromosomal Breakpoints Predicts Response to Treatment with the DNA-Damaging Agent Cisplatin". four printed pages from cancerres.aacrjournals.org/content/69/24_Supplement/111.*

Birkbak et al, Cancer Discovery, vol. 2, No. 4, pp. 366-375, 2012.

Chang et al, J. of the National Cancer Center Institute, vol. 94, No. 22, pp. 1697-1903, 2002.

Matsumoto et al, British J. of Cancer, vol. 91, No. 6, p. 1025-1031, 2004.

Stefansson et al, Breast Cancer Research, vol. 11, No. 4, pp. 1-14, 2009.

Arlt et al., Molecular and Cellular Biology, 24(5):6701-6709 (2004). "BRCA1 is required for common-fragile-site stability via its G2M checkpoint function."

Bamford et al., British Journal of Cancer 91:355-358 (2004). "The COSMIC (Catalogue of Somatic Mutations in Cancer) database and website."

Bell et al., Nature 474:609-615 (2011). "Intergrated genomic analyses of ovarian carcinoma."

Bengtsson et al., Bioinformatics 25(17):2149-2156 (2009). "A single-array preprocessing methos for estimating full-resolution raw copy numbers from all affymetrix genotyping arrays includig genomeWideSNP 5 & 6."

Bengtsson et al., BMC Bioinformatics 11:245-262 (2010). "TumorBoost: Normalization of allele-specific tumor copy numbers from a singe pair of tumor-normal genotyping microarrays."

Bouwman et al., Nature Structural and Molecular Biology 17(6):688-696 (2010). "53BP1 loss rescues BRCA1 deficiency and is associated with triple-negative and BRCA-mutated breast cancers."

Byrski et al., Breast Cancer Res Treat. 115(2):359-63. (2009). Response to neoadjuvant therapy with cisplatin in BRCA1-positive breast cancer patients.

Bunting et al., Cell. 141(2):243-54 (2010). "53BP1 inhibits homologous recombination in Brca1-deficient cells by blocking resection of DNA breaks."

Burger et al. Drug Resistance Updates 14:22-34 (2011). 'Drug transporters of platinum-based anticancer agents and their clinical significance.'

Cass et al., Cancer. 97(9):2187-95 (2003). "Improved survival in women with BRCA-associated ovarian carcinoma."

Cha et al., Science. ;297(5581):602-6 (2002). "ATR homolog Mec1 promotes fork progression, thus averting breaks in replication slow zones."

Hasting et al., PLOS Genetics 5(1):e1000327 (2009). "A microhomology-mediated break-induced replication model for the origin of human copy number variation."

Hastings et al., Nat Rev. Genetic 10(8):551-564 (2009). "Mechanisms of change in gene copy number."

Heiser et al., Proc Natl Acad Sci U S A. 109(8):2724-9 (2012). "Subtype and pathway specific responses to anticancer compounds in breast cancer."

Iafrate et al., Nat Genet. 36(9):949-51. (2004). "Detection of large-scale variation in the human genome."

Kalb et al., Genome Dyn. 1:218-42. (2006). "Fanconi anemia: causes and consequences of genetic instability."

Kolomietz et al., Genes Chromosomes Cancer. 35(2):97-112 (2002). "The role of Alu repeat clusters as mediators of recurrent chromosomal aberrations in tumors."

Lakhani et al., Clin Cancer Res. 11(14):5175-80 (2005). "Prediction of BRCA1 status in patients with breast cancer using estrogen receptor and basal phenotype."

Li et al.,Nature Medicine 16(2):214-219 (2010). Amplication of LAPTM4B and YWHAZ contributes to chemotherapy resistance and recurrence of breast cancer.

Li et al., BMC Bioinformatics 12:474 (2011). "Jetset: selecting the optimal microarray probe set to represent a gene."

Luo et al., Nat Genet. 26(4):424-9 (2000). "Cancer predisposition caused by elevated mitotic recombination in Bloom mice."

McVean et al., Philos Trans R Soc Lond B Biol Sci. 365(1544):1213-8 (2010). "What drives recombination hotspots to repeat DNA in humans?"

Ogston et al., Breast. 2(5):320-7 (2003). "A new histological grading system to assess response of breast cancers to primary chemotherapy: prognostic significance and survival."

Puliti et al., Mutat Res. 686(1-2):74-83 (2010). "Low-copy repeats on chromosome 22q11.2 show replication timing switches, DNA flexibility peaks and stress inducible asynchrony, sharing instability features with fragile sites."

Richard et al., Microbiol Mol Biol Rev. 72(4):686-727 (2008). "Comparative genomics and molecular dynamics of DNA repeats in eukaryotes."

Richardson et al., Cancer Cell 9:121-132 (2006). "X chromosomal abnormalities in basal-like human breast cancer."

(56) References Cited

OTHER PUBLICATIONS

Ryan et al., 2009 ASCO Annual Meeting, http://meetinglibrary.asco.org/content/34135-65, (2009). Neoadjuvant cisplatin and bevacizumab in triple negative breast cancer (TNBC): Safety and efficacy.

Samouelian et al., Cancer Chemother Pharmacol. 54(6):497-504 (2004). "Chemosensitivity and radiosensitivity profiles of four new human epithelial ovarian cancer cell lines exhibiting genetic alterations in BRCA2, TGFbeta-RII, KRAS2, TP53 and/or CDNK2A."

Schwartz et al., Genes Development 19:2715-2726 (2005). "Homologous recombination and nonhomologous end-joining repair pathways regulate fragile site stability."

Sebat et al., Science. 305(5683):525-8 (2004). "Large-scale copy number polymorphism in the human genome."

Silver et al., Cell 128(5):991-1002 (2007). "Further evidence for BRCA1 communication with the inactive X chromosome."

Sorlie et al., PNAS 100(14):8418-8423 (2003). "Repeated observation of breast tumor subtypes in independent gene expression data set."

Stankiewicz et al., Am J Hum Genet. 72(5):1101-16 (2003). "Genome architecture catalyzes nonrecurrent chromosomal rearrangements."

Swisher et al. Cancer Res. 68(8):2581-6 (2008). "Secondary BRCA1 mutations in BRCA1-mutated ovarian carcinomas with platinum resistance."

Tassone et al., Br J Cancer. 88(8):1285-91 (2003). "BRCA1 expression modulates chemosensitivity of BRCA1-defective HCC1937 human breast cancer cells."

Turner et al., Oncogene 26:2126-2132 (2007). "BRCA1 dysfuntion in sporadic basal-like breast cancer."

Van Loo et al.,PNAS 107(39):16910-16915 (2010). "Allele-specific copy number analysis of tumors."

Vrieling et al., Nature Genetics 28:101-102 (2001). "Mitotic maneuvers in the light."

Wang et al., Cancer Research 64:64-71 (2004). "Loss of heterozygosity and it's correlation with expression profiles in subclasses of invasive breast cancers."

Wang et al., Genome Biology 8:R246 (2007). "Analysis of molecular inversion probe performance for allele copy number determination".

Xu et al., Molecular Cell 3:389-395 (1999). "Centrosome amplification and a defective G2-M cell cycle checkpoint induce genetic instability in BRCA1 Exon 11 Isoform-deficient cells."

Yang et al. Cancer Research 61:348-354 (2001). "Reconstitution of caspase 3 sensitizes MCF-7 Breast Cancer to Doxoubicin- and Etoposide-induced apoptsis."

International Search Report, for application PCT/EP2013/061707, dated Jul. 29, 2013.

International Search Report, for application PCT/US2011/040953, dated Feb. 27, 2012.

International Search Report, for application PCT/US2011/048427, dated Nov. 7, 2011.

International Search Report, for application PCT/US2012/042668, dated Feb. 1, 2013.

International Search Report, for application PCT/US2012/071380, dated Apr. 12, 2013.

International Search Report, for application PCT/US2013/027295, dated Jun. 10, 2013.

Janne et al. "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726, XP055085726, ISSN: 0950-9232, DOI: 10.1038/sj.onc.1207329 *abstract*.

Joosse et al. "Prediction of BRCA-1-association in hereditary non-BRCA1/2 breast carcinomas with array-CGH", Breast Cancer Research and Treatment, Kluwer Academic Publishers, BO, vol. 116, No. 3, Aug. 14, 2008 (Aug. 14, 2008), pp. 479-489, XP019727887, ISSN: 1573-7217, abstract.

Keranguevan, F. et al. Cancer Research 57, 5469-5475 (1997).

Ko et al., "Frequent loss of heterozygosity on multiple chromosomes in Chinese esophageal squamous cell carcinomas" Cancer Letters, vol. 170, No. 2, pp. 131-138 (2001) See whole document.

Kujawski et al. "Genomic complexity identifies patients with agressive chronic lymphocytic lukemia", Blood, vol. 112, No. 5, Sep. 1, 2008 (Sep. 1, 2008), pp. 1993-2003, XP055085975, iSSN: 0006-4971, DOI: 10.1182/blood-2007-07-099432 *the whole document*.

Lemeta et al., "Loss of Heterozygosity at 6q is Frequent and Concurrent with 3p Loss in Sporadic and Familial Capillary Hemangioblastomas," J. Neuropathol. Exp. Neurol., Oct. 2004, vol. 63, No. 10, pp. 1072-1079.

Leunen et al. "Recurrent Copy number alterations in BRCA1-mutated ovarian tumors alter biological pathways", Human Mutation, vol. 30, n. 12, Dec. 1, 2009 (Dec. 1, 2009), pp. 1693-1702, XP055040581, ISSN: 1059-7794, DOI: 10.1002/humu.21135 *abstract* *paragraph bridging p. 1694-1965; figures 2B, 3, 4*.

Loveday et al.; Germline mutations in RAD51D confer susceptibility to ovarian cancer; Nat Genet; 2011; 43(9):879-882.

Marsit et al.; Inactivation of the Fanconi anemia/BRCA pathway in lung and oral cancers: implications for treatment and survival; Oncogene; 2004; 23(4):1000-1004.

Meadows et al. "Genome-wide analysis of loss of heterozygosity and copy number amplification in uterine leiomyomas using the 100K single nucleotide polymorphism array", Experimental and Molecular Pathology, vol. 91, No. 1, Apr. 8, 2011 (Apr. 8, 2011), 434-439, XP028239924, ISSN: 0014-4800, DOI: pages.10.1016/J.YEXMP.2011.03.007 [retrieved on Apr. 8, 2011] *abstract, conclutions; p. 438 col. 2 par. 3*.

Medri, L. et al. modern Pathology 2003;16(11):1067-1075.

Meindl et al.; Germline mutations in breast and ovarian cnacer pedigrees establish RAD51C as a human cancer susceptibility gene; Nat Genet; 2010; 42(5):410-414.

Mendes-Pereira et al.; Synthetic lethal targeting of PTEN mutant cells with PARP inhibitors; EMBO Mol Med; 2009;1(6-7): 315-322.

Murayama-Hosokawa, S. et al., "Genome-wide single-nucleotide polymorphism arrays in endometrial carcinomas associate extensive chromosomal instability with poor prognosis and unveil frequent chromosomal imbalances involved in the PI3-kinase pathway," Oncogene, Apr. 1, 2010, vol. 29, No. 13, pp. 1897-908.

Nannya et al. "A Robust Algorithm for Copy Number Detection Using High-Density Oligonucleotide Single Nucleotide Polymorphism Genotyping Arrays", Cancer Research, American Association for Cancer Research, US, vol. 65, No. 14, Jul. 14, 2005 (Jul. 14, 2005), pp. 6071-6079, XP008155967, ISSN: 0008-5472, DOI:10.1158/0008-5472.CAN-05-0465 Retrieved from the internet: URL: http://cancerres.aacrjournals.org [retrieved on Jul. 15, 2005] *the whole document*.

Narayan et al.; Frequent promoter of methylation of CDH1,DAPK,RARB, and HIC1 genes in carcinoma of cervix uteri: its relationship to clinical outcome; Mol Cancer; 2003;2:24, 12 pages.

Norquist et al.; Secondary somatic mutations restoring BRCA1/2 predict chemotherapy resistance in hereditary ovarian carcinomas; J Clin Oncol;2011; 29(22): 3008-3015.

Osborne et al., A genome-wide map showing common regions of loss of heterozygosity/allelic imbalance in breast cancer, Cancer Research, vol. 60, No. 14, pp. 3706-3712 (2000) See whole document.

O'Shaugnessy et al., "Iniparib plus chemotherapy in metastatic triple-negative breast cancer," N Engl J Med. 2011; 364(3):205-214.

Penning et al., "Discovery and SAR of 2-(1-propylpiperidin-4-yl)-1H-benzimidazole-4-carboxamide: A potent inhibitor of poly(ADP-ribose) polymerase (PARP) for the treatment of cancer", Bioorganic & Medicinal Chemistry, Pergamon, GB, vol. 16, No. 14, Jul. 15, 2008 (Jul. 15, 2008), pp. 6965-6975, XP022941564, ISSN: 0968-0896, DOI 10.1016/J.BMC.2008.05.044 [retrieved on May 27, 2008] abstract.

Pfeifer et al. "Genome-wide analysis of DNA copy number changes and LOH in CLL using high-density SNP arrays", Blood, vol. 109, No. 3, Oct. 5, 2006 (Oct. 5, 2006), pp. 1202-1210, XP055085782, ISSN: 0006-4971, DOI: 10.1182/blood-2006-07-034256 *abstract* *tables 2,4*.

Popova et al. "Genome Alteration Print (GAP): a tool to visualize and mine complex cancer genomic profiles obtained by SNP arrays", Genome Biology, Biomed Central Ltd., London, GB, vol.

(56) References Cited

OTHER PUBLICATIONS

10, No. 11, Nov. 11, 2009 (Nov. 11, 2009), p. R128, XP021065372, ISSN: 1465-6906, DOI: 10.1186/GB-2009-10-11-R128, cited in the application abstract.

Rakha et al. "Basal-like breast cancer: a critical review", Journal of Clinical Oncology, American Society of Clinical Oncology, US, vol. 26, No. 14, May 20, 2008 (May 20, 2008), pp. 2568-2581, XP002661082, ISSN: 0732-183X, DOI: 10.1200/JCO.2007.13.1748.

Ramirez, C. et al., "Loss of 1p, 19q, and 10q heterozygosity prospectively predicts prognosis of oligodendroglial tumors-towards individualized tumor treatment?" Neuro. Oncol., May 2010, vol. 12, No. 5, pp. 490-499.

Sakai et al.; Functional resoration of BRCA2 protein by secondary BRCA2 mutations in BRCA2-mutated ovarian carcinoma; Cancer Res; 2009; 69(16):6381-6386.

Sakai et al.; Secondary mutations as a mechanism of cisplatin resistance in BRCA2-mutated cancers; Nature; 2008; 451(7182):1116-1120.

Sang-Wook et al. "Genetic classification of colorectal cancer based on chromosomal loss and microsatellite instability predicts survival", Clinical Cancer Research, The American Association for Cancer Research, US, vol. 8, No. 7, Jul. 1, 2002 (Jul. 1, 2002), pp. 2311-2322, XP002593153, ISSN 1078-0432 *abstract*.

Silva et al., "Loss of heterozygosity in BRCA1 and BRCA2 markers and high-grade malignancy in breast cancer," Breast Cancer Res. & Treatment, Jan. 1999, vol. 53, No. 1, pp. 9-17.

Smid et al. "Patterns and incidence of chromosomal instability and their prognostic relevance in breast cancer subtypes", Breast Cancer Research and Treatment, Kluwer Academic Publishers, BO, vol. 128, No. 1, Jul. 15, 2010 (Jul. 15, 2010), pp. 23-30, XP019916000, ISSN: 1573-7217, DOI: 10.1007/S10549-010-1026-5, abstract; figures 1-3.

Stefansson et al; Genomic profiling of breast tumours in relation to BRCA abnormalities and phenotypes; Breast Cancer Res; 2009; 11(4):R47, 14 pages.

Tan et al.; 'BRCAness' syndrome in ovarian cancer: a case-control study describing the clinical features and outcome of patients with epithelial ovarian cancer asociated with BRCA1 and BRCA2 mutations; J Clin Oncol; 2008;26(34):5530-5536.

The Cancer Genome Atlas Research Network; Integrated genomic analyses of ovarian carcinoma; Nature; 2011; 474(7353):609-615.

Teh M-T et al.: "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005 (Oct. 1, 2005), pp. 8597-8603, XP002703167.

Tseng, R. C. et al., Genomewide loss of heterozygosity and its clinical associations in non-small cell lung cancer, Int. J. Cancer, Nov. 1, 2005, vol. 117, No. 2, pp. 241-247.

Valeri A et al.: "High frequency of allelic losses in high-grade prostate cancer is associated with biochemical progression after radical prostatctomy", Urologic Oncology, Elsevier, New York, NY, US, vol. 23, No. 2, Mar. 1, 2005 (Mar. 1, 2005), pp. 87-92, XP027799195, ISSN: 1078-1439 [retrieved on Mar. 1, 2005].

Vollenbergh et al. "Genomic instability in breast and ovarian cancers: translation into clinical predictive biomarkers", CMLS Cellular and Molecular Life Science, Birkhauser-Verlag, BA, vol. 69, No. 2, Sep. 16, 2011 (Sep. 16, 2011), pp. 223-245, XP019993251, ISSN: 1420-9071, DOI: 10.1007/S00018-011-0809-0, the whole document.

Wilcox et al.; High-resolution methylation analysis of the BRCA1 promoter in ovarian tumors; Cancer Genet Cytogenet; 2005; 159(2): 114-122.

Silver et al., Journal of Clinical Oncology 28(4):1145-1153 (2010). "Efficacy of Neoadjuvant crisplatin in triple-negative breast cancer."

Birkbak et al., "Abstract 4823: Copy number gain and increased expression of BLM and FANCI is associated with sensitivity to genotoxic chemotherapy in triple negative breast and serious ovarian cancer", Cancer Research, 72(8):1 (2012).

Argos et al. "Genomewide scan for loss of heterozygosity and chromosomal amplification in breast carcinoma using single-nucleotide polymorphism arrays", Cancer Genetics and Cytogenetics, vol. 182, No. 2, Apr. 15, 2008.

European Search Report, from Application EP12801070.9, completed on Nov. 21, 2014.

European Search Report, from Application EP12860530.0, completed on Jul. 7, 2015.

Fang et al. "Genomic Differences Between Estrogen Receptor (ER)-Positive and ER-Negative Human Breast Carcinoma Identified by Single Nucleotide Polymorphism Array Comparative Genome Hybridization Analysis", Cancer, vol. 117, No. 10, May 2011.

Hendricks et al. "'Recombomice': The past, present, and future of recombination-detection in mice" DNA Repair, vol. 3, No. 10, Oct. 5, 2004.1.

International Search Report, for application PCT/EP2014/076786, filed Dec. 5, 2014.

International Search Report, for application PCT/US2011/026098, filed Feb. 24, 2011.

Isakoff et al., "TBCRC009: A Multicenter Phase II Clinical Trial of Platinum Monotherapy With Biomarker Assessment in Metastatic Triple-Negative Breast Cancer," J Clin Oncol, 2015, 1-8.

Kaklamani et al., "Phase II neoadjuvant clinical trial of carboplatin and eribulin in women with triple negative early-stage breast cancer (NCT01372579)," Breast Cancer Res Treat, 2015, 151:629-638.

Lin et al. "Integrated analysis of copy number alterations and loss of heterozygosity in human pancreatic cancer using a high-resolution, single nucleotide polymorphism array", Oncology, vol. 75, No. 1-2, Sep. 1, 2008.

Maeck et al. "Genetics instability in myelodysplastic syndrome: Detection of microsatellite instability and loss of heterozygosity in bone marrow samples with karyotype alterations" British Journal of Haematology, vol. 109, No. 4, Jun. 2000.

Mateo et al., "Appraising iniparib, the PARP inhibitor that never was—what must we learn?," Nature, Dec. 2013, 10: 688-696.

Mei et al.: "Genome-wide detection of Allelic Imbalance Using Human SNPs and High-density DNA arrays", Genome Research, vol. 10, No. 8, Aug. 1, 2000, pp. 1126-1137.

Mukhopadhyay et al., "Clinicopathological Features of Homologous Recombination-Deficient Epithelial Ovarian Cancers: Sensitivity to PARP Inhibitors, Platinum, and Survival," Cancer Research, 72(22), 2012, 5675-5682.

Novak et al: "A high-resolution allelotype of B-cell chronic lymphocytic leukemia (B-CLL)", Blood, American Society of Hematology, US, vol. 100, No. 5, Sep. 1, 2002, pp. 1787-1794.

Patel et al., "Failure of Iniparib to Inhibit Poly(ADP-Ribose) Polymerase in Vitro," Clin Cancer Res, 2012, 1655-1662.

Peng et al., "Genome-wide transcriptome profiling of homologous recombination DNA repair," Nature Communications, 2014, 1-11.

Schouten et al., "Challengers in the Use of DNA Repair Deficiency As a Biomarker in Breast Cancer," Journal of Clinical Oncology, 2015, 33(17): 1867-1869.

Telli et al., "Phase II Study of Gemcitabine, Carboplatin, and Iniparib as Neoadjuvant Therapy for Triple-Negative and BRCA1/2 Mutation-Associated Breast Cancer With Assessment of a Tumor-Based Measure of Genomic Instability: PrECOG0105," J Clin Oncol, 2015, 1-7.

Volchenboum et al. "Comparison of Primary Neuroblastoma Tumors and Derivative Early-Passage Cell Lines Using Genome-Wide Single Nucleotide Polymorphism Array Analysis", Cancer Research, vol. 69, No. 10, May 15, 2009.

Wilcoxen et al., "Homologous recombination deficiency (HRD) score enriches for niraparib sensitive high grade ovarian tumors," Supplemental Abstract, 2015, 1 page.

Wilcoxen et al., "Use of homologous recombination deficiency (HRD) score to enrich for niraparib sensitive high grade ovarian tumors," J Clin Oncol, 2015, Supplemental Abstract: 5532, 2 pages.

Xiao et al., "The XIST Noncoding RNA Functions Independently of BRCA1 in X Inactivation," Cell, Mar. 2007, 128:977-989.

Takahashi, Clinical Cancer Research, 13(1):111-120 (2007). "Clonal and Parallel Evolution of Primary Lung Cancers and Their Metastases Revealed by Molecular Dissection of Cancer Cells."

(56) References Cited

OTHER PUBLICATIONS

Juul et al., Cancer Research, 69(24):509S-510S (2009). "A Genomic-Profile Derived Summary Measure of Chromosomal Breakpoints Predicts Response to Treatment with the DNA-Damaging Agent Cisplatin."
Ott et al., Clinical Cancer Research, The American Association for Cancer Research, US, 9(6):2307-2315 (2003)."Chromosomal Instability rather than p53 mutation is associated with response to neoadjuvant cisplatin-based chemotherapy in gastric carcinoma".
European Communication Response for Application 11757992.0, dated Mar. 21, 2014.
European Communication Response for Application 11757992.0, dated Dec. 9, 2014.
European Communication Response for Application 11796544.2, dated Sep. 28, 2015.
European Communication Response, for Application 11796544.2, dated Feb. 1, 2016.
European Communication Response, for Application 11796544.2, dated Aug. 3, 2015.
European Communication Response, for Application 12860530.0, dated Feb. 10, 2016.
European Communication, for Application 11757992.0, dated Aug. 5, 2014.
European Communication, for Application 11757992.0, dated Dec. 10, 2013.
European Communication, for Application 11796544.2, dated Jan. 20, 2016.
European Communication, for Application 11796544.2, dated May 11, 2015.
European Communication, for Application 11796544.2, dated Sep. 11, 2015.
European Communication, for Application 12801070.9, dated Apr. 1, 2016.
European Intention to Grant, for Application 11757992.0, dated Sep. 28, 2015.
European Intention to Grant, for Application 11796544.2, dated Mar. 31, 2016.
Extended European Search Report, for Application EP15189527.3, dated Mar. 31, 2016.
Fontanillas et al., "Key considerations for measuring allelic expression on a genomic scale using high-throughput sequencing", Mol Ecol. 9(Suppl 1):212-227 (2010).
Heap et al., "Genome-wide analysis of allelic expression imbalance in human primary cells by high-throughput transcriptome resequencing", Human Molecular Genetics 19(1):122-134 (2010).
International Preliminary Report on Patentability, app. No. PCT/US2012/071380, dated Jun. 24, 2014.
International Search Report, for application PCT/US2015/045561, dated Nov. 9, 2015.
Japanese Patent Application Kohyo Publication No. (JP-A) 2008-538496 (Unexamined Japanese National Phase Publication Corresponding to a Non-Japanese International Publication).
Johansson et al., "Abstract 4833: A genomic portrait of tumor progression using next-generation sequencing", Cancer Res. 71:4833 (2011).
Patocs et al., "Breast-Cancer Stromal Cells with TP53 Mutations and Nodal Metastases", N. Engl. J. Med. 357:2543-2551 (2007).
Popova et al., "Ploidy and Large-Scale Genomic Instability Consistently Identify Basal-like Breast Carcinomas with BRCA1/2 Inactivation", Cancer Res. 72(21):5454-62 (2012).
Santana-Davila et al., "Treatment options for patients with triple-negative breast cancer", Journal of Hematology & Oncology 3:42 (2010).
Tai et al., "High-Throughput Loss-of-Heterozygosity Study of Chromosome 3p in Lung Cancer Using Single-Nucleotide Polymorphism Markers", Cancer Res. 66(8):4133-4138 (2006).
Tuna et al., "Association between Acquired Uniparental Disomy and Homozygous Mutations and HER2/ER/PR Status in Breast Cancer", PLoS One 5(11):e15094 (2010).
Walsh et al., "Genome-Wide Loss of Heterozygosity and Uniparental Disomy in BRCA1/2-Associated Ovarian Carcinomas", Clin Cancer Res. 14(23):7645-7651 (2008).
Zhao et al., "Systematic detection of putative tumor suppressor genes through the combined use of exome and transcriptome sequencing", Genome Biol. 11:R114,1-14 (2010).
Abkevich et al. "Patterns of genomic loss of heterozygosity predict homologous recombination repair defects in epithelial ovarian cancer", British Journal of Cancer, vol. 107, No. 10, Oct. 9, 2012 (Oct. 9, 2012), pp. 1776-1782, XP055085758, ISSN: 0007-0920, DOI: 10.1038/bjc.2012.451 *the whole document*.
Abkevich et al. "Supplemental Material: Table S1: Validation of copy number determinations by Real Time PCR SNP ID Adjacent Gene Sample Copy Number by Real-Time PCR Copy Number by CCNT SNP A",—1712744 CDKN2A HF505 0.010 0.47 HF1382 0.14 0, Oct. 1, 2006 (Oct. 1, 2006), pp. 5-1713144, XP055085899, Retrieved from the Internet: URL: http://cancerres.aacrjournals.org/content/suppl/2006/10/04/66.19.9428.DC2/Supplementary_Tables_1-5.pdf [retrieved on Oct. 29, 2013] the whole document.
Al-Mulla et al., "Metastatic recurrence of early-stage colorectal cancer is linked to loss of heterozygosity on chromosomes 4 and 14q" Journal of Clinical Pathology, vol. 59, No. 6, pp. 624-630 (2006) See whole document.
Ashworth et al. "A Synthetic Lethal Therapeutic Approach: Poly(ADP) Ribose Polymerase Inhibiors for the Treatment of Cancers Deficient in DNA Double-Strand Break Repair", Journal of Clinical Oncology, vol. 26, No. 22, Aug. 1, 2008 (Aug. 1, 2008), pp. 3785-3790, XP055039560, ISSN: 0732-183X, DOI: 10.1200/JCO.2008.16/0812, abstract.
Beder L B et al.: "Genome-wide analyses on loss of heterozygosity in head and neck squamous cell carcinomas", Laboratory Investigation, vol. 83, No. 1, 2003, pp. 99-105, XP002703165.
Beroukhim et al. "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006), p. 2397, XP055085786, ISSN: 1367-4803, DOI: 1367-4803 (2003)019[2397:AFLGM]2.0.CO; 2 *abstract* *p. 329, col. 1, paragraph 4—col. 2, line 1; table 2*.
Bryant et al. "Specific killing of BRCA2-deficient tumours with inhibitors of poly(ADP-ribose) polmerase"; Nature; 2005; 434(7035):913-917.
Buch H N et al.: "Prediction of recurrence of nonfunctioning pituitary tumours by loss of heterozygosity analysis", Clinical Endocrinology, vol. 61, 2004, p. 19-22, XP002703163.
Calvert et al. "245 Invited PARP inhibitors in cancer treatment", European Journal of Cancer. Supplement, Pergamon, Oxford, GB, vol. 6, No. 12, Oct. 1, 2008 (Oct. 1, 2008), p. 80, XP025534307, ISSN: 1359-6349 DOI: 10.1016/S1359-6349 (08) 72177-3 [retrieved on Oct. 1, 2008] abstract.
Cerbinskaite et al.; Defective homologous recombination in human cancers; Cancer Treat Rev; 2012; Epub 2011; 38(2): 89-100; doi:10.1016/j.ctrv.2011.04.015.
Cheung T H et al.: "Clinicopathologic significance of loss of heterozygosity on chromosome 1 in cervical cancer" Gynecologic Oncology, Academic Press, London, GB, vol. 96, No. 2, Feb. 1, 2005 (Feb. 1, 2005), pp. 510-515, XP027205508, ISSN: 0090-8258 [retrieved on Jan. 18, 2005].
Dann et al.; BRCA1/2 mutations and expression: response to platinum chemotherapy in patients with advanced stage epithelial ovarian cancer; Gynecol Oncol; 2012;125(3):677-682.
De Soto et al. "The inhibition and treatment of breast cancer with poly (ADP-ribose) polymerase (PARP-1) inhibitors", International Journal of Biological Sciences, Ivyspring International Publisher, AU, vol. 2, No. 4, Jun. 10, 2006 (Jun. 10, 2006), pp. 179-185, XP007906272, ISSN: 1449-2288, abstract.
Edwards et al.; Resistance to therapy caused by intragenic deletion in BRCA2; Nature; 2008; 451(7182):1111-1115.
Etemadmoghadam et al. "Integradted genowide DNA copy number and expression analysis identifies distinct mechanisms of primary chemoresistance in ovarion carcinoma", Clinical Cancer Research, 15(4):1417-1427 (2009).
Extended European Search Report, for application EP11796544.2, filed Nov. 18, 2013.

(56) References Cited

OTHER PUBLICATIONS

Extended European Search Report, for application EP11748075.6, filed Feb. 24, 2011.
Farmer et al.; Targeting DNA repair defect in BRCA mutant cells as a therapeutic strategy; Nature; 2005; 434 (7035):917-921.
Feltmate C M et al.: "Whole-genome allelotyping identified distinct loss-of-heterozygosity patterns in mucinous ovarian and appendiceal carcinomas", Clinical Cancer Research, vol. 11, No. 21, Nov. 1, 2005 (Nov. 1, 2005), pp. 7651-7657, XP002703164.
Ferreira et al. "Array CGH and gene-expression profiling reveals distinct genomic instability patterns associated with DNA repair and cell-cycle checkpoint pathways in Ewings's sarcoma," Oncogene, 27(4):2084-2090 (2008).
Filopanti et al., "Loss of heterozygosity at the SS receptor type 5 locus in human GH- and TSH-secreting pituitary adenomas," J. Endocrinol. Invest., Nov. 2004, vol. 27, No. 10, pp. 937-942.
Franko, J. et al., "Loss of heterozygosity predicts poor survival after resection of pancreatic adenocarcinoma," J. Gastrointest. Surg., Oct. 2008, vol. 12, No. 10, pp. 1664-1723.
Friedenson; BRCA1 and BRCA2 pathways and the risk of cancers other than breast or ovarian; MedGenMed; 2005; 7(2):60, 25 pages.
Gelmon et al.; Olaparib in patients with recurrent high-grade serous or poorly differentiated ovarian carcinoma or triple-negative breast cancer: a phase 2, multicentre, open-label, non-randomised study; Lancet Oncol; 2011;12(9):852-861.
Goransson et al. "Quantification of Normal Cell Fraction and Copy Number Neutral LOH in Clinical Lung Cancer Samples Using SNP Array Data", PLOS ONE, vol. 4, No. 6, Jun. 26, 2009 (Jun. 26, 2009), p. e6057, XP055085703, ISSN: 1932-6203, DOI: 10.1371/journal.pone.0006057 *the whole document*.
Gorringe et al. "Are there any more ovarian tumor suppressor genes? A new perspective using ultra high-resoution copy number and loss of heterozygosity analysis", Genes Chromosomes & Cancer, John Wiley & Sons, Inc, US, vol. 48, No. 10, Oct. 1, 2009 (Oct. 1, 2009), pp. 931-942, XP002703162, ISSN: 1045-2257, DOI: 10.1002/GCC.20694 [retrieved on Jul. 14, 2009] *abstract* *p. 932, col. 2, paragraph 2-paragraph3*.
Graziani et al. "PARP-1 inhibition to treat cancer, ischemia, inflammation", Pharmacological Research, Academic Press, London, GB, vol. 52, No. 1, Jul. 1, 2005 (Jul. 1, 2005), pp. 1-4, XP004902631, ISSN: 1043-6618, DOI: 10.1016/J.PHRS.2005.02.007, the whole document.
Gudmundsdottir et al. "The roles of BRCA1 and BRCA2 and associated proteins in the maintenance of genomic stability", Oncogene, vol. 25, No. 43, Sep. 25, 2006 (Sep. 25, 2006), pp. 5864-5874, XP055040467, ISSN: 0950-9232, DOI: 10.1038/sj.onc.1209874.
Gunnarsson et al. "Large but not small copy-number alterations correlate to high-risk genomic aberrations and survival in chronic lymphocytic lukemia: a high-resolution genomic screening of newly diagnosed patients", Lukemia, vol. 24, No. 1, Jan. 1, 2010 (Jan. 1, 2010), pp. 211-215, XP055085701, ISSN: 0887-6924, DOI: 10.1038/leu.2009.187 *the whole document*.
Hampton et al., "Simultaneous assessment of loss of heterozygosity at multiple microsatellite loci using semi-automated fluorescence-based detection: Subregional mapping of chromosome 4 in cervical carcinoma," PNAS, Jun. 1996, vol. 93, No. 13, pp. 6704-6709.
Heinsohn, S. et al., "Determination of the prognostic value of loss of heterzygosity at the retinoblastoma gene in osteosarcoma," Int. J. Oncol., May 2007, vol. 30, No. 5, pp. 1205-1214.
Hennessy et al.; Somatic mutations in BRCA 1 and BRCA2 could expand the number of patients that benefit from poly (ADP ribose) polymerase inhibitors in ovarian cancer; J Clin Oncol; 2010; 28(22):3570-3576.
Holstege et al.; BRCA1-mutated and basal-like breast cancers have similar aCGH profiles and a high incidence of protein truncating TP53 mutations; BMC Cancer; 2010; 10:654, 15 pages.
Carr et aL, "High-resolution analysis of allelic imbalance in neuroblastoma cell lines by single nucleotide polymorphism arrays", Cancer Genetics and Cytogenetics 172(2):127-138 (2007).

De Preter et al., "Application of laser capture microdissection in genetic analysis of neuroblastoma and neuroblastoma precursor cells", Cancer Letters 197(1-2):53-61 (2003).
Li et al., "Major copy proportion analysis of tumor samples using SNP arrays", BMC Bioinformatics 9:204 (2008).
Soule et al., "Isolation and Characterization of a Spontaneously Immortalized Human Breast Epithelial Cell Line, MCF-10", Cancer Research 50(18):6075-6086 (1990).
Yaris et al., "Primary cerebral neuroblastoma: a case treated with adjuvant chemotherapy and radiotherapy", The Turkish Journal of Pediatrics 46(2):182-185 (2004).
Anonymous, "Myriad's HRD Test Significantly Predicts Response to Cisplatin Treatment in Patients with Triple Negative Breast Cancer in Second Research Study", Myriad, Dec. 14, 2013.
Malek, Olaf, Response to Communication under Rule 69 EPC in Application No. 15189527.3, dated Sep. 30, 2016.
Botz, Jurgen, European Communication RE: Appl. No. 128060530. 0, dated Nov. 28, 2016.
Extended European Search Report, Appl. No. EP14779403.6, dated Oct. 28, 2016.
Extended European Search Report, Appl. No. EP16166825.6, dated Nov. 11, 2016.
Telli et al., "Abstract PD09-04: Homologous Recombination Deficiency (HRD) score predicts pathologic response following neoadjuvant platinum-based therapy in triple-negative and BRCA1/2 mutation-associated breast cancer (BC)", Cancer Research 72(24), Dec. 2012.
European Communication Response, for application 12860530.0, dated Mar. 17, 2017.
Juul et al., "Amount of Allelic Imbalance Predicts Response to Cisplatin in Breast and Ovarian Cancer", Annals of Oncology 21(4) iv30 Abstracts (2010).
Australian Office Action Response from Application No. 2012358244, dated Aug. 9, 2017.
Bernardini et al., "The use of cytogenetics in understanding ovarian cancer", Biomed Pharmacother 58(1) 17-23 (2004).
Campbell et al., "A genetic variant that disrupts MET transcription is associated with autism", Proc Natl Acad Sci USA 103(45) 16834-16839 (2006).
Canadian Office Action Response for Application No. 2,802,882, dated Aug. 22, 2017.
Canadian Office Action from Application No. 2,807,823, dated Jun. 6, 2017.
Duncavage et al., "Hybrid capture and next-generation sequencing identify viral integration sites from formalin-fixed, paraffin-embedded tissue", J Mol Diagn 13(3) 325-333 (2011).
European Communication from Application No. 12801070.9. dated Aug. 25, 2017.
European Communication from Application No. 12860530.0, dated Sep. 6, 2017.
European Communication from Application No. 14779403.6, dated Aug. 31, 2017.
European Communication from Application No. 15757372.6, dated Nov. 23, 2017.
European Communication Response for Application No. 15866475. 5, dated Jan. 10, 2018.
International Search Report for Application No. PCT/US2017/023152 dated Jun. 7, 2017.
Japanese Office Action for Application No. 2014-548965, dated Aug. 2, 2017.
Japanese Office Action for Application No. 2014-548965, dated Oct. 31, 2016.
Japanese Office Action Response from Application No. 2014-548965, dated Nov. 28, 2017.
Japanese Opposition from Patent No. 6117194, dated Oct. 19, 2017.
Johansson et al., "Targeted resequencing of candidate genes using selector probes", Nucleic Acids Res 39(2) e8 (2011).
Juul et al., "Amount of Allelic Imbalance Predicts Response to Cisplatin in Breast and Ovarian Cancer", Annals of Oncology 21(Suppl 4) 33P (2010).
Kamat et al., "Chemotherapy induced microsatellite instability and loss of heterozygosity in chromosomes 2, 5, 10, and 17 in solid tumor patients", Cancer Cell Int 14(1) 118 (2014).

(56) References Cited

OTHER PUBLICATIONS

Kiialainen et al., "Performance of microarray and liquid based capture methods for target enrichment for massively parallel sequencing and SNP discovery", PLoS One 6(2) e16486 (2011).
Kudoh Et al., "Gains of 1q21-q22 and 13q12-q14 are potential indicators for resistance to cisplatin-based chemotherapy in ovarian cancer patients", Clin Cancer Res 5(9) 2526-2531 (1999).
Ledermann et al., "Olaparib maintenance therapy in platinum-sensitive relapsed ovarian cancer", N Engl J Med 366(15) 1382-1392 (2012).
Ross et al., "Comprehensive next-generation sequencing for clinically actionable mutations from formalin-fixed cancer tissues", Journal of Clinical Oncology 29(Suppl 15) 10564 (2011) Abstract Only.
Schweiger et al., "Genome-wide massively parallel sequencing of formaldehyde fixed-paraffin embedded (FFPE) tumor tissues for copy-number- and mutation-analysis", PLoS One 4(5) e5548 (2009).
Tommasi et al., "655Val and 1170Pro ERBB2 SNPs in familial breast cancer risk and BRCA1 alterations", Cell Oncol 29(3) 241-248 (2007).
Varley et al., "Nested Patch PCR enables highly multiplexed mutation discovery in candidate genes", Genome Res 18(11) 1844-1850 (2008).
Zuchner et al., "Linkage and association study of late-onset Alzheimer disease families linked to 9p21.3", Ann Hum Genet 72(Pt 6) 725-731 (2008).
Telli et al., "Abstract PD09-04: Homologous Recombination Deficiency (HRD) score predicts pathological response following neoadjuvant platinum-based therapy in triple-negative and BRCA1/2 mutation-associated breast cancer (BBC)", Cancer Research 72(24) (2012).
Wilcoxen et al., "Use of Homologous recombination deficiency (HRD) score enriches for niraparib sensitive high grade ovarian tumors" J Clin Oncol Supplemental Abstract 5532 (2015).
Canadian Office Action from Application No. 2,802,882, dated Feb. 24, 2017.
European Communication from Application No. 12801070.9, dated Dec. 22, 2016.
European Communication Response for Application No. 12860530.0, dated Mar. 17, 2017.
Declaration under 37 C.F.R. § 1.132 for inventor Dr. Kristen Timms, Ph. D., filed Apr. 4, 2014 with USPTO.
Hansen et al., "Clinical significance of homologous recombination deficiency score testing in endometrial cancer patients", presented at ASCO Jun. 6, 2016.
Lheureux et al., "Long-term responders on olaparib maintenance in high-grade serous ovarian cancer: Clinical and molecular characterization", Clin. Cancer Res. (2017).
Mills et al., "Homologous Recombination Deficiency (HRD) Score Shows Superior Association with Outcome Compared to its Individual Score Components (LOH, TAI, and LST Scores) in Platinum Treated Serous Ovarian cancer", Presented at SGO Mar. 19, 2016.
O'Brien et al. "Converting cancer mutations into therapeutic opportunities," EMBO Mol. Med. 1:297-299 (2009).
Examiner requisition issued during the prosecution of CA Application No. 2,802,882, dated Feb. 24, 2017.
Response to Communication pursuant to Article 94(3) EPC issued during the prosecution of EP Application No. 12801070.9, dated Apr. 20, 2017.
Response to Communication pursuant to Article 94(3) EPC issued during the prosecution of EP Application No. 12860530.0, dated Mar. 17, 2017.
Shahda et al., "Homologous Recombination Deficiency (HRD) in Patients with Pancreatic Cancer and Response to Chemotherapy", Presented at ASCO-GI Jan. 20, 2017.
Timms et al., "Association of BRCA1/2 defects with genomic scores predictive of DNA damage repair deficiency among breast cancer subtypes", Breast Cancer Research 16:475 (2014).
Timms et al., "DNA repair deficiencies in ovarian cancer: Genomic analysis of high grade serous ovarian tumors from the NOVA study", Presented at ESMO Sep. 26, 2015.
Timms et al., "The Molecular Landscape of Genome Instability in Prostate Cancer", Presented at ESMO—Oct. 10, 2016.
Response to Communication pursuant to Rules 70(3) and 70a(2) for EP Application No. 14779403.6, filed May 8, 2017.
Written Amendment for JP Application No. 2014-548965, filed Apr. 27, 2017.
Audeh, "Novel treatment strategies in triple-negative breast cancer: specific role of poly(adenosine diphosphate-ribose) polymerase inhibition", Pharmacogenomics Pers Med 7: 307-316 (2014).
Australian Office Action from application No. 2012358244, dated Apr. 24, 2018.
Australian Office Action Response from application No. 2012358244, dated Jul. 30, 2018.
Australian Office Action Response from application No. 2012358244, dated Apr. 19, 2018.
Australian Voluntary Amendment from application No. 2014248007, dated Apr. 20, 2018.
Beroukhim et al., "Assessing the significance of chromosomal aberrations in cancer: methodology and application to glioma", Proc Natl Acad Sci USA 104(50) 20007-20012 (2007).
Canadian Office Action from Application No. 2,839,210, dated Feb. 28, 2018.
European Communication Response from Application No. 12801070.9, dated Feb. 9, 2018, 3 pages.
European Communication Response from Application No. 12860530.0, dated Mar. 12, 2018, 6 pages.
European Communication Response from Application No. 14779403.6, dated Feb. 12, 2018, 10 pages.
Extended European Search Report from Application No. EP17194403.6, dated Feb. 8, 2018, 15 pages.
Haluska et al., "Homologous recombination deficiency (HRD) score and niraparib efficacy in high grade ovarian cancer", Oral Presentation, Plenary Session Six, Nov. 20, 2014.
Horiuchi, "Epigenetic Changes during Ovarian Cancer Development and Progression—BRCA1 Methylation and S1004 Hypomethylation", Ada Obst Gynaex JP 60(11) 1844-1854 (2008).
International Preliminary Report on Patentability and Written Opinion from Application No. PCT/US2011/040953, dated Jan. 3, 2013, 6 pages.
International Preliminary Report on Patentability and Written Opinion from Application No. PCT/US2011/048427, dated Mar. 7, 2013, 11 pages.
International Preliminary Report on Patentability and Written Opinion from Application No. PCT/US2012/042668, dated Jan. 3, 2014, 7 pages.
International Preliminary Report on Patentability and Written Opinion from Application No. PCT/US2014/033014, dated Oct. 15, 2015, 6 pages.
International Preliminary Report on Patentability and Written Opinion from Application No. PCT/US2015/045561, dated Mar. 2, 2017, 8 pages.
International Preliminary Report on Patentability and Written Opinion from Application No. PCT/US2015/064473, dated Jun. 22, 2017, 10 pages.
International Search Report and Written Opinion from Application No. PCT/US2014/033014, dated Aug. 12, 2014, 6 pages.
International Search Report and Written Opinion from Application No. PCT/US2015/064473, dated Apr. 14, 2016, 14 pages.
Japanese Office Action from Application No. 2016-506657, dated Jan. 31, 2018, 3 pages.
Roscilli et al., "Abstract 685: PARP inhibitor MK-4827 is synthetic lethal for tumors with homologous recombination defects associated with ATM-deficiency, PTEN-deletion and microsatellite instability (MSI)" Proceedings AACR 101st Annual Meeting, 2010.
Sandhu et al., "The poly(ADP-ribose) polymerase inhibitor niraparib (MK4827) in BRCA mutation carriers and patients with sporadic cancer a phase 1 dose-escalation trial", Lancet Oncol 14(9) 882-892 (2013).
Timms et al., "Abstract P6-05-10: Association between BRCA1/2 status and DNA-based assays for homologous recombination defi-

(56) References Cited

OTHER PUBLICATIONS ciency in breast cancer", Abstracts: Thirty-Sixth Annual CTRC-AACR San Antonion Breast Cancer Symposium (2013).
European Communication for Application No. 12860530, dated May 11, 2018, 70 pages.
European Communication for Application No. 14779403, dated Jun. 13, 2018, 6 pages.
European Communication for Application No. 15757372, dated Jun. 14, 2018, 134 pages.
European Communication for Application No. 15866475, dated Jun. 1, 2018, 1 page.
European Communication Response for Application No. 12801070, dated Jul. 18, 2018, 8 pages.
European Communication Response for Application No. 12860530, dated May 15, 2018, 1 page.
European Communication Response for Application No. 15757372, dated Jun. 1, 2018, 2 pages.
European Communication Response for Application No. 12860530.0, dated Mar. 12, 2018, 6 pages.
European Search Report for Application No. 15866475, dated May 14, 2018.
European Communication Response for Application No. 1286053, dated Jun. 27, 2018.
Jacobs et al., "Genome-wide, high-resolution detection of copy number, loss of heterozygosity, and genotypes from formalin-fixed, paraffin-embedded tumor tissue using microarrays", Cancer Res 67(6) 2544-2551 (2007).

\* cited by examiner $$MCP = \frac{\text{COPY NUMBER OF MAJOR ALLELE}}{\text{COPY NUMBER OF MAJOR + MINOR ALLELE}}$$
NORMAL DIPLOID
$$MCP = \frac{1}{1+1} = 0.5$$
TELOMERIC AI FROM COPY NUMBER NEUTRAL AI EVENT
$$MCP = \frac{2}{2+0} = 1$$
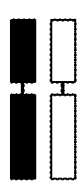
TELOMERIC AI FROM COPY NUMBER DECREASE
$$MCP = \frac{1}{1+0} = 1$$
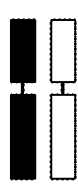
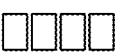
AI FROM MONO-ALLELIC COPY NUMBER GAIN
$$MCP = \frac{4}{4+1} = 0.8$$
*FIG. 2*

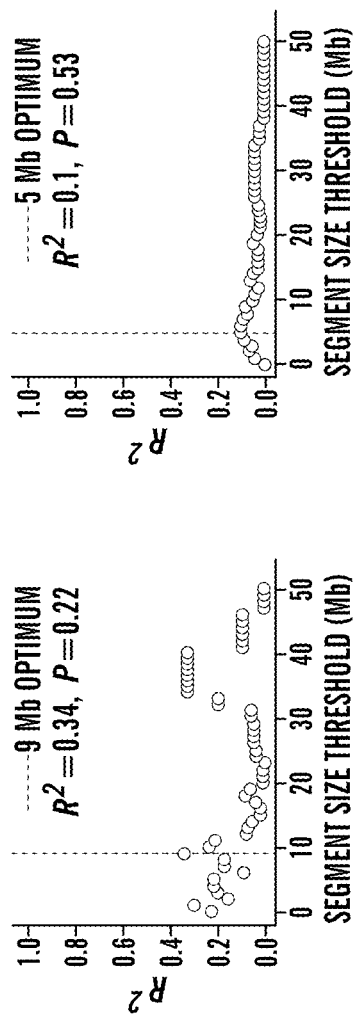
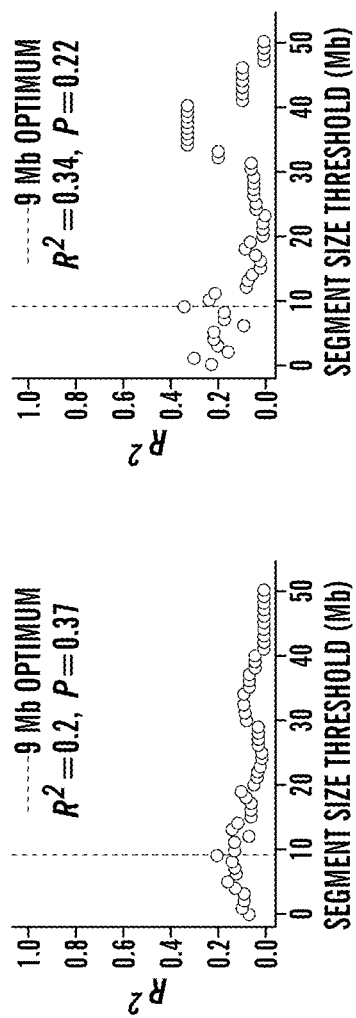
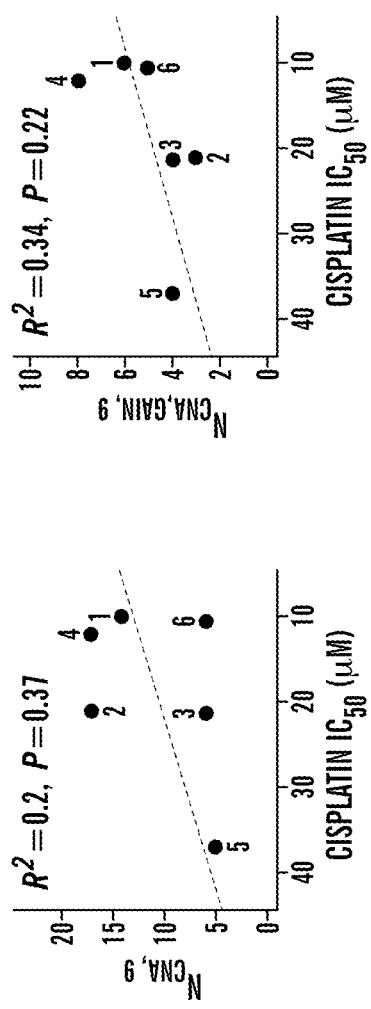
FIG. 5A  FIG. 5B  FIG. 5C
FIG. 5D  FIG. 5E  FIG. 5F

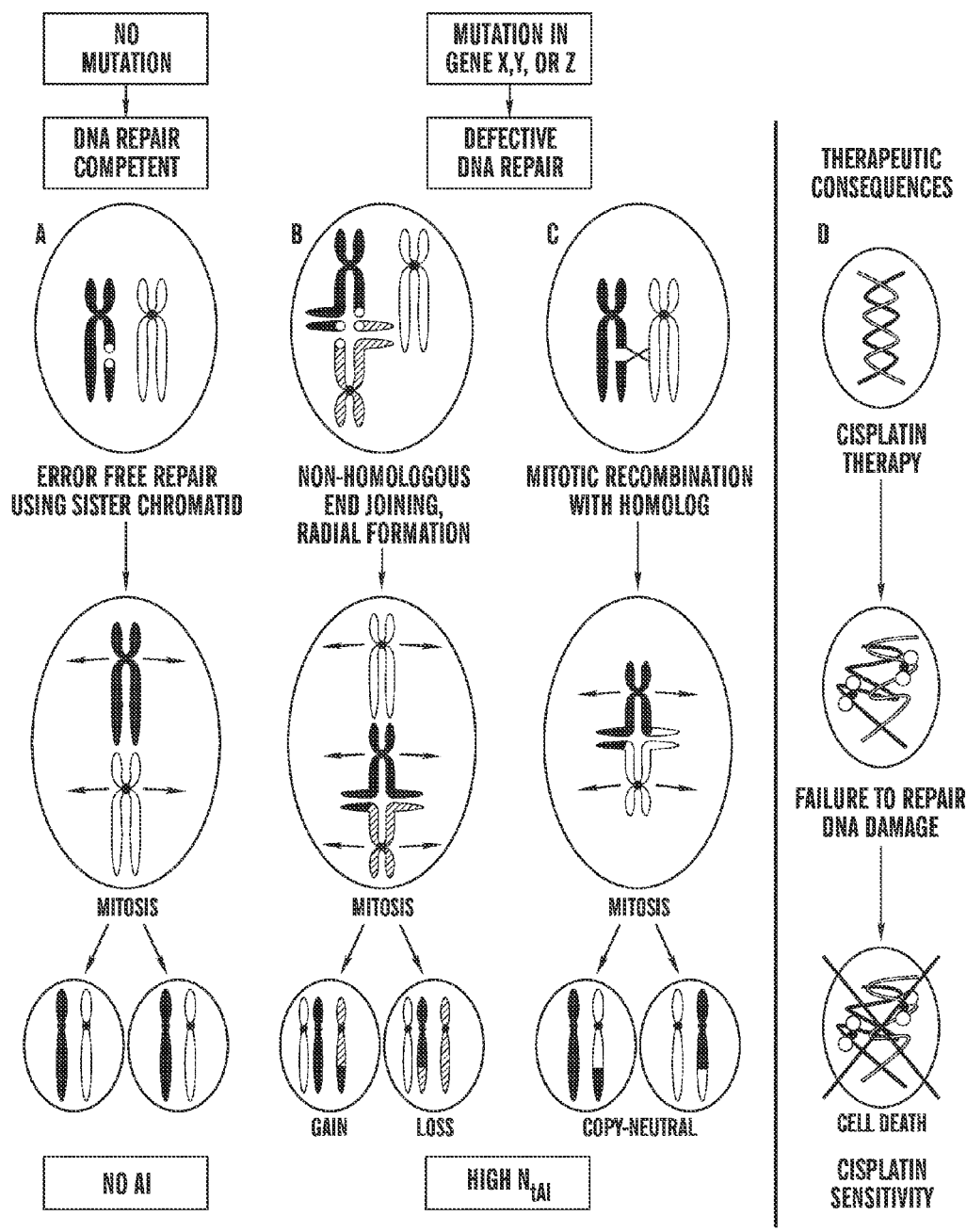
*FIG. 15A*   *FIG. 15B*   *FIG. 15C*   *FIG. 15D*

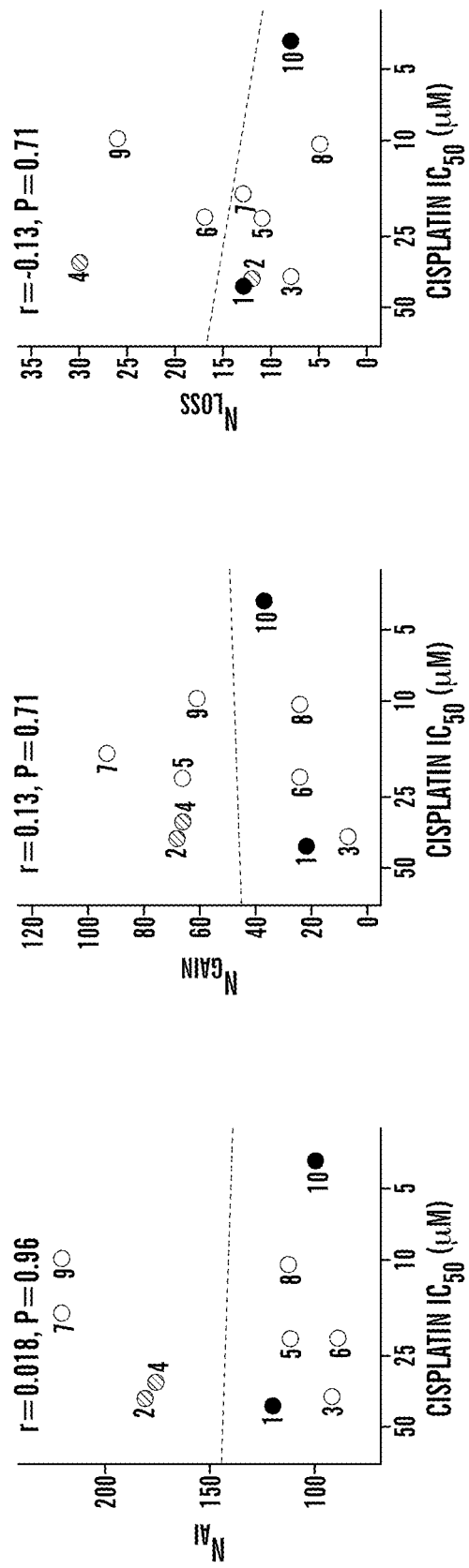

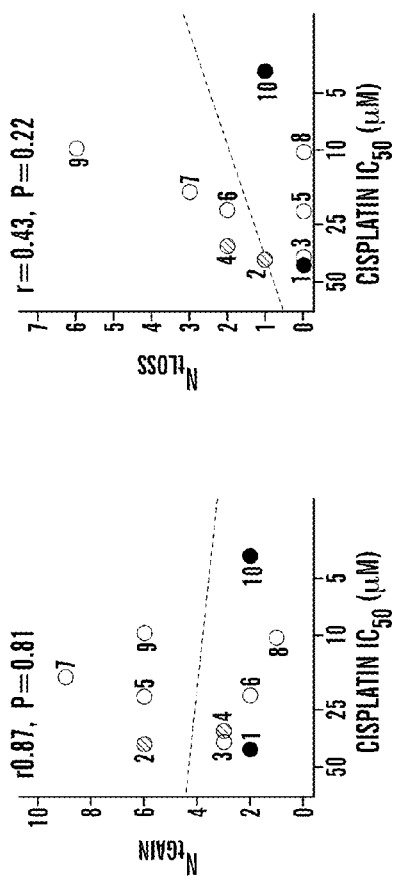
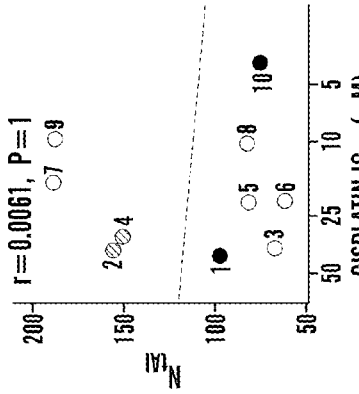
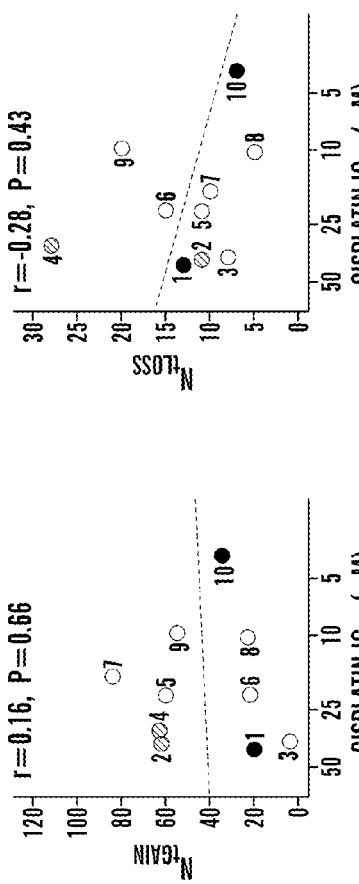
FIG. 18A FIG. 18B FIG. 18C FIG. 18D FIG. 18E

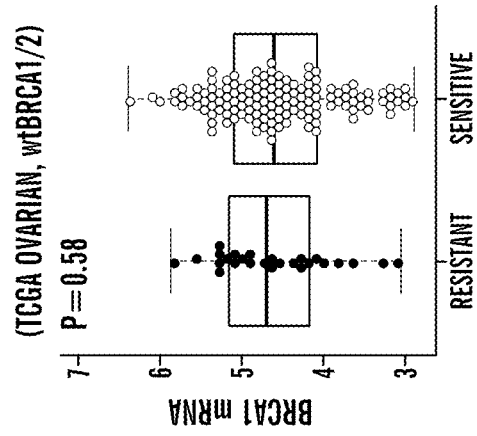
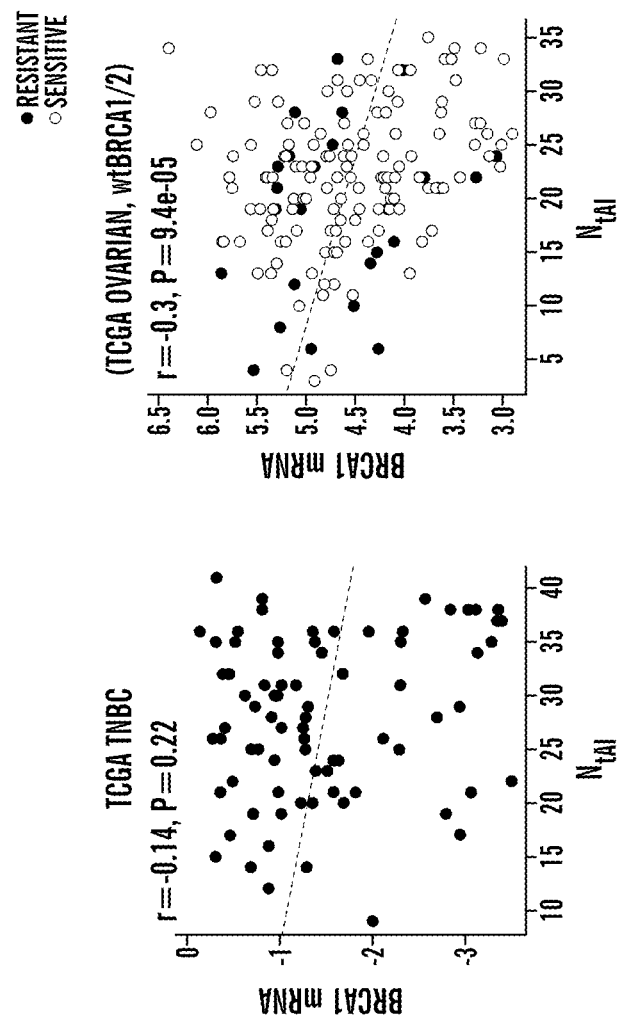
FIG. 22A FIG. 22B FIG. 22C

METHODS FOR PREDICTING ANTI-CANCER RESPONSE

CROSS-REFERENCE TO RELATED APPLICATIONS

This application is a continuation application of International Application No. PCT/US13/27295 filed Feb. 22, 2013, which claims benefit under 35 U.S.C. 119(e) of U.S. provisional applications No. 61/602,460 filed Feb. 23, 2012, and 61/604,810 filed Feb. 29, 2012, the contents of which are incorporated herein by reference in their entirety.

GOVERNMENT SUPPORT

This invention was made with government support under grant number CA089393097193 awarded by National Institutes of Health. The Government has certain rights in the invention.

BACKGROUND OF THE INVENTION

Medical oncologists have benefited greatly from relatively recent efforts to dissect and understand the genetic elements underlying mammalian cancer. The identification of specific genetic predispositions, such as mutations in BRCA-1, BRCA2, and HER2, has provided key insights into the mechanisms underlying tumorigenesis and has proven useful for the design of new generations of targeted approaches for clinical intervention. With the determination of the human genome sequence and improvements in sequencing and bioinformatics technologies, systematic analyses of genetic alterations in human cancers have become possible.

However, clinical interventions based upon this information have been severely hampered by the fact that often only a percentage of patients will respond favorably to a particular anti-cancer treatment. Medical oncologists currently cannot generally predict which patients will or will not respond to a proposed chemotherapeutic treatment.

Accordingly, there is a great need in the art to identify patient responsiveness to particular anti-cancer therapies.

SUMMARY OF THE INVENTION

The present invention is based, at least in part, on the discovery that certain patterns of DNA aberrations described herein are predictive of anti-cancer response of the cells harboring such DNA aberrations to anti-cancer therapies.

Accordingly, in one aspect, the present invention features a method for predicting the outcome of anti-cancer treatment of a subject with a cell hyperproliferative disorder, comprising determining a global chromosomal aberration score (GCAS), comprising obtaining a biological sample from the subject and determining whether a plurality of chromosomal regions displaying a chromosomal aberration exists within a plurality of chromosomal loci, wherein said chromosomal aberrations are selected from the group consisting of allelic imbalance (AI), loss of heterozygosity (LOH), copy number aberrations (CNA), copy number gain (CNG), copy number decrease (CND) and combinations thereof, relative to a control, and wherein the presence of a plurality of chromosomal regions displaying said chromosomal aberrations predicts the outcome of anti-cancer treatment of the subject. The subject can be a mammal, such as a human.

For example, mutations in BRCA1 or BRCA2 cause defects in DNA repair that predict sensitivity to platinum salts in breast and ovarian cancer; however, some patients without BRCA mutations also benefit from these agents. This study shows that defects in DNA repair that cause platinum sensitivity can be inferred from the number of allelic imbalance (AI) or the number of telomeric allelic imbalance (NtAI), a measure of genomic aberration in tumors. NtAI may identify cancer patients without BRCA mutations who are likely to benefit from platinum-based therapy.

In one aspect, the anti-cancer treatment is chemotherapy treatment. In another embodiment, the anti-cancer treatment comprises platinum-based chemotherapeutic agents (e.g., cisplatin, carboplatin, oxaliplatin, nedaplatin, and iproplatin).

In another aspect, the cell hyperproliferative disorder is selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, and vagina.

In still another aspect, the biological sample is selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow. In one embodiment, the biological sample is enriched for the presence of hyperproliferative cells to at least 75% of the total population of cells. In another embodiment, the enrichment is performed according to at least one technique selected from the group consisting of needle microdissection, laser microdissection, fluorescence activated cell sorting, and immunological cell sorting. In still another embodiment, an automated machine performs the at least one technique to thereby transform the biological sample into a purified form enriched for the presence of hyperproliferative cells. IN yet another embodiment, the biological sample is obtained before the subject has received adjuvant chemotherapy. Alternatively, the biological sample is obtained after the subject has received adjuvant chemotherapy.

In yet another aspect, the control is determined from a non-cell hyperproliferative cell sample from the patient or member of the same species to which the patient belongs. In one embodiment, the control is determined from the average frequency of genomic locus appearance of chromosomal regions of the same ethnic group within the species to which the patient belongs. In another embodiment, the control is from non-cancerous tissue that is the same tissue type as said cancerous tissue of the subject. In still another embodiment, the control is from non-cancerous tissue that is not the same tissue type as said cancerous tissue of the subject.

In another aspect, AI is determined using major copy proportion (MCP). In one embodiment, AI for a given genomic region is counted when MCP is greater than 0.70.

In still another aspect, the plurality of chromosomal loci are randomly distributed throughout the genome at least every 100 Kb of DNA. In one embodiment, the plurality of chromosomal loci comprise at least one chromosomal locus on each of the 23 human chromosome pairs. In another embodiment, the plurality of chromosomal loci comprise at least one chromosomal locus on each arm of each of the 23 human chromosome pairs. In still another embodiment, the plurality of chromosomal loci comprise at least one chromosomal locus on at least one telomere of each of the 23 human chromosome pairs. In yet another embodiment, the plurality of chromosomal loci comprise at least one chromosomal locus on each telomere of each of the 23 human chromosome pairs.

In yet another aspect, the chromosomal aberrations have a minimum segment size of at least 1 Mb. In one embodiment, the chromosomal aberrations have a minimum segment size of at least 12 Mb.

In another aspect, the plurality of chromosomal aberrations comprises at least 5 chromosomal aberrations. In one embodiment, the plurality of chromosomal aberrations comprises at least 13 chromosomal aberrations.

In still another aspect, the chromosomal loci are selected from the group consisting of single nucleotide polymorphisms (SNPs), restriction fragment length polymorphisms (RFLPs), and simple tandem repeats (STRs).

In yet another aspect, the chromosomal loci are analyzed using at least one technique selected from the group consisting of molecular inversion probe (MIP), single nucleotide polymorphism (SNP) array, in situ hybridization, Southern blotting, array comparative genomic hybridization (aCGH), and next-generation sequencing.

In another aspect, the outcome of treatment is measured by at least one criteria selected from the group consisting of survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In still another aspect, the method further comprises determining a suitable treatment regimen for the subject. In one embodiment, the suitable treatment regimen comprises at least one platinum-based chemotherapeutic agent when a plurality of genomic chromosomal aberrations is determined or does not comprise at least one platinum-based chemotherapeutic agent when no plurality of genomic chromosomal aberrations is determined.

The invention also provides an assay, such as an assay or a method for selecting therapy for a subject having cancer, the assay comprising: subjecting a biological sample comprising a cancer cell or nucleic acid from a cancer cell taken from the subject to telomeric allelic imbalance (tAI) analysis; detecting the number of telomeric allelic imbalance (NtAI) in the cancer cell or nucleic acid from the cancer cell, and selecting a platinum-comprising therapy for the subject when the NtAI is detected to be above a reference value based on the recognition that platinum-comprising therapy is effective in patients who have NtAI above the reference value; and selecting a non-platinum-comprising cancer therapy for the subject when the NtAI is detected to be below a reference value based on the recognition that platinum-comprising cancer therapy is not effective in patients who have the NtAI below a reference value, and optionally administering to the subject, such as a human subject, the selected therapy.

An assay or a method for selecting platinum-comprising therapy for a subject having cancer comprising: subjecting a biological sample taken from the subject to allelic imbalance (AI) analysis; detecting the number of AI; and selecting platinum-comprising cancer therapy for the subject when the number of AIs is above a reference value based on the recognition that platinum-comprising cancer therapy is effective in patients who have the number of AIs is above a reference value, and optionally administering the platinum-comprising cancer therapy if it is selected.

The assays may optionally comprise the steps of obtaining a sample comprising cancer cells or cancer cell-derived DNA from the subject, subjecting the sample to manipulations, such as purification, DNA amplification, contacting the sample with a probe, labeling and other such steps that are needed in analysis of the NtAI or NAI. Moreover, the assaying and analysis may be performed by a non-human machine executing an algorithm and determining automatically whether the sample comprises the conditions to select a platinum-comprising cancer therapy or non-platinum comprising cancer therapy to the subject based on the analysis of NAI or NtAI.

The cancer may be any cancer. In some aspects of all the embodiments of the invention, the cancer is selected from breast and ovarian cancers. In some aspects of all the embodiments of the invention, the subject is negative for the well-known BRCA1 and/or BRCA2 mutations. In some aspects of all the embodiments, the subject has decrease or increase in BRCA1 and/or BRCA2 mRNA, which may be optionally determined together with the assay or before or after performing the assay, and which may further assist in determining whether the cancer will be responsive or resistant to treatment with platinum-comprising cancer therapy.

We also provide a method for predicting the outcome of anti-cancer treatment of a subject with a cell hyperproliferative disorder, comprising determining a global chromosomal aberration score (GCAS), comprising obtaining a biological sample from the subject and determining whether a plurality of chromosomal regions displaying a chromosomal aberration exists within a plurality of chromosomal loci, wherein said chromosomal aberrations are selected from the group consisting of allelic imbalance (NAI), loss of heterozygosity (NLOH), copy number aberrations (NCNA), copy number gain (NCNG), copy number decrease (NCND) and combinations thereof, relative to a control, and wherein the presence of a plurality of chromosomal regions displaying said chromosomal aberrations predicts the outcome of anti-cancer treatment of the subject.

We also provide a method for predicting the outcome of anti-cancer treatment of a subject with a cell hyperproliferative disorder, comprising determining a global chromosomal aberration score (GCAS), comprising obtaining a biological sample from the subject and determining whether a plurality of chromosomal regions displaying a chromosomal aberration exists within a plurality of chromosomal loci, wherein said chromosomal aberrations are selected from the group consisting of allelic imbalance (NAI), loss of heterozygosity (NLOH), copy number aberrations (NCNA), copy number gain (NCNG), copy number decrease (NCND) and combinations thereof, relative to a control, and wherein the presence of a plurality of chromosomal regions displaying said chromosomal aberrations predicts the outcome of anti-cancer treatment of the subject.

We further provide a method of determining prognosis in a patient comprising: (a) determining whether the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) (1) determining, based at least in part on the presence of the LOH signature, that the patient has a relatively good prognosis, or (b)(2) determining, based at least in part on the absence of the LOH signature, that the patient has a relatively poor prognosis We provide a composition comprising a therapeutic agent selected from the group consisting of DNA damaging agent, anthracycline, topoisomerase I inhibitor, and PARP inhibitor for use in treating a cancer selected from the group consisting of breast cancer, ovarian cancer, liver cancer, esophageal cancer, lung cancer, head and neck cancer, prostate cancer, colon cancer, rectal cancer, colorectal cancer, and pancreatic cancer in a patient with more than a reference number of LOH regions in at least one pair of human chromosomes of a cancer cell of the patient that are longer than a first length but shorter than the length of the whole chromosome containing the LOH region, wherein the at least one pair of human chromosomes is not a human X/Y sex chromosome pair, wherein the first length is about 1.5 or more megabases.

We further provide a method of treating cancer in a patient, comprising: (a) determining in a sample from said patient the number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases; (b) providing a test value derived from the number of said LOH regions; (c) comparing said test value to one or more reference values derived from the number of said LOH regions in a reference population (e.g., mean, median, terciles, quartiles, quintiles, etc.); and (d) administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or (e) recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value.

The method of claim 33, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, and/or said PARP inhibitor is iniparib, olaparib or velapirib.

We provide a composition comprising a therapeutic agent selected from the group consisting of platinum comprising cancer therapy and anthracycline for use in treating a cancer selected from the group consisting of breast cancer, ovarian cancer, liver cancer, esophageal cancer, lung cancer, head and neck cancer, prostate cancer, colon cancer, rectal cancer, colorectal cancer, and pancreatic cancer in a patient with increased allelic imbalance.

We provide a method for predicting the outcome of anti-cancer treatment of a subject with a cell hyperproliferative disorder, comprising determining a global chromosomal aberration score (GCAS), comprising obtaining a biological sample from the subject and determining whether a plurality of chromosomal regions displaying a chromosomal aberration exists within a plurality of chromosomal loci, wherein said chromosomal aberrations are selected from the group consisting of allelic imbalance (NAI), loss of heterozygosity (NLOH), copy number aberrations (NCNA), copy number gain (NCNG), copy number decrease (NCND) and combinations thereof, relative to a control, and wherein the presence of a plurality of chromosomal regions displaying said chromosomal aberrations predicts the outcome of anti-cancer treatment of the subject. In some aspects of all the embodiments of the invention, the anti-cancer treatment is chemotherapy treatment, which may also be platinum-based chemotherapeutic agents, for example, cisplatin, carboplatin, oxaliplatin, nedaplatin, and iproplatin.

In some aspects of all the embodiments of the invention, the cell hyperproliferative disorder can be selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, colon cancer, melanoma, and vagina.

The biological sample can be selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow, wherein the sample comprises cancer cells.

In some aspect of all the embodiments of the invention, including the assays and methods, the cancer cells in the sample may be enriched using, for example, needle microdissection, laser microdissection, fluorescence activated cell sorting, and immunological cell sorting.

In some aspects of all the embodiments of the invention an automated machine performs the at least one technique to thereby transform the biological sample into a purified form enriched for the presence of hyperproliferative cells.

In some aspects of all the embodiments of the invention, the sample or biological sample is obtained before the subject has received adjuvant chemotherapy, or after the subject has received adjuvant chemotherapy.

In some aspects of all the embodiments of the invention, the control is determined from the average frequency of genomic locus appearance of chromosomal regions of the same ethnic group within the species to which the patient belongs. The control may also be from non-cancerous tissue that is the same tissue type as said cancerous tissue of the subject, or from non-cancerous tissue that is not the same tissue type as said cancerous tissue of the subject.

BRIEF DESCRIPTION OF THE DRAWINGS

FIG. 1A shows a dose response curves of six TNBC cell lines as determined by a proliferation assay after 48 hours of cisplatin exposure. Curves for cells with lower 1050 values (greater sensitivity) are shown in blue; the cell line with highest 1050 (greatest resistance) is shown in red; cell lines with intermediate sensitivity are shown in grey. FIG. 1B shows the effect of the AI segment size threshold on the correlation between the number of telomeric AI regions and the cisplatin sensitivity in the six cell lines. Each point represent an $R^2$ value based on linear regression between the count of CNA regions of a minimum size indicated at X-axis, and cisplatin IC$_{50}$ in a panel of 6 TNBC cell lines (BT20, BT-549, HCC1187, HCC38, MDA-MB-231, MDA-MB-468). The optimum minimum segment size threshold is indicated by the dotted line. FIG. 1C shows a comparison between the number of telomeric AI regions (NtAI,12) and cisplatin sensitivity at the selected optimum threshold of 12 Mb. The cell lines are indicated as follows: 1, BT-20; 2, BT-549; 3, HCC1187; 4, HCC38; 5, MDA-MB-231; 6, MDA-MB-468.

FIG. 2 shows that major copy proportion (MCP) analysis identifies allelic imbalance in tumor biopsy samples with different degrees of tumor cell purity. FIG. 2 shows the formula for calculation of MCP, as well as normal bi-allelic chromosomes and three different ways in which allelic imbalance of a chromosomal region may occur and the corresponding MCP calculation. We also prepared diagrams depicting the display of loss of heterozygosity (LOH), AI determined by MCP, and absolute copy number analysis in two tumor samples with different degrees of normal cell contamination: T7 with >95% tumor cell content and T5 with approximately 80% tumor content. The chromosomes are indicated along the left side. The first columns for each tumor show the cells for LOH (blue) and retention of heterozygosity (yellow) at each chromosome position. The second columns show the MCP levels (between 0.5 and 1.0) at each chromosomal position. The MCP cut off of 0.7 is indicated by red lines. AI is called for regions with MCP greater than 0.7. The third and forth columns display the absolute DNA copy number at each position with white indicating diploid, shades of red indicating copy gain and shades of blue indicating copy loss. The copy number levels are shown in the far right panels. The tumor sample with greater purity (T7) shows agreement between LOH and MCP-determined AI calls. In the tumor sample with only 80% tumor cells, the LOH signal is lost, but AI can still be estimated by MCP with a 0.70 threshold.

FIG. 3A shows cisplatin IC50 versus number of telomeric AI regions at least 1 Mb long with AI defined by MCP>0.7. FIG. 3B shows cisplatin IC50 versus count of regions with copy number aberration, including gains and losses, at least 1 Mb long. FIG. 3C shows cisplatin IC50 versus count of regions with copy number gain, at least 1 Mb long. FIG. 3D shows cisplatin IC50 versus count of regions with copy number loss, at least 1 Mb long. The cell lines are indicated on each figure and are the same as in FIG. 1.

FIG. 4A shows cisplatin IC50 versus number of telomeric AI regions at least 1 Mb long with AI defined by MCP>0.7. FIG. 4B shows cisplatin IC50 versus number of interstitial AI regions at least 1 Mb long with AI defined by MCP>0.7. The cell lines are indicated on each figure and are the same as in FIG. 1.

FIGS. 5A-5F show the association between enumerated copy number aberrations (CNA) and sensitivity to cisplatin in vitro. FIGS. 5A-5C show the determination of the minimum segment size that demonstrates the best correlation to cisplatin sensitivity for number of copy number aberrations (NCNA; FIG. 5A), number of regions with copy number gain (NCNA, gain; FIG. 5B), and number of regions with copy number loss (NCNA, loss; FIG. 5C). Each point represent an R2 value based on linear regression between the count of CNA regions of a minimum size indicated at X-axis, and cisplatin IC50 in a panel of 6 TNBC cell lines (BT20, BT-549, HCC1187, HCC38, MDA-MB-231, MDA-MB-468). The optimal minimum size of CNA regions is indicated by the dotted line. FIG. 5D-5F show plots of the cisplatin IC50 values (µM, X-axis) vs. the number of CNA regions with optimum minimum segment sizes (Y-axis) as follows: NCNA at least 9 Mb long (FIG. 5D), NCNA, gain at least 9 Mb long (FIG. 5E), and NCNA, loss at least 5 Mb long, in 6 TNBC cell lines (FIG. 5F), as indicated.

FIG. 6A shows representations of individual tumor genomes arranged in order of increasing MP score. Regions of telomeric AI (dark blue) and interstitial AI (light blue) are indicated, with thin white lines demarcating individual chromosomes. FIG. 6B shows association between the MP score and the NtAI,12. FIG. 6C shows a receiver operating characteristics (ROC) curve evaluating the performance of NtAI, 12 to predict pCR to cisplatin therapy (pCR, n=4; no pCR, n=20).

FIG. 8A shows a rank of individuals according to increasing NtAI,12. Those who relapsed within one year are indicated by closed circles and those without relapse within one year are indicated by open circles. A cutoff value of NtAI,12=13, based on the TNBC ROC analysis for prediction of pathologic complete response (pCR) to cisplatin, is indicated by the dotted line. FIG. 8B shows Kaplan-Meier survival curves for time to relapse in individuals classified as high NtAI,12 (13 or greater NtAI,12 regions, blue) or low NtAI, 12 (fewer than 13 NtAI,12 regions, red).

FIG. 10A shows IC$_{50}$ values for each of the 10 cell lines. A proliferation assay was used to assess viability after 48 hours of cisplatin exposure and IC$_{50}$ was determined from the dose response curves. FIG. 10B shows comparison between number of regions with telomeric allelic imbalance (NtAI) and cisplatin sensitivity. Breast cancer subtype is indicated as follows: TN, red; HER2+, green, ER+HER2−, blue. FIG. 10C shows comparison between (NtAI) and cisplatin sensitivity as determined by GI50 in breast cancer cell lines from Heiser et al. (18). Reported transcriptional subtype is indicated as follows: basal, red; claudin-low, pink; ERBB2Amp, green; luminal, blue.

FIG. 11A and FIG. 11C show box plots showing NtAI distribution in cisplatin resistant and sensitive tumors. FIG. 11B and FIG. 11D show Receiver operating characteristic curves showing the ability of NtAI to predict for sensitivity to cisplatin.

FIG. 14A shows BRCA1 expression measured by qPCR is significantly lower in sensitive tumors in the Cisplatin-2 cohort. FIG. 14B shows BRCA1 expression is lower in samples that show methylation of the BRCA1 promoter region in the combined Cisplatin-1 and Cisplatin-2 cohorts. FIG. 14C shows BRCA1 expression measured by qPCR shows a negative correlation with NtAI in the combined Cisplatin-1 and Cisplatin-2 cohorts.

FIGS. 15A-15D show a model relating DNA repair to accumulation of telomeric AI and response to platinum agents. FIG. 15A shows in DNA repair-competent cells, DNA breaks are repaired using error-free homologous recombination employing the identical sister chromatid as a template, resulting in no AI. FIG. 15B and FIG. 15C show compromised DNA repair favors the use of error-prone repair pathways, resulting in chromosome rearrangements and aberrant radial chromosome formation. After mitotic division, daughter cells will have imbalance in the parental contribution of telomeric segments of chromosomes (telomeric AI). FIG. 15B shows non-homologous end joining is one error-prone mechanism that joins a broken chromatid of one chromosome (dark blue) to the chromatid of another, usually non-homologous, chromosome (white). Mitotic segregation results in cells with telomeric AI due to monoallelic change in DNA copy number of the affected telomeric region. FIG. 15C shows mitotic recombination may result in rearrangements between homologous chromosomes (dark blue and light blue). Mitotic segregation results in cells with AI due to copy neutral LOH. Break-induced replication would be expected to result in a similar outcome. FIG. 15D shows the same compromise in DNA repair that causes telomeric AI may also result in the inability of the tumor cell to repair drug-induced DNA damage, leading to tumor sensitivity to drugs such as platinum salts.

FIGS. 17A-17C show association between cisplatin sensitivity and measures of genomic abnormalities in a panel of breast cancer cell lines. Cisplatin $IC_{50}$ versus: FIG. 17A, total number of AI regions; FIG. 17B, total number of copy number gain regions; and FIG. 17C, total number of copy number loss regions. Numbers represents the same cell lines as in FIG. 1.

FIGS. 18A-18E show association between cisplatin sensitivity and telomeric/interstitial gains and losses. Cisplatin $IC_{50}$ versus: FIG. 18A, the number of telomeric copy number gain regions; FIG. 18B, the number of telomeric copy number loss regions; FIG. 18C, the number of interstitial copy number gain regions; FIG. 18D, the number of interstitial copy number loss regions; and FIG. 18E, NtAI score. Numbers represents the same cell lines as in FIG. 10 (1).

FIG. 21A shows identification of the optimum cut-off for NtAI (black) and BRCA1 mRNA (blue) to predict cisplatin response separately. Filled circles represent optimum cut-points. FIG. 21B shows how the combination of BRCA1 expression and NtAI may improve prediction of cisplatin response. Red indicates samples sensitive to cisplatin. Lines represents the optimum cut-off for prediction of response based on NtAI and BRCA1 mRNA, as determined in FIG. 21A. "Sens" represents the number of sensitive per total cases shown in each quadrant defined by the NtAI and BRCA1 mRNA cut-offs. The table shows the prediction accuracy based on the defined cut-offs for NtAI alone, BRCA1 mRNA alone, and the two measurements combined. ACC: accuracy. PPV: positive predictive value. NPV: negative predictive value. SENS: sensitivity. SPEC: specificity. P: p-value based on Fishers exact test. This table is based only on the samples shown in FIG. 21B.

FIGS. 22A-22C show BRCA1 expression by gene expression micro array in TCGA cohorts. FIG. 22A. BRCA1 mRNA expression versus NtAI in the TCGA ER-/HER2- breast cancers (n=78). FIG. 22B shows BRCA1 mRNA expression versus NtAI in the TCGA wtBRCA serous ovarian cancers (n=165). FIG. 22C shows BRCA1 mRNA expression versus treatment response in the TCGA wtBRCA serous ovarian cancers.

DETAILED DESCRIPTION OF THE INVENTION

Figure 1C:
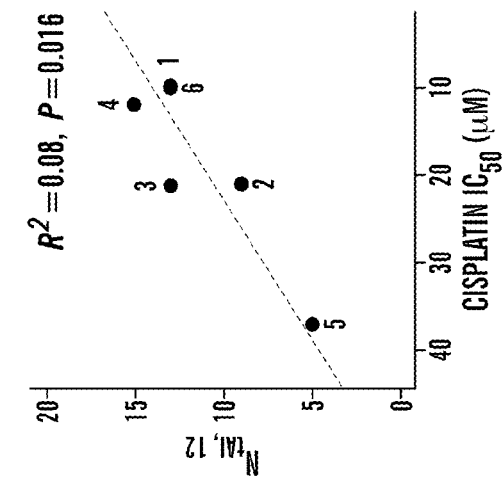
FIGS. 1A-1C show the correlation between allelic imbalance (AI) regions and cisplatin sensitivity in vitro.

The present invention relates to methods for predicting response of a cancer in a subject to anti-cancer therapies based upon a determination and analysis of a chromosomal aberration score, such as the number of allelic imbalance or the number of telomeric allelic imbalance in the chromosomes of the human genome.

According to one aspect of the invention, Global Chromosomal Aberration Score (GCAS) is a measurement predictive of responsiveness to anti-cancer therapies of a cancer in a subject. This utility of GCAS is based upon the novel finding that the summation of individual chromosomal aberrations can predict responsiveness of a cancer in a subject to anti-cancer agents independently of identifying specific chromosomal aberrations. Informative loci of interest (e.g., single nucleotide polymorphisms (SNPs), restriction fragment length polymorphisms (RFLPs), simple tandem repeats (STRs), etc.), are used to determine GCAS as they are useful for detecting and/or distinguishing chromosomal aberrations. As used herein, "chromosomal aberration" means allelic imbalance (AI), loss of heterozygosity (LOH), copy number aberrations (CNA), copy number gain (CNG), copy number decrease (CND) and combinations thereof. GCAS is a type of chromosomal aberration score, of which other types include telomeric aberration score, telomeric allelic imbalance score, etc. Thus, unless explicitly stated otherwise or unless the context clearly indicates otherwise, references to GCAS may apply in some embodiments equally to other chromosomal aberration scores (e.g., telomeric aberration score, telomeric allelic imbalance score, etc.).

GCAS is determined by determining a plurality or the total number of chromosome regions displaying allelic imbalance (NAI), loss of heterozygosity (LOH), copy number aberrations (NCNA), copy number gain (NCNG), and/or copy number decrease (NCND), as described further herein and according to methods well-known in the art. A GCAS of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more is predictive of response to anti-cancer therapy of the cancer cell from which the assayed nucleic acid was derived.

In one embodiment, the analysis is based upon nucleic acids obtained from a subject and/or control sample. Such samples can include "body fluids," which refer to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow.

In one embodiment, SNPs are used in determining GCAS, for predicting responsiveness of a cancer to an anti-cancer therapy. There are six possible SNP types, either transitions (A<>T or G<>C) or transversions (A<>G, A<>C, G<>T or C<>T). SNPs are advantageous in that large numbers can be identified.

In some embodiments, the SNPs or other genomic loci can be scored to detect copy number abnormalities. In such cases, such genomic loci do not need to be informative in terms of genotype since copy number is determined by hybridization intensities and doesn't depend on the genotype. Also, copy number abnormalities can be detected using methods that do not use SNPs, such as, for example, array CGH using BAC, cDNA and/or oligonucleotide arrays; microsatellite markers; STRs, RFLPS; etc.

For example, methods for evaluating copy number of nucleic acid in a sample include, but are not limited to, hybridization-based assays. One method for evaluating the copy number of encoding nucleic acid in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal mRNA (e.g., a non-amplified portion of the same or related cell, tissue, organ, etc.) provides an estimate of the relative copy number of the target nucleic acid. Similar methods for determining copy number can be performed using transcriptional arrays, which are well-known in the art.

An alternative means for determining the copy number is in situ hybridization (e.g., Angerer (1987) *Meth. Enzymol* 152:649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases.

In some applications it is necessary to block the hybridization capacity of repetitive sequences. Thus, in some embodiments, tRNA, human genomic DNA, or Cot-I DNA is used to block non-specific hybridization.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods of the invention are described, e.g., in Albertson (1984) *EMBO J.* 3: 1227-1234; Pinkel (1988) *Proc. Natl. Acad. Sci. USA* 85:9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20:207-211, or of Kallioniemi (1992) *Proc. Natl Acad Sci USA* 89:5321-5325 (1992) is used.

The methods of the invention are particularly well suited to array-based hybridization formats. Array-based CGH is described in U.S. Pat. No. 6,455,258, the contents of which are incorporated herein by reference. In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR anlaysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4:560, Landegren, et al. (1988) *Science* 241:1077, and Barringer et al. (1990) *Gene* 89:117), transcription amplification (Kwoh, et al. (1989) *Proc. Natl. Acad. Sci. USA* 86:1173), self-sustained sequence replication (Guatelli, et al. (1990) *Proc. Nat. Acad. Sci. USA* 87:1874), dot PCR, and linker adapter PCR, etc.

In still other embodiments of the methods provided herein, sequencing of individual nucleic molecules (or their amplification products) is performed, as an alternative to hybridization-based assays, using nucleic acid sequencing techniques. In one embodiment, a high throughput parallel sequencing technique that isolates single nucleic acid molecules of a population of nucleic acid molecules prior to sequencing may be used. Such strategies may use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380; U.S. Pat. Nos. 6,274,320; 6,258,568; 6,210,891), by HELISCOPE™ system from Helicos Biosciences (see, e.g., U.S. Patent App. Pub. No. 2007/0070349), and by others. Other sequencing strategies such as stochastic sequencing (e.g., as developed by Oxford Nanopore) may also be used, e.g., as described in International Application No. PCT/GB2009/001690 (pub. no. WO/2010/004273). All of the copy number determining strategies described herein can similarly be applied to any of other nucleic acid-based analysis described herein, such as for informative loci and the like described further below.

In other embodiments, SNPs can be scored for heterozygosity or absence of heterozygosity. Techniques like major copy proportion analysis utilize the allelic-imbalance and copy number information to extend the analyses that can be performed with copy number of LOH events alone since they can involve copy number deletion, neutral, or gain events. In other embodiments, to determine the GCAS of a cancer in a subject, heterozygous SNPs located throughout the genome are identified using nucleic acid samples derived from non-cancerous tissue of the subject or a population of subjects of a single species, and the number is determined of those heterozygous SNPs identified that maintain heterozygosity (or alternatively do not exhibit heterozygosity, i.e., have lost heterozygosity) in a nucleic acid sample of, or derived from, genomic DNA of cancerous tissue of the subject. A nucleic acid sample "derived from" genomic DNA includes but is not limited to pre-messenger RNA (containing introns), amplification products of genomic DNA or pre-messenger RNA, fragments of genomic DNA optionally with adapter oligonucleotides ligated thereto or present in cloning or other vectors, etc. (introns and non-coding regions should not be selectively removed).

All of the SNPs known to exhibit heterozygosity in the species to which the subject with cancer belongs need not be included in the number of heterozygous SNPs used or analyzed. In some embodiments, at least 45, 50, 75, 100, 125, 150, 175, 200, 225, 250, 275, 300, 350, 400, 450, 500, 550, 600, 650, 700, 750, 800, 850, 900, 950, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 50,000, 60,000, 70,000, 80,000, 90,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000 SNPs or more, or any range in between, or other informative loci of interest (e.g., RFLPs, STRs, etc.) are used. Preferably, such SNPs are in the human genome. In one embodiment, the plurality of heterozygous SNPs are randomly distributed throughout the genome at least every 1, 5, 10, 50, 100, 250, 500, 1,000, 1,500, 2,000, 2,500, 3,000, 5,000, 10,000 kb or more, or any range in between. By "randomly distributed," as used above, is meant that the SNPs of the plurality are not selected by bias toward any specific chromosomal locus or loci; however, other biases (e.g., the avoidance of repetitive DNA sequences) can be used in the selection of the SNPs. In other embodiments, the plurality of heterozygous SNPs are not randomly distributed throughout the genome (i.e., distributed within at least 250, 500, 1,000, 1,500, 2,000, 2,500, 3,000, 5,000, 10,000, 11,000, 12,000, 13,000, 14,000, 15,000, 16,000, 17,000, 18,000, 19,000, 20,000, 21,000, 22,000, 23,000, 24,000, or 25,000 kb=25 Mb). Such regions can further be biased, in some embodiments, to specific chromosomal regions such as telomeres (sometimes herein called "telomeric regions" or "telomeric segments") defined as regions extending toward the telomere but not crossing the centromere. In one embodiment, the telomeric allelic imbalance segment size is at least 1 Mb, 2 Mb, 3 Mb, 4 Mb, 5 Mb, 6 Mb, 7 Mb, 8 Mb, 9 Mb, 10 Mb, 11 Mb, 12 Mb, 13 Mb, 14 Mb, 15 Mb, 16 Mb, 17 Mb, 18 Mb, 19 Mb, 20 Mb, 21 Mb, 22 Mb, 23 Mb, 24 Mb, 25 Mb, or more, or any range in between, such as between 5 and 25 Mb. In another embodiment, the telomeric allelic imbalance segment size is 12 Mb. By contrast, interstitial regions do not involve the telomere. Interstitial regions are defined herein as regions of allelic imbalance that start downstream of the telomere meaning that there is at least some part of the chromosome with no allelic imbalance between the telomere and the region of allelic imbalance. In one embodiment, the plurality of heterozygous SNPs is not found in regions of genomic DNA that are repetitive. In another embodiment, the plurality of heterozygous SNPs comprises SNPs located in the genome on different chromosomal loci, wherein the different chromosomal loci comprise loci on each of the chromosomes of the species, or on each arm of each chromosome of the species (e.g., telomeric region thereof).

With many modern high-throughput techniques (including those discussed herein), it is possible to determine genotype, copy number, copy proportion, etc. for tens, hundreds, thousands, millions or even billions of genomic loci (e.g., all known heterozygous SNPs in a particular species, whole genome sequencing, etc.). Once a global assay has been performed (e.g., assaying all or substantially all known heterozygous SNPs), one may then informatically analyze one or more subsets of loci (i.e., panels of test loci or, as sometimes used herein, pluralities of test loci). Thus, in some embodiments, after assaying for allelic imbalance in hundreds of loci or more in a sample (or after receiving the data from such an assay) one may analyze (e.g., informatically) a panel or plurality of test loci according to the present invention (e.g., entirely or primarily telomeric SNPs) by combining the data relating to the individual test loci to obtain a test value indicative of the overall level, nature, etc. of allelic imbalance in the desired group of test loci.

Thus, in one aspect the invention provides a method of deriving a chromosomal aberration score (e.g., GCAS, telomeric aberration score, telomeric allelic imbalance score, etc.) comprising: determining whether a sample has a chromosomal aberration (e.g., of allelic imbalance, loss of heterozygosity, copy number aberrations, copy number gain, copy number decrease) at a plurality of assay (e.g., genomic) loci; analyzing a plurality of test loci within said plurality of assay loci for chromosomal aberrations; combining the data from (2) to derive a score reflecting the overall extent of chromosomal aberration in said plurality of test loci, thereby deriving a chromosomal aberration score.

In some embodiments determining whether a sample has a chromosomal aberration at the plurality of assay loci comprises assaying a tissue sample (e.g., physically processing a tangible patient specimen to derive data therefrom) and analyzing the data (e.g., SNP genotype data) derived from such assay. In some embodiments, determining whether a sample has a chromosomal aberration at the plurality of assay loci comprises analyzing data derived from an assay on a tissue sample.

In some embodiments the assay loci represent all loci analyzed in the relevant assay (e.g., all heterozygous SNPs represented on the particular SNP array, all nucleotides in a sequencing assay). In some embodiments the assay loci represent particular loci analyzed in the relevant assay (e.g., certain nucleotides, such as SNPs, in a sequencing assay). In some embodiments all assay loci are test loci. In some embodiments the test loci represent at least some percentage (e.g., 5%, 10%, 15%, 20%, 30%, 40%, 50%, 60%, 70%, 80%, 90%, 95% or 100%) of the assay loci. In some embodiments at least some percentage (e.g., 5%, 10%, 15%, 20%, 30%, 40%, 50%, 60%, 70%, 80%, 90%, 95% or 100%) of the assay loci are telomeric loci. In some embodiments at least some percentage (e.g., 5%, 10%, 15%, 20%, 30%, 40%, 50%, 60%, 70%, 80%, 90%, 95% or 100%) of the test loci are telomeric loci. Thus, in some embodiments the invention provides a method of deriving a chromosomal aberration score (e.g., GCAS, telomeric aberration score, telomeric allelic imbalance score, etc.) comprising: determining whether a sample has a chromosomal aberration (e.g., of allelic imbalance, loss of heterozygosity, copy number aberrations, copy number gain, copy number decrease) at a plurality of assay (e.g., genomic) loci; analyzing a plurality of test loci within said plurality of assay loci for chromosomal aberrations, wherein at least 5% (or 10%, or 15%, or 20%, or 30%, or 40%, or 50%, or 60%, or 70%, or 80%, or 90%, or 95%, or 100%) of the test loci are telomeric loci; combining the data from (2) to derive a score reflecting the overall extent of chromosomal aberration in said plurality of test loci, thereby deriving a chromosomal aberration score.

In some embodiments each test locus is assigned a particular weight in calculating the chromosomal aberration score. In some embodiments test loci are assigned a weight by each being given a particular coefficient in a formula (final or intermediate) used to calculate the chromosomal aberration score. In some embodiments telomeric test loci (all or at least 5%, 10%, 15%, 20%, 30%, 40%, 50%, 60%, 70%, 80%, 90%, 95% of telomeric test loci) are weighted such that they contribute at least some percentage (5%, 10%, 15%, 20%, 30%, 40%, 50%, 60%, 70%, 80%, 90%, 95% or 100%) to the chromosomal aberration score. Thus, in some embodiments the invention provides a method of deriving a chromosomal aberration score (e.g., GCAS, telomeric aberration score, telomeric allelic imbalance score, etc.) comprising: determining whether a sample has a chromosomal aberration (e.g., of allelic imbalance, loss of heterozygosity, copy number aberrations, copy number gain, copy number decrease) at a plurality of assay (e.g., genomic) loci; analyzing a plurality of test loci within said plurality of assay loci for chromosomal aberrations; combining the data from (2) to derive a score reflecting the overall extent of chromosomal aberration in said plurality of test loci, wherein each test locus is assigned a weighting coefficient that determines its contribution to the chromosomal aberration score and wherein telomeric loci are weighted such that they contribute at least 5% (or 10%, or 15%, or 20%, or 30%, or 40%, or 50%, or 60%, or 70%, or 80%, or 90%, or 95%, or 100%) to the chromosomal aberration score, thereby deriving a chromosomal aberration score.

"Telomeric locus" as used herein means a locus within a telomere or within some defined distance along the chromosome from the telomere. In some embodiments a telomeric locus is within 1 Kb, 2 Kb, 3 Kb, 4 Kb, 5 Kb, 6 Kb, 7 Kb, 8 Kb, 9 Kb, 10 Kb, 15 Kb, 20 Kb, 25 Kb, 30 Kb, 35 Kb, 40 Kb, 45 Kb, 50 Kb, 100 Kb, 200 Kb, 300 Kb, 400 Kb, 500 Kb, 750 Kb, 1 Mb, 2 Mb, 3 Mb, 4 Mb, 5 Mb, 6 Mb, 7 Mb, 8 Mb, 9 Mb, 10 Mb, 15 Mb, 20 Mb, 25 Mb, 30 Mb, 35 Mb, 40 Mb, 45 Mb, 50 Mb, 60 Mb, 70 Mb, 80 Mb, 90 Mb, or 100 Mb or less of the telomere. In some embodiments, the distance between the telomeric locus and the telomere is less than 1%, 2%, 3%, 4%, 5%, 10%, 15%, 20%, 30%, 40%, 50%, 60%, 70%, 80%, or 90% of the length of the entire chromosome arm.

Thus, in some embodiments a telomeric region or telomeric segment is a chromosomal region encompassing at least some number of telomeric loci (e.g., at least 1, 2, 3, 4, 5, 10, 15, 20, 25, 50, 75, 100, 150, 200, 250, 300, 400, 500, 750, 1,000, 1,500, 2,000, 2,500, 3,000, 4,000, 5,000, 7,500, or 10,000 or more telomeric loci). In some embodiments a telomeric region or telomeric segment is a chromosomal region encompassing at least 1, 2, 3, 4, 5, 10, 15, 20, 25, 50, 75, 100, 150, 200, 250, 300, 400, 500, 750, 1,000, 1,500, 2,000, 2,500, 3,000, 4,000, 5,000, 7,500, or 10,000 or more telomeric loci, wherein such telomeric loci are within 50 Kb, 100 Kb, 200 Kb, 300 Kb, 400 Kb, 500 Kb, 750 Kb, 1 Mb, 2 Mb, 3 Mb, 4 Mb, 5 Mb, 6 Mb, 7 Mb, 8 Mb, 9 Mb, or 10 Mb of the telomere (or any such combination of number of telomeric loci and distance of such loci from the telomere). In some embodiments telomeric regions do not cross the centromere.

DNA repair competency is one determinant of sensitivity to certain chemotherapy drugs, such as cisplatin. Cancer cells with intact DNA repair can avoid the accumulation of genome damage during growth and also can repair platinum-induced DNA damage. We sought genomic signatures indicative of defective DNA repair in cell lines and tumors, and correlated these signatures to platinum sensitivity. The number of sub-chromosomal regions with allelic imbalance extending to the telomere (NtAI) predicted cisplatin sensitivity in-vitro, and pathologic response to preoperative cisplatin treatment in patients with triple-negative breast cancer (TNBC). In serous ovarian cancer treated with platinum-based chemotherapy, higher NtAI forecast better initial response. We found an inverse relationship between BRCA1 expression and number of regions of tAI (NtAI) in sporadic TNBC and serous ovarian cancers without BRCA1 or BRCA2 mutation. Thus, accumulation of tAI is a marker of cisplatin sensitivity and suggests impaired DNA repair, and NtAI can be useful for predicting response to treatments targeting defective DNA repair.

Mutations in BRCA1 or BRCA2 cause defects in DNA repair that predict sensitivity to platinum salts in breast and ovarian cancer; however, some patients without BRCA mutations also benefit from these agents. This study shows that defects in DNA repair that cause platinum sensitivity can be inferred from the number of allelic imbalance (NAI), for example, the number of telomeric imbalance (NtAI), a measure of genomic aberration in tumors. We have demonstrated that NAI and/or NtAI can identify cancer patients without BRCA mutations who are likely to benefit from platinum-based therapy, such as cancer patients with triple negative breast cancer or triple negative ovarian cancer.

Cell lines carrying BRCA1 or BRCA2 mutations are more sensitive to killing by the platinum salts cisplatin and carboplatin than wild-type cells (Samouelian, et al. Chemosensitivity and radiosensitivity profiles of four new human epithelial ovarian cancer cell lines exhibiting genetic alterations in BRCA2, TGFbeta-RII, KRAS2, TP53 and/or CDNK2A. Cancer Chemother Pharmacol 2004; 54:497-504, Tassone, et al. BRCA1 expression modulates chemosensitivity of BRCA1-defective HCC1937 human breast cancer cells. Br J Cancer 2003; 88:1285-1291). Breast and ovarian cancers in patients carrying BRCA1 or BRCA2 mutations are likewise sensitive to platinum-based chemotherapy (Byrski, T., et al. Response to neoadjuvant therapy with cisplatin in BRCA1-positive breast cancer patients. Breast Cancer Res Treat 2009; 115:359-363, Cass, I., et al. Improved survival in women with BRCA-associated ovarian carcinoma. Cancer 2003; 97:2187-2195). The majority of breast cancers arising in women with a germline BRCA1 mutation lack expression of estrogen and progesterone receptors or amplification of the HER2-neu gene ("triple-negative"). BRCA1-related breast cancers share a number of phenotypic characteristics with sporadic triple-negative breast cancer (TNBC) (Turner, N. C., et al. BRCA1 dysfunction in sporadic basal-like breast cancer. Oncogene 2007; 26:2126-2132; Sorlie, T., et al. Repeated observation of breast tumor subtypes in independent gene expression data sets. Proc Natl Acad Sci USA 2003; 100:8418-8423; Lakhani, S. R., et al. Prediction of BRCA1 status in patients with breast cancer using estrogen receptor and basal phenotype. Clin Cancer Res 2005; 11:5175-5180). Both tumor types share a common pattern of genomic abnormalities and have high global levels of chromosomal aberrations including allelic imbalance (AI), the unequal contribution of maternal and paternal DNA sequences with or without changes in overall DNA copy number (Wang, Z. C., et al. Loss of heterozygosity and its correlation with expression profiles in subclasses of invasive breast cancers. Cancer Research 2004; 64: 64-71; Richardson, A. L., et al. X chromosomal abnormalities in basal-like human breast cancer. Cancer Cell 2006; 9:121-132; Van Loo, P., et al. Allele-specific copy number analysis of tumors. Proc Natl Acad Sci USA 2010; 107:16910-16915). Since they have in common genomic aberrations suggesting a shared lesion in genomic integrity control, it is reasonable to posit sporadic TNBC that has accumulated high levels of AI might share the sensitivity to platinum-based chemotherapy that characterizes BRCA1-associated cancer.

We performed a clinical trial, Cisplatin-1, in which 28 patients with operable TNBC were treated preoperatively with cisplatin monotherapy. Preoperative treatment in Cisplatin-1 resulted in greater than 90% tumor reduction in 10 of 28 (36%) patients, including pathologic complete response (pCR) in 6 women, 2 of whom had BRCA1- associated cancers (Silver, D. P., et al. Efficacy of neoadjuvant Cisplatin in triple-negative breast cancer. J Clin Oncol 2010; 28:1145-1153). A second trial, Cisplatin-2, accrued 51 patients with TNBC who received the same preoperative cisplatin regimen as Cisplatin-1, but in combination with the angiogenesis inhibitor bevacizumab (Ryan, P. D., et al. Neoadjuvant cisplatin and bevacizumab in triple negative breast cancer (TNBC): Safety and Efficacy. J Clin Oncol 2009; 27:551). Response rate in Cisplatin-2 were similar to Cisplatin-1. In the second trial, a greater than 90% tumor reduction was observed in 17 of 44 women (39%) completing treatment. In Cisplatin-2, 8 patients carried a germline BRCA1 or BRCA2 mutation, of which 4 patients achieved a pCR or near pCR to the cisplatin-bevacizumab regimen. In both trials, all patients had research sequencing to determine their germline BRCA1 and BRCA2 status. Thus in some aspects of all the embodiments of the invention, the BRCA1 and BRCA2 status can be determined either simultaneously with or before the allelic imbalance or telomeric allelic imbalance analysis. In some aspects, only patients without BRCA1 or BRCA2 mutations are subjected to the NAI (number of allelic imbalance) or NtAI (number of telomeric allelic imbalance) assays or analyses. Cisplatin was used as an example of platinum comprising cancer therapies.

We compared the number of various chromosomal abnormalities including AI present in tumor biopsies obtained before therapy to pathologically determined tumor response to cisplatin, alone or in combination with bevacizumab, assessed by examination of the post-treatment surgical specimen.

Without wishing to be bound by theory, chromosomal abnormalities such as regions of allelic imbalance, other than those resulting from whole chromosome gain or loss, can result from improper repair of DNA double-strand breaks during tumor development. If so, then a genome-wide count of abnormal chromosomal regions in tumors can indicate the degree of DNA repair incompetence, independent of knowledge of any specific causative DNA repair defect. We hypothesized that the number of chromosomal regions of AI in tumors would predict sensitivity to drugs that induce DNA crosslinks such as cisplatin.

We sought associations between various measures of sub-chromosomal abnormalities and sensitivity to cisplatin in breast cancer cell lines and found the most accurate predictor to be AI extending to the telomeric end of the chromosome (NtAI). Finally, we tested if NtAI was associated with treatment response in patient tumor samples in the Cisplatin-1 and Cisplatin-2 TNBC trials and in The Cancer Genome Atlas (TCGA) public data set of serous ovarian cancer, a cancer routinely treated with platinum-based therapy. In an effort to understand more about the processes leading to telomeric allelic imbalances, we mapped the location of their breakpoints and observed a striking association of these breakpoints with regions of the genome that are difficult to replicate, common copy number variants (CNVs). Further, a subset of high NtAI tumors display low BRCA1 mRNA levels. These observations begin to suggest models of how tAI may occur.

Figure 10A:
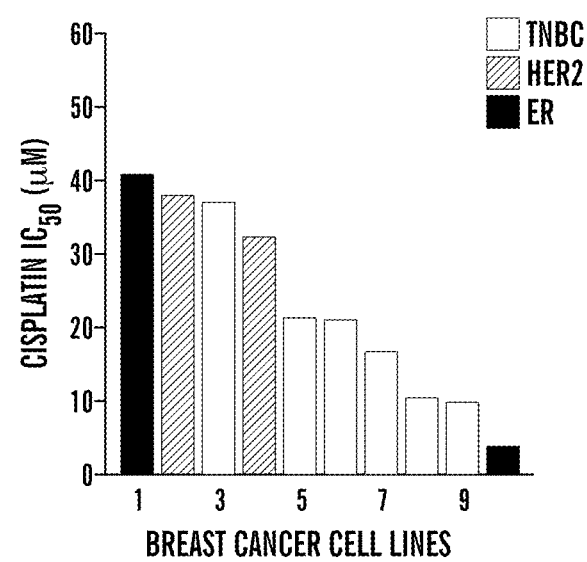
FIGS. 10A-10C show chromosomal aberrations and cisplatin sensitivity in vitro. The relationship between AI regions and cisplatin sensitivity was analyzed in 10 breast cancer cell lines: 1: CAMA-1, 2: HCC1954, 3:MDA-MB-231, 4: MDA-MB-361, 5: HCC1187, 6:BT-549,7: HCC1143, 8: MDA-MB-468, 9: BT-20, 10: T47D.

We showed that Cisplatin sensitivity correlates with burden, i.e. increase in the number of telomeric allelic imbalance compared to normal cells in, for example, breast cancer cell lines. We obtained single nucleotide polymorphism (SNP) genotype array data from the Wellcome Trust Sanger Institute for a set of established BRCA1 wild-type breast cancer cell lines for which we had determined cisplatin sensitivity (Li, Y., et al. Amplification of LAPTM4B and YWHAZ contributes to chemotherapy resistance and recurrence of breast cancer. Nat Med 2010; 16: 214-218) (FIG. 10A). Allele copy number was determined from the SNP array data and AI detected using ASCAT analysis (10) (FIG. 16), although any other allelic imbalance analysis can be used as well. We tested for association between the $IC_{50}$ values for cisplatin and each of three summary measures of chromosomal alteration: the number of chromosome regions with AI (NAI, FIG. 17A), the number of regions with copy number gains (NGain, FIG. 17B), and the number of regions with copy number loss (NLoss, FIG. 17C). None of these measures were correlated with cisplatin sensitivity in the cell lines.

Known defects in DNA double strand break repair, including loss of BRCA1, cause the spontaneous formation of triradial and quadriradial chromosome structures, which are cytologic indications of aberrant chromosome recombination (Silver, D. P., et al. Further evidence for BRCA1 communication with the inactive X chromosome. Cell 2007; 128:991-1002; Luo, G., et al. Cancer predisposition caused by elevated mitotic recombination in Bloom mice. Nat Genet 2000; 26:424-429; Xu, X., et al., Centrosome amplification and a defective G2-M cell cycle checkpoint induce genetic instability in BRCA1 exon 11 isoform-deficient cells. Mol Cell 1999; 3:389-395). The resolution of these chromosome rearrangements at mitosis can result in large regions of AI and/or copy number changes extending from the crossover to the telomere (Luo, G., et al. Cancer predisposition caused by elevated mitotic recombination in Bloom mice. Nat Genet 2000; 26:424-429; Vrieling, H. Mitotic maneuvers in the light. Nat Genet 2001; 28:101-102). More generally, several error-prone repair processes potentially employed by cells with defective DNA repair cause chromosome cross-over or copy choice events that result in allelic loss or copy number change extending from the site of DNA damage to the telomere.

Figure 1B:
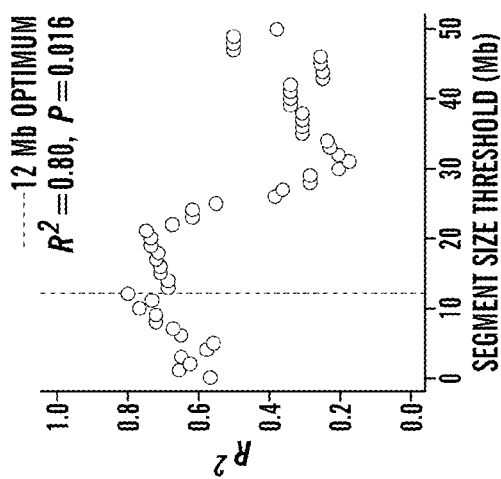
Figure 10B:
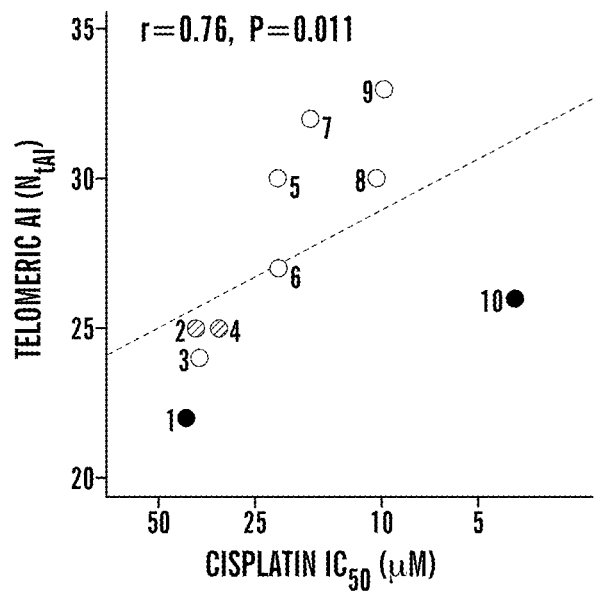
Figure 10C:
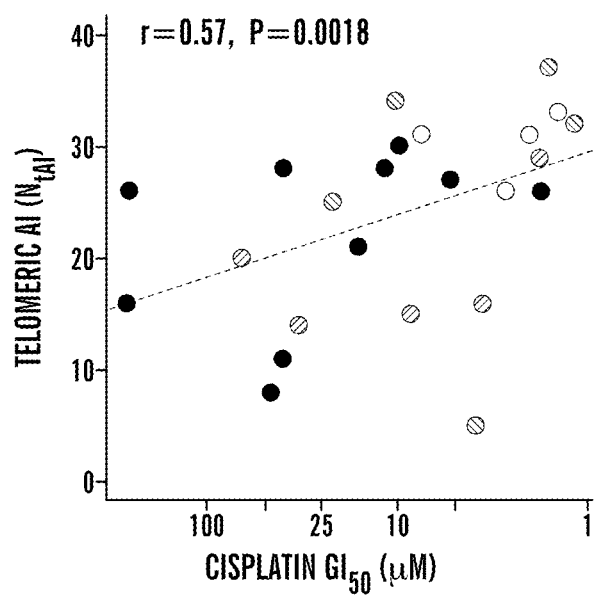
Figure 16:
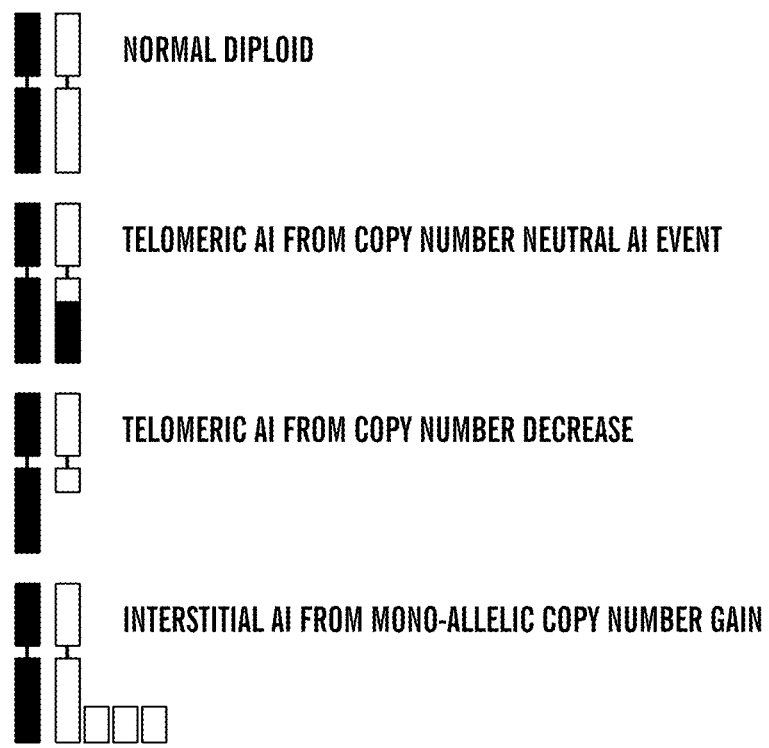
FIG. 16 shows an example definition of allelic imbalance. The diagram shows normal bi-allelic chromosomes and three different ways in which allelic imbalance of a chromosomal region may occur.

We looked for an association between cisplatin sensitivity and the number of contiguous regions of AI, copy gain, or copy loss that either extended to a telomere and did not cross the centromere (telomeric regions) or did not extend to a telomere (interstitial regions) (FIG. 16, FIG. 10B, and FIG. 18). The number of regions of telomeric AI (NtAI) was the only summary genomic measure that was significantly associated with cisplatin sensitivity in the breast cancer cell lines (r=0.76 P=0.011, FIG. 10B); the correlation between NtAI and cisplatin sensitivity was stronger when the analysis was restricted to the triple negative breast cancer lines (FIG. 1B, red circles; r=0.82 P=0.0499). A similar relationship was observed between NtAI and cisplatin sensitivity as measured by GI50 in a recently published study of breast cancer cell lines (r=0.57 P=0.0018, FIG. 10C) (18). Of all the drugs tested in this study, NtAI was most highly correlated to cisplatin sensitivity.

We showed that tumors sensitive to cisplatin-based chemotherapy have higher levels of telomeric allelic imbalance. We investigated whether the association between NtAI in clinical tumor samples and cisplatin sensitivity was present in the Cisplatin-1 trial. Sensitivity was measured by pathologic response determined after pre-operative treatment (Silver, D. P., et al. Efficacy of neoadjuvant Cisplatin in triple-negative breast cancer. J Clin Oncol 2010; 28:1145-1153). Molecular inversion probe SNP genotype data from pre-treatment tumor samples (n=27) were evaluated by ASCAT analysis to determine NtAI. We compared tumors with a reduction of at least 90% in the content of malignant cells (cisplatin sensitive) to tumors with limited or no response to cisplatin (cisplatin resistant, defined by tumor reduction of less than 90%).

Figure 11A:
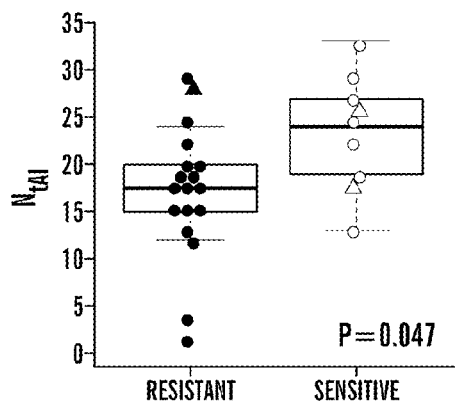
FIGS. 11A-11D show an NtAI and cisplatin response in breast cancer. In two clinical trials, TNBC patients were given preoperative cisplatin (Cisplatin-1, FIG. 11A-11B) or cisplatin and bevacizumab (Cisplatin-2, FIG. 11C-11D). Cisplatin sensitive tumors are indicated in red, cisplatin insensitive tumors are indicated in black. Tumors with germline mutations in BRCA1/2 are indicated with triangles.
Figure 11B:
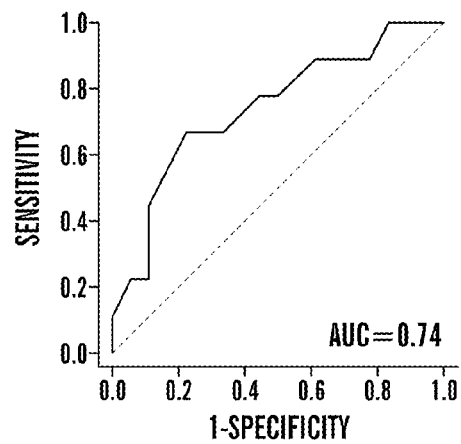

We showed that cisplatin sensitive tumors had significantly higher NtAI (median 24 versus 17.5, P=0.047, FIG. 11A). We tested the ability of NtAI to predict cisplatin response by calculating the area under the receiver operating characteristic (ROC) curve (AUC). ROC analysis showed that higher NtAI was associated with cisplatin sensitivity (AUC=0.74, CI 0.50-0.90, FIG. 11B).

Figure 11C:
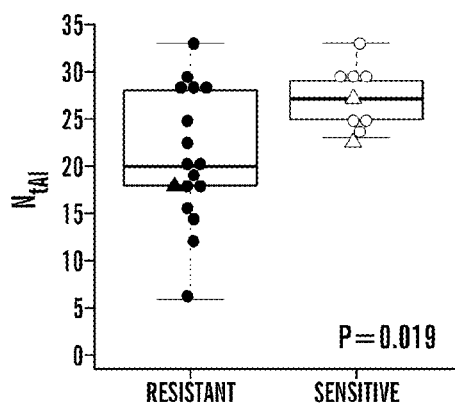
Figure 11D:
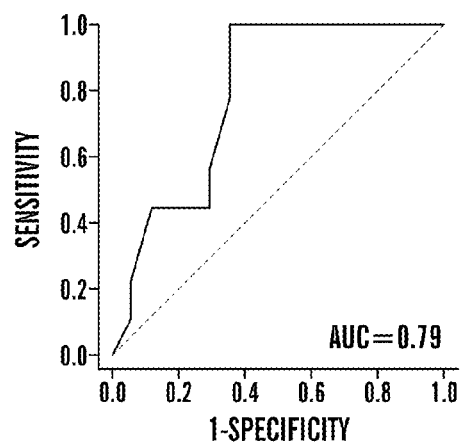

In the Cisplatin-2 trial, cisplatin sensitive tumors (n=9) had significantly higher NtAI than resistant tumors (n=17, median 27 versus 20, P=0.019, FIG. 11C). NtAI was also associated with response to cisplatin and bevacizumab by ROC analysis (AUC=0.79, CI 0.55-0.93, FIG. 11D). The association between NtAI and cisplatin sensitivity remained significant when cases with BRCA1 or BRCA2 mutation were excluded and only BRCA normal cases were analyzed (P=0.030 and P=0.023 in Cisplatin-1 and Cisplatin-2, respectively). Therefore, in two separate pre-operative trials in breast cancer, in which treatment sensitivity was assessed by a quantitative measure of pathologic response, NtAI reliably forecast the response to cisplatin-based treatment.

Figure 12:
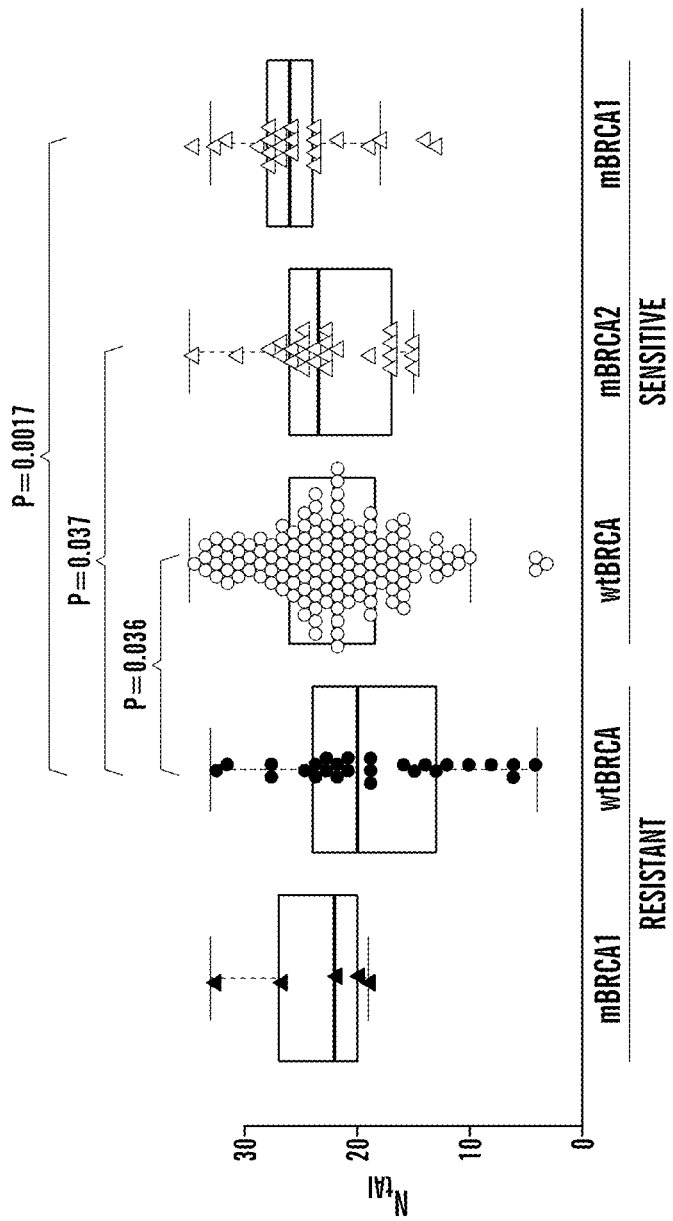
FIG. 12 shows NtAI and cisplatin response in serous ovarian cancer. Box plots showing NtAI distribution in platinum sensitive and resistant tumors in cancers without BRCA1 or BRCA2 mutations (wtBRCA) and for cancers with germline or somatic mutation in BRCA1 (mBRCA1) or in BRCA2 (mBRCA2). Red indicate sensitive samples, triangles indicate samples with germline or somatic mutations in BRCA1 or BRCA2. Significant differences between resistant wtBRCA and sensitive groups are indicated. In addition, significant differences were found between sensitive wtBRCA and sensitive mBRCA2 (P=0.047), and sensitive wtBRCA and sensitive mBRCA1 (P=0.014).
Figure 19:
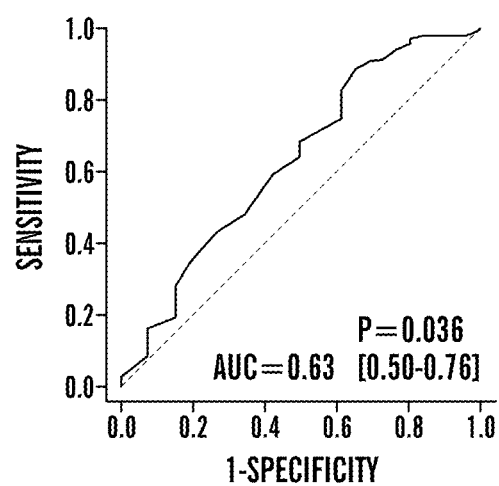
FIG. 19 shows receiver operating characteristic curve showing the ability of NtAI to predict for sensitivity to platinum-based therapy in wtBRCA serous ovarian cancer.

To test if the NtAI metric indicates platinum sensitivity in cancers other than breast, we determined the association between NtAI and initial treatment response in The Cancer Genome Atlas (TCGA) cohort of serous ovarian cancer patients that had received adjuvant platinum and taxane chemotherapy (Bell, D., et al., Integrated genomic analyses of ovarian carcinoma. Nature 2011; 474:609-615). Again, among the ovarian cancers without mutation in BRCA1 or BRCA2 (wtBRCA), the platinum sensitive tumors had significantly higher NtAI than platinum-resistant cancers (median 22 versus 20, P=0.036, FIG. 12), and were predictive of treatment response by ROC analysis (AUC=0.63, CI 0.50-0.76, FIG. 19). The ovarian cancers with somatic or germline mutation in BRCA1 or BRCA2 that were sensitive to platinum therapy had even higher NtAI (median=26, P=0.0017 and median 23.5, P=0.037 versus resistant wtBRCA, respectively, FIG. 12). All of the BRCA2 mutated cancers were platinum sensitive; however, 5 BRCA1 mutated tumors were resistant to platinum therapy yet appeared to have relatively high levels of NtAI. Thus high NtAI is characteristic of serous ovarian cancer with known mutation in either BRCA1 or BRCA2; high NtAI is also found in a subset of sporadic cancers without BRCA mutations where it is predictive of platinum sensitivity.

Accordingly, we provide a method for selecting therapy for a human cancer patient, the method comprising assaying a sample comprising tumor cells taken from the human cancer patient for the number of allelic imbalance, for example telomeric allelic imbalance, and selecting, and optionally administering a platinum-comprising cancer therapy to the human cancer patient if the number of allelic imbalance is increased compared to a reference value. The reference value for the number of allelic imbalance, such as telomeric allelic imbalance can be, for example, at least 20, at least 21, at least 22, at least 23, at least 23.5, at least 24, at least 25, at least 26, at least 27, at least 28 at least 29, or at least 30. The reference value can be determined for each tumor, for example from the number of allelic imbalance collected from similar cancers that are platinum-resistant. So, for example, in a lung cancer, samples from lung cancer cells from platinum-resistant cancers can provide a median number of allelic imbalance for the cancer to be used as a reference value for non-responding samples.

Figure 20:
FIG. 20 shows distribution of dsDNA breaks resulting in telomeric allelic imbalance and association with common CNVs according to cisplatin response. Squares indicate inferred chromosomal location of dsDNA breaks resulting in tAI, pooled from both trials. Stacked squares represent multiple tumors with dsDNA breaks at the same position.

We further showed that locations of NtAI-associated chromosomal breaks are not random. To understand the processes leading to tAI better, we mapped the location of the chromosome breakpoints defining the boundary of the tAI regions. We observed many breakpoints were located in very close proximity to each other (FIG. 20), suggesting a non-random distribution of DNA breaks causing telomeric allelic imbalance.

Without wishing to be bound by a theory, recurrent chromosomal translocation breakpoints can be associated with regions of repeated DNA sequence that can cause stalled replication forks, an increased frequency of DNA breaks, and subsequent rearrangement by non-allelic homologous recombination or other similar mechanisms (Kolomietz, E., et al., The role of Alu repeat clusters as mediators of recurrent chromosomal aberrations in tumors. Genes Chromosomes Cancer 2002; 35:97-112; Hastings, P. J., Ira, G., and Lupski, J. R. A microhomology-mediated break-induced replication model for the origin of human copy number variation. PLoS Genet 2009; 5: e1000327).

Figures 13A, 13B:
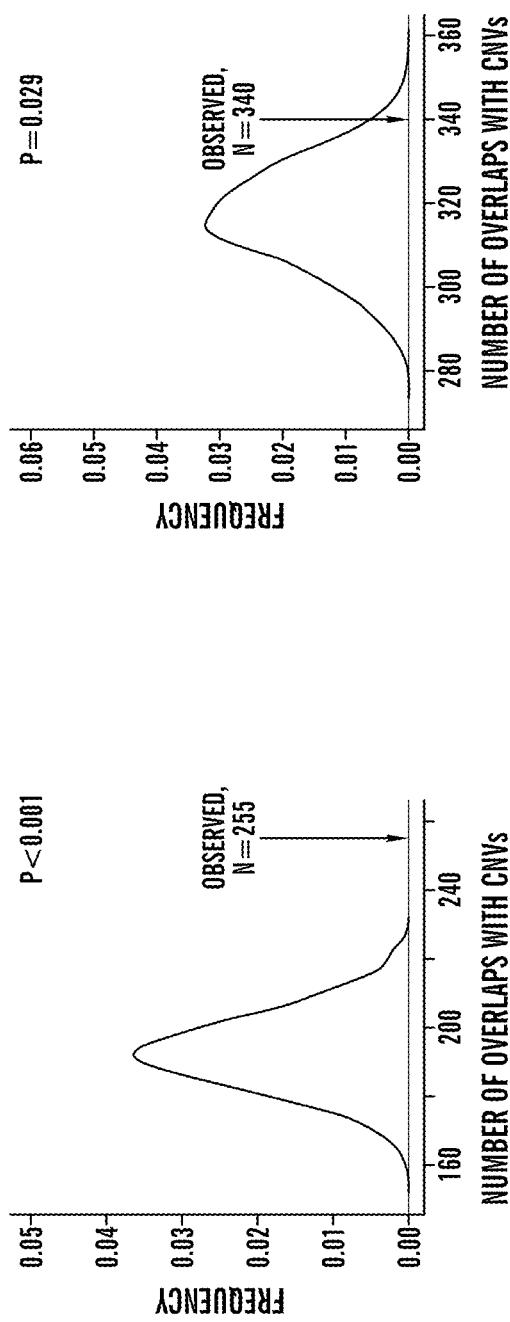
FIGS. 13A-13B show enrichment of common CNVs in tAI chromosomal breakpoints from TNBC. Association of tAI breakpoints with common CNV loci based on computational simulations that compared the expected number of breakpoints containing CNVs with the observed number in total cases in Cisplatin-1 (FIG. 13A) and Cisplatin-2 (FIG. 13B).

Copy number variants (CNVs) are highly homologous DNA sequences for which germline copy number varies between healthy individuals (Iafrate, A. J., et al. Detection of large-scale variation in the human genome. Nat Genet 2004; 36:949-951; Sebat, J., et al., Large-scale copy number polymorphism in the human genome. Science 2004; 305: 525-528). CNVs have been proposed to facilitate the generation of chromosomal alterations, similar to fragile sites (Hastings, P. J., Ira, G., and Lupski, J. R. A microhomology-mediated break-induced replication model for the origin of human copy number variation. PLoS Genet 2009; 5:e1000327; Stankiewicz, P., et al. Genome architecture catalyzes nonrecurrent chromosomal rearrangements. Am J Hum Genet 2003; 72:1101-1116; Hastings, P. J., et al., Mechanisms of change in gene copy number. Nat Rev Genet 2009; 10:551-564). We compared the number of observed breaks within 25 kB of a CNV to the frequency expected by chance alone, based on permuted data. In the Cisplatin-1 cohort, of 517 NtAI breakpoints, 255 (49%) were associated with overlapping CNVs. Similarly, in the cisplatin-2 cohort, out of 599 NtAI breakpoints, 340 (57%) were associated with CNVs. In both trials, the observed number of NtAI breaks associated with CNVs was significantly higher than expected by chance (FIG. 13A-13B). Thus many of the breakpoints leading to telomeric AI in TNBC occur near CNVs suggesting stalled replication forks, replication stress, or other CNV-associated mechanisms may be involved in the genesis of telomeric AI.

Accordingly, in some aspects of all the embodiments of the invention, we provide a method or an assay for determining whether a patient is responsive to platinum-comprising therapy by assaying the number of allelic imbalance, such as telomeric allelic imbalance, wherein the AI is associated with copy number vatiations (CNVs). If increase of CNV associates NAI, such as NtAI is detected, then determining that the patient is responsive to platinum-comprising cancer therapy and optionally administering the platinum-comprising therapy to the cancer patient. If no increase in CNV associated NAI, such as NtAI is detected, then determining that the cancer patient is not responsive to platinum comprising cancer therapy and optionally administering to the cancer patient a non-platinum comprising cancer therapy.

We demonstrated that low BRCA1 mRNA is associated with high NtAI and sensitivity to cisplatin.

According, in some aspects of all the embodiments of the invention, we provide an assay or a method for determining responsiveness of a cancer patient to a platinum-comprising cancer therapy, the assay or method comprising, assaying in a cancer-cell comprising sample taken from the cancer patient the number of allelic imbalance and/or the BRCA1 mRNA amount, and if the number of allelic imbalance is increased and/or the BRCA1 mRNA amount is decreased, then selecting, and optionally administering to the cancer patient platinum-comprising cancer therapy. If, on the other hand no increase in the number of allelic imbalance and/or no decrease in BRCA1 mRNA amount is detected, then selecting, and optionally administering to said cancer patient a non-platinum comprising cancer therapy.

Figure 14C:
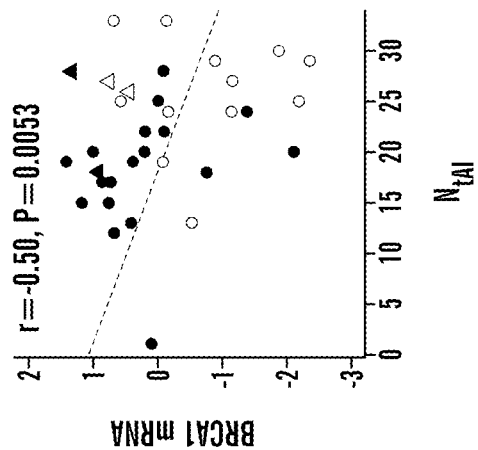
FIGS. 14A-14C show Association between BRCA1 expression, NtAI and BRCA1 promoter methylation. Red indicates tumors sensitive to cisplatin. Tumors with a germline mutation in BRCA1 or BRCA2 are excluded in FIGS. 14A. and 14B., but included in 14C., represented as triangles.
Figure 14B:
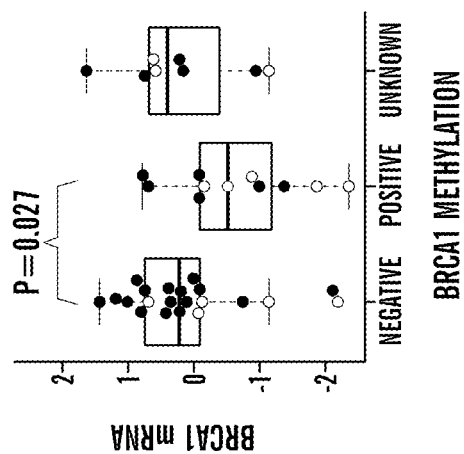
Figure 14A:
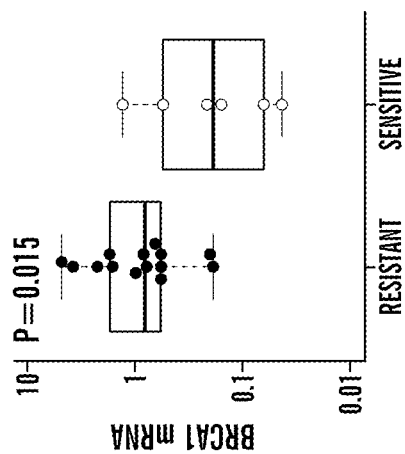

In our Cisplatin-1 trial, we found an association between low BRCA1 transcript levels and better response to cisplatin. In the Cisplatin-2 trial, BRCA1 transcript levels measured, for example, by qPCR are also associated with cisplatin response (P=0.015, FIG. 14A). In a combined analysis of data from both trials, lower BRCA1 transcript levels are associated with methylation of the BRCA1 promoter (P=0.027, FIG. 14B), though BRCA1 promoter methylation itself is not significantly associated with cisplatin response (P=0.25, Fishers exact test). BRCA1 mRNA levels are inversely associated with NtAI in the two cisplatin trials (r=−0.50, P=0.0053, FIG. 14C). This finding suggests that dysfunction of a BRCA1-dependent process or other abnormality causing low BRCA1 mRNA may be responsible for the high level of telomeric allelic imbalance and also cisplatin sensitivity in many of these TNBCs.

In some aspects of all the embodiments of the invention, the assays and methods comprise assaying the methylation status of BRCA1, wherein increase in methylation of BRCA1 promoter region is associated with a responsiveness to platinum-comprising cancer therapy and no increase in methylation of BRCA1 promoter region is associated with resistance to platinum-comprising cancer therapy. If increased methylation of BRCA1 promoter region is detected, then selecting, and optionally administering, a platinum-comprising therapy for the cancer patient, and if no increase in methylation of BRCA1 promoter region is detected, then selecting, and optionally administering a non-platinum comprising therapy for the cancer patient. In some aspects of this embodiment, the cancer is breast cancer.

Figure 21A:
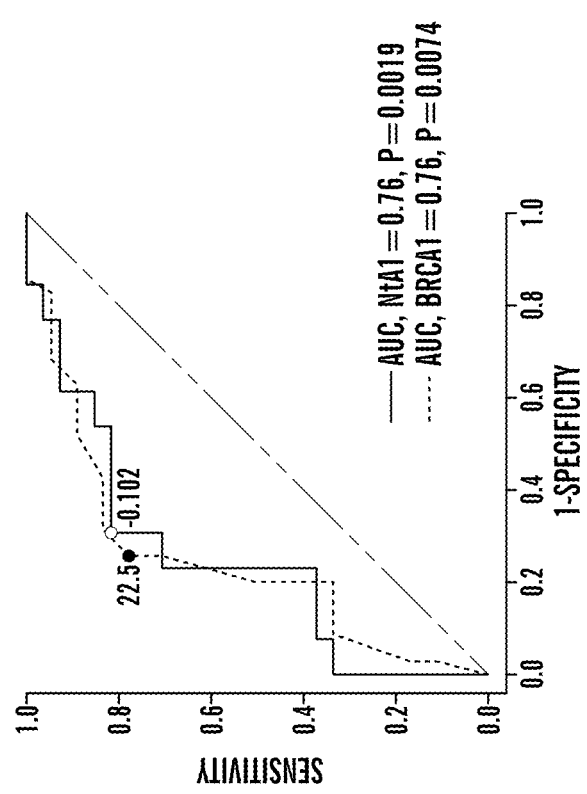
FIGS. 21A-21B show BRCA1 expression and NtAI versus response to cisplatin in Cisplatin-1 and Cisplatin-2 combined.
Figure 21B:
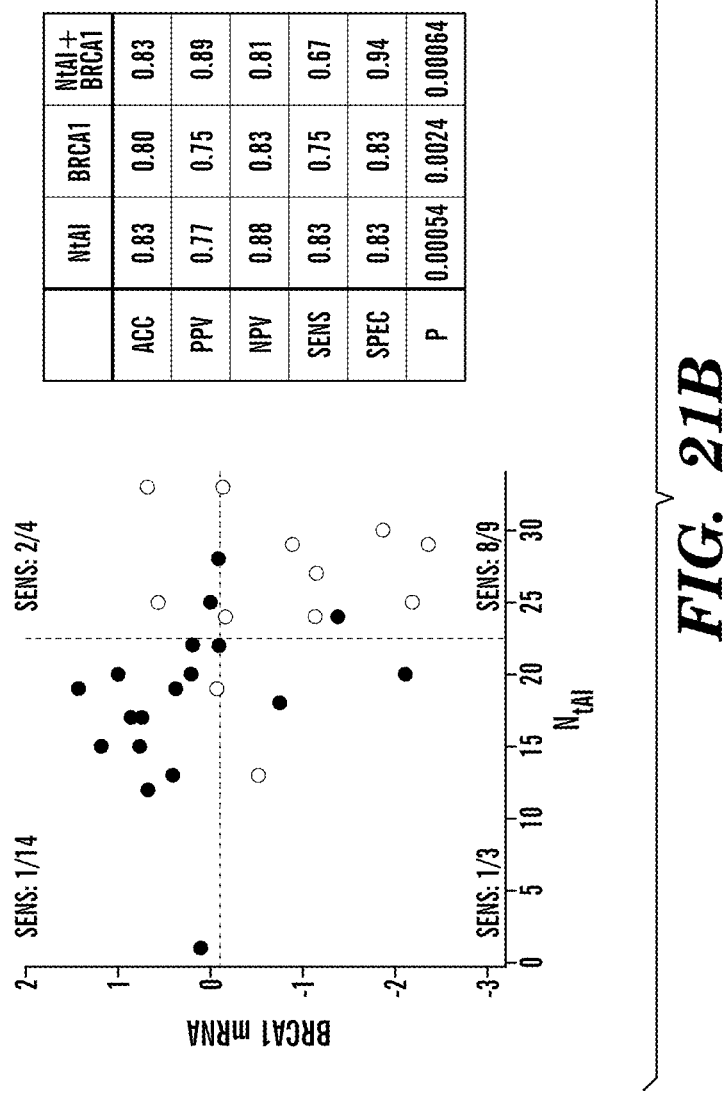

ROC analysis of the combined TNBC trials suggests that BRCA1 expression level or NtAI may give a similar predictive accuracy for cisplatin sensitivity (FIG. 21A). When high NtAI and low BRCA1 expression are combined in a predictive model, the positive predictive value and specificity of prediction improved considerably but the sensitivity was decreased relative to NtAI alone (FIG. 21B), suggesting that low BRCA1 expression does not account for all cisplatin sensitive tumors.

In the TNBC trials, we noted a few cisplatin sensitive tumors with high levels of NtAI but high BRCA1 mRNA, suggesting that alternative mechanisms may drive the generation of tAI in some tumors. Analysis of TCGA data of ER-/HER2-breast cancer and wtBRCA serous ovarian cancer demonstrate an inverse correlation between NtAI and BRCA1 expression. Yet in both cohorts there was a considerable subset of tumors with high NtAI and high BRCA1 expression (FIG. 22A, 22B). Unlike NtAI, BRCA1 expression was not apparently different between sensitive and resistant wtBRCA serous ovarian cancers (FIG. 22C). These findings suggest a model whereby high NtAI may represent a readout of DNA repair deficiency resulting from either low BRCA1 expression or from other known or unknown mechanisms (FIG. 15).

In some aspects of all the embodiments of the invention, the NtAI or NAI analysis is performed alone without separately detecting or determining the status of BRCA1 and/or BRCA2, such as whether the tumor cell carries a BRCA1 and/or BRCA2 mutation or whether the BRCA1 or BRCA2 expression is decreased or not, or whether the BRCA1 and/or BRCA2 promoter methylation is increased or not. In some aspects of all the embodiments of the invention, the NtAI or NAI analysis is performed in combination with detecting or determining the status of BRCA1 and/or BRCA2.

Several embodiments of the invention described herein involve a step of correlating an LOH signature or the number of AI or tAI according to the present invention (e.g., the total number of LOH/AI/tAI regions in at least one pair of human chromosomes of said cancer cell that are longer than a first length but shorter than the length of the whole chromosome containing the LOH/AI/tAI region, wherein said at least one pair of human chromosomes is not a human X/Y sex chromosome pair, wherein said first length is about 1.5 or more megabases) to a particular clinical feature (e.g., an increased likelihood of a deficiency in the BRCA1 or BRCA2 gene; an increased likelihood of HDR deficiency; an increased likelihood of response to a treatment regimen comprising a DNA damaging agent, an anthracycline, a topoisomerase I inhibitor, radiation, and/or a PARP inhibitor; etc.) if the number is greater than some reference (or optionally to another feature if the number is less than some reference). Throughout this document, wherever such an embodiment is described, another embodiment of the invention may involve, in addition to or instead of a correlating step, one or both of the following steps: (a) concluding that the patient has the clinical feature based at least in part on the presence or absence of the LOH signature or increase or not of the number of AI or tAI; or (b) communicating that the patient has the clinical feature based at least in part on the presence or absence of the LOH signature or increase of NAI or NtAI.

By way of illustration, but not limitation, one embodiment described in this document is a method of predicting a cancer patient's response to a cancer treatment regimen comprising a DNA damaging agent, an anthracycline, a topoisomerase I inhibitor, radiation, and/or a PARP inhibitor, said method comprising: (1) determining, in a cancer cell from said cancer patient, the number of LOH/AI/tAI regions in at least one pair of human chromosomes of a cancer cell of said cancer patient that are longer than a first length but shorter than the length of the whole chromosome containing the LOH/AI/tAI region, wherein said at least one pair of human chromosomes is not a human X/Y sex chromosome pair, wherein said first length is about 1.5 or more megabases; and (2) correlating said total number that is greater than a reference number with an increased likelihood that said cancer patient will respond to said cancer treatment regimen. According to the preceding paragraph, this description of this embodiment is understood to include a description of two related embodiments, i.e., a method of predicting a cancer patient's response to a cancer treatment regimen comprising a DNA damaging agent, an anthracycline, a topoisomerase I inhibitor, radiation, and/or a PARP inhibitor, said method comprising: (1) determining, in a cancer cell from said cancer patient, the number of LOH/AI/tAI regions in at least one pair of human chromosomes of a cancer cell of said cancer patient that are longer than a first length but shorter than the length of the whole chromosome containing the LOH/AI/tAI region, wherein said at least one pair of human chromosomes is not a human X/Y sex chromosome pair, wherein said first length is about 1.5 or more megabases; and (2)(a) concluding that said patient has an increased likelihood that said cancer patient will respond to said cancer treatment regimen based at least in part on a total number that is greater than a reference number; or (2)(b) communicating that said patient has an increased likelihood that said cancer patient will respond to said cancer treatment regimen based at least in part on a total number that is greater than a reference number.

In each embodiment described in this document involving correlating a particular assay or analysis output (e.g., total number of LOH/AI/tAI regions greater than a reference number, etc.) to some likelihood (e.g., increased, not increased, decreased, etc.) of some clinical feature (e.g., response to a particular treatment, cancer-specific death, etc.), or additionally or alternatively concluding or communicating such clinical feature based at least in part on such particular assay or analysis output, such correlating, concluding or communicating may comprise assigning a risk or likelihood of the clinical feature occurring based at least in part on the particular assay or analysis output. In some embodiments, such risk is a percentage probability of the event or outcome occurring. In some embodiments, the patient is assigned to a risk group (e.g., low risk, intermediate risk, high risk, etc.). In some embodiments "low risk" is any percentage probability below 5%, 10%, 15%, 20%, 25%, 30%, 35%, 40%, 45%, or 50%. In some embodiments "intermediate risk" is any percentage probability above 5%, 10%, 15%, 20%, 25%, 30%, 35%, 40%, 45%, or 50% and below 15%, 20%, 25%, 30%, 35%, 40%, 45%, 50%, 55%, 60%, 65%, 70%, or 75%. In some embodiments "high risk" is any percentage probability above 25%, 30%, 35%, 40%, 45%, 50%, 55%, 60%, 65%, 70%, 75%, 80%, 85%, 90%, 95%, or 99%.

As used herein, "communicating" a particular piece of information means to make such information known to another person or transfer such information to a thing (e.g., a computer). In some methods of the invention, a patient's prognosis or likelihood of response to a particular treatment is communicated. In some embodiments, the information used to arrive at such a prognosis or response prediction (e.g., LOH signature or NTAI or NtAI according to the present invention, etc.) is communicated. This communication may be auditory (e.g., verbal), visual (e.g., written), electronic (e.g., data transferred from one computer system to another), etc. In some embodiments, communicating a cancer classification (e.g., prognosis, likelihood of response, appropriate treatment, etc.) comprises generating a report that communicates the cancer classification. In some embodiments the report is a paper report, an auditory report, or an electronic record. In some embodiments the report is displayed and/or stored on a computing device (e.g., handheld device, desktop computer, smart device, website, etc.). In some embodiments the cancer classification is communicated to a physician (e.g., a report communicating the classification is provided to the physician). In some embodiments the cancer classification is communicated to a patient (e.g., a report communicating the classification is provided to the patient). Communicating a cancer classification can also be accomplished by transferring information (e.g., data) embodying the classification to a server computer and allowing an intermediary or end-user to access such information (e.g., by viewing the information as displayed from the server, by downloading the information in the form of one or more files transferred from the server to the intermediary or end-user's device, etc.).

Wherever an embodiment of the invention comprises concluding some fact (e.g., a patient's prognosis or a patient's likelihood of response to a particular treatment regimen), this may include in some embodiments a computer program concluding such fact, typically after performing an algorithm that applies information on LOH/AI/tAI regions according to the present invention.

In each embodiment described herein involving a number of LOH regions (e.g., LOH Indicator Regions) or a total combined length of such LOH regions, the present invention encompasses a related embodiment involving a test value or score (e.g., HRD score, LOH score, NAI, NtAI etc.) derived from, incorporating, and/or, at least to some degree, reflecting such number or length. In other words, the bare LOH/AI/tAI region numbers or lengths need not be used in the various methods, systems, etc. of the invention; a test value or score derived from such numbers or lengths may be used. For example, one embodiment of the invention provides a method of treating cancer in a patient, comprising: (1) determining in a sample from said patient the number of LOH/AI/tAI regions in at least one pair of human chromosomes of a cancer cell of the cancer patient that are longer than a first length but shorter than the length of the whole chromosome containing the LOH/AI/tAI region indicates that the cancer cells have the LOH signature or the number of AI or tAI, wherein the at least one pair of human chromosomes is not a human X/Y sex chromosome pair, wherein the first length is about 1.5 or more megabases; (2) providing a test value derived from the number of said LOH/AI/tAI regions; (3) comparing said test value to one or more reference values derived from the number of said LOH/AI/tAI regions in a reference population (e.g., mean, median, terciles, quartiles, quintiles, etc.); and (4)(a) administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or (4)(b) recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value. The invention encompasses, mutatis mutandis, corresponding embodiments where the test value or score is used to determine the patient's prognosis, the patient's likelihood of response to a particular treatment regimen, the patient's or patient's sample's likelihood of having a BRCA1, BRCA2, RAD51C or HDR deficiency, etc.

In one aspect, the invention provides a kit comprising, in a container, reagents suitable for determining allelic imbalance in at least 1, 2, 3, 4, 5, 10, 15, 20, 25, 50, 75, 100, 150, 200, 250, 300, 400, 500, 750, 1,000, 1,500, 2,000, 2,500, 3,000, 4,000, 5,000, 7,500, or 10,000 or more telomeric loci (e.g., loci within 50 Kb, 100 Kb, 200 Kb, 300 Kb, 400 Kb, 500 Kb, 750 Kb, 1 Mb, 2 Mb, 3 Mb, 4 Mb, 5 Mb, 6 Mb, 7 Mb, 8 Mb, 9 Mb, or 10 Mb of the telomere). In some embodiments the kit comprises reagents for determining allelic imbalance in no more than 10,000, 7,500, 5,000, 4,000, 3,000, 2,000, 1,000, 750, 500, 400, 300, 200, 150, 100, 90, 80, 70, 60, or 50 total loci. In some embodiments telomeric loci comprise at least 10%, 15%, 20%, 30%, 40%, 50%, 60%, 70%, 80%, 90%, 95%, 99%, or 100% of the loci for which the kit contains reagents for determining allelic imbalance.

As discussed above, allelic imbalance is a type of chromosomal aberration. As used herein, "allelic imbalance" means a change in the number and/or type of alleles of a chromosome in a somatic tissue as compared to germline. In some embodiments allelic imbalance is loss of heterozygosity ("LOH"). This can be copy number neutral, such as when one of the heterozygous parental alleles is lost and the other allele is duplicated as a "replacement." LOH can also occur in a non-copy number neutral way, where one parental allele is simply lost. In some embodiments allelic imbalance is duplication of one allele over another (somatic AA/B from AA/B germline) or greater duplication of one allele as compared to another (e.g., somatic AAAA/BB from A/B germline). In some embodiments a region has allelic imbalance if loci in that region show MCP (as discussed in greater detail in Section IV.H. below) of is greater than 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80. 0.81, 0.82, 0.83, 0.84, 0.85, 0.86, 0.87, 0.88, 0.89, 0.90, 0.91, 0.92, 0.92, 0.93, 0.94, 0.95, 0.96, 0.97, 0.98, or 0.99 (including MCP of 1).

Thus, a predefined number of chromosomes may be analyzed to determine the total number of Indicator LOH Regions, preferably the total number of LOH regions of a length of greater than 9 megabases, 10 megabases, 12 megabases, 14 megabases, more preferably greater than 15 megabases. Alternatively or in addition, the sizes of all identified Indicator LOH Regions may be summed up to obtain a total length of Indicator LOH Regions.

For classification of positive LOH signature status, the reference number discussed above for the total number of Indicator LOH Regions may be 5, 6, 7, 8, 9, 10, 11, 12, 13, 14, 15, 16, 18, 19, 20 or greater, preferably 5, preferably 8, more preferably 9 or 10, most preferably 10. The reference number for the total (e.g., combined) length of Indicator LOH Regions may be about 75, 90, 105, 120, 130, 135, 150, 175, 200, 225, 250, 275, 300, 325 350, 375, 400, 425, 450, 475, 500 megabases or greater, preferably about 75 megabases or greater, preferably about 90 or 105 megabases or greater, more preferably about 120 or 130 megabases or greater, and more preferably about 135 megabases or greater, and most preferably about 150 megabases or greater.

In some specific embodiments, the total number of LOH regions of a length of greater than about 14 or 15 megabases is determined and compared to a reference number of about 5, 6, 7, 8, 9, 10, 11, 12, 13, 14, 15, 16, 18, 19, or 20. Alternatively or in addition, the total length of LOH regions of a length of greater than about 14 or 15 megabases is determined and compared to a reference number of about 75, 90, 105, 120, 130, 135, 150, 175, 200, 225, 250, 275, 300, 325 350, 375, 400, 425, 450, 475, or 500 megabases.

In some embodiments, the number of LOH regions (or the combined length, or a test value or score derived from either) in a patient sample is considered "greater" than a reference if it is at least 2-, 3-, 4-, 5-, 6-, 7-, 8-, 9-, or 10-fold greater than the reference while in some embodiments, it is considered "greater" if it is at least 1, 2, 3, 4, 5, 6, 7, 8, 9, or 10 standard deviations greater than the reference. Conversely, in some embodiments the number of LOH regions (or the combined length, or a test value or score derived from either) in a patient sample is considered "not greater" than a reference if it is not more than 2-, 3-, 4-, 5-, 6-, 7-, 8-, 9-, or 10-fold greater than the reference while in some embodiments, it is considered "not greater" if it is not more than 1, 2, 3, 4, 5, 6, 7, 8, 9, or 10 standard deviations greater than the reference.

In some embodiments the reference number (or length, value or score) is derived from a relevant reference population. Such reference populations may include patients (a) with the same cancer as the patient being tested, (b) with the same cancer sub-type, (c) with cancer having similar genetic or other clinical or molecular features, (d) who responded to a particular treatment, (e) who did not respond to a particular treatment, (f) who are apparently healthy (e.g., do not have any cancer or at least do not have the tested patient's cancer), etc. The reference number (or length, value or score) may be (a) representative of the number (or length, value or score) found in the reference population as a whole, (b) an average (mean, median, etc.) of the number (or length, value or score) found in the reference population as a whole or a particular subpopulation, (c) representative of the number (or length, value or score) (e.g., an average such as mean or median) found in terciles, quartiles, quintiles, etc. of the reference population as ranked by (i) their respective number (or length, value or score) or (ii) the clinical feature they were found to have (e.g., strength of response, prognosis (including time to cancer-specific death), etc.).

As described herein, patients having cancer cells identified as having a positive LOH signature status or increase in the NAI or NtAI can be classified, based at least in part on a positive LOH signature status or increase in the NAI or NtAI, as being likely to respond to a particular cancer treatment regimen. For example, patients having cancer cells with a genome containing an LOH signature or increase in the NAI or NtAI can be classified, based at least in part on a positive LOH signature status or increase in the NAI or NtAI, as being likely to respond to a cancer treatment regimen that includes the use of a DNA damaging agent, a synthetic lethality agent (e.g., a PARP inhibitor), radiation, or a combination thereof. Preferably the patients are treatment naïve patients.

Examples of DNA damaging agents include, without limitation, platinum-based chemotherapy drugs (e.g., cisplatin, carboplatin, oxaliplatin, and picoplatin), anthracyclines (e.g., epirubicin and doxorubicin), topoisomerase I inhibitors (e.g., campothecin, topotecan, and irinotecan), DNA crosslinkers such as mitomycin C, and triazene compounds (e.g., dacarbazine and temozolomide). Synthetic lethality therapeutic approaches typically involve administering an agent that inhibits at least one critical component of a biological pathway that is especially important to a particular tumor cell's survival. For example, when a tumor cell has a deficient homologous repair pathway (e.g., as determined according to the present invention), inhibitors of poly ADP ribose polymerase (or platinum drugs, double strand break repair inhibitors, etc.) can be especially potent against such tumors because two pathways critical to survival become obstructed (one biologically, e.g., by BRCA1 mutation, and the other synthetically, e.g., by administration of a pathway drug). Synthetic lethality approaches to cancer therapy are described in, e.g., O'Brien et al., Converting cancer mutations into therapeutic opportunities, EMBO MOL. MED. (2009) 1:297-299.

Examples of synthetic lethality agents include, without limitation, PARP inhibitors or double strand break repair inhibitors in homologous repair-deficient tumor cells, PARP inhibitors in PTEN-deficient tumor cells, methotrexate in MSH2-deficient tumor cells, etc. Examples of PARP inhibitors include, without limitation, olaparib, iniparib, and veliparib. Examples of double strand break repair inhibitors include, without limitation, KU55933 (ATM inhibitor) and NU7441 (DNA-PKcs inhibitor). Examples of information that can be used in addition to a positive LOH signature status to base a classification of being likely to respond to a particular cancer treatment regimen include, without limitation, previous treatment results, germline or somatic DNA mutations, gene or protein expression profiling (e.g., ER/PR/

HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc.

In addition to predicting likely treatment response or selecting desirable treatment regimens, an LOH signature or increase in the NAI or NtAI can be used to determine a patient's prognosis. We have shown that patients whose tumors have an LOH signature or increase in the NAI or NtAI show significantly better survival than patients whose tumors do not have such an LOH signature or increase in the NAI or NtAI. Thus, in one aspect, this document features a method for determining a patient's prognosis based at least in part of detecting the presence or absence of an LOH signature or increase in the NAI or NtAI in a sample from the patient. The method comprises, or consists essentially of, (a) determining whether the patient comprises cancer cells having an LOH signature or increase in the NAI or NtAI as described herein (e.g., wherein the presence of more than a reference number of LOH regions in at least one pair of human chromosomes of a cancer cell of the cancer patient that are longer than a first length but shorter than the length of the whole chromosome containing the LOH region or AI or tAI region indicates that the cancer cells have the LOH signature or increase in the NAI or NtAI, wherein the at least one pair of human chromosomes is not a human X/Y sex chromosome pair, wherein the first length is about 1.5 or more megabases), and (b)(1) determining, based at least in part on the presence of the LOH signature or increase in the NAI or NtAI, that the patient has a relatively good prognosis, or (b)(2) determining, based at least in part on the absence of the LOH signature or increase in the NAI or NtAI, that the patient has a relatively poor prognosis.

Prognosis may include the patient's likelihood of survival (e.g., progression-free survival, overall survival), wherein a relatively good prognosis would include an increased likelihood of survival as compared to some reference population (e.g., average patient with this patient's cancer type/subtype, average patient not having an LOH signature or increase in the NAI or NtAI, etc.). Conversely, a relatively poor prognosis in terms of survival would include a decreased likelihood of survival as compared to some reference population (e.g., average patient with this patient's cancer type/subtype, average patient having an LOH signature or increase in the NAI or NtAI, etc.).

"Telomeric allelic imbalance" means allelic imbalance in a telomeric region or segment. "Allelic imbalance" in a region or a "region of allelic imbalance" means allelic imbalance in at least some number of loci defining (in whole or in part) such region. These are generally to be distinguished from isolated loci of allelic imbalance. Thus, in some embodiments regions of allelic imbalance are defined as at least 2, 3, 4, 5, 10, 15, 20, 25, 50, 75, 100, 150, 200, 250, 300, 400, 500, or more consecutive probes showing allelic imbalance.

The number or proportion of telomeric regions having allelic imbalance can be used to derive a telomeric allelic imbalance score (sometimes referred to herein as NtAI), which is analogous to the chromosomal aberration score described above (including the GCAS) and particularly below, though focused on telomeric regions. Thus, in some embodiments the invention provides a method of deriving a telomeric allelic imbalance score comprising: determining whether a sample has a chromosomal aberration (e.g., of allelic imbalance, loss of heterozygosity, copy number aberrations, copy number gain, copy number decrease) at a plurality of assay (e.g., genomic) loci; analyzing a plurality of test loci within said plurality of assay loci for chromosomal aberrations; combining the data from (2) to derive a score reflecting the overall extent of chromosomal aberration in said plurality of test loci, thereby deriving a chromosomal aberration score.

In some embodiments, the data are combined in (3) in such a way that each test locus is assigned a weighting coefficient that determines its contribution to the chromosomal aberration score and telomeric loci are weighted such that they contribute at least 5% (or 10%, or 15%, or 20%, or 30%, or 40%, or 50%, or 60%, or 70%, or 80%, or 90%, or 95%, or 100%) to the chromosomal aberration score. In some embodiments, at least 5% (or 10%, or 15%, or 20%, or 30%, or 40%, or 50%, or 60%, or 70%, or 80%, or 90%, or 95%, or 100%) of the test loci in (2) are telomeric loci.

In some embodiments the telomeric allelic imbalance score will count all telomeric regions showing allelic imbalance. In some embodiments this will include regions of allelic imbalance that encompass an entire chromosome. In some embodiments the telomeric allelic imbalance score will count all telomeric regions of at least some minimum size (e.g., 1 Mb, 2 Mb, 3 Mb, 4 Mb, 5 Mb, 6 Mb, 7 Mb, 8 Mb, 9 Mb, 10 Mb, 11 Mb, 12 Mb, 13 Mb, 14 Mb, 15 Mb, 16 Mb, 17 Mb, 18 Mb, 19 Mb, 20 Mb, 21 Mb, 22 Mb, 23 Mb, 24 Mb, 25 Mb, or more, or any range in between, such as between 5 and 25 Mb) showing allelic imbalance.

In some embodiments, at least 1, 2, 3, 4, 5, 10, 15, 20, 25, 50, 75, or 100 or more telomeric regions with allelic imbalance (e.g., a high telomeric allelic imbalance score (e.g., a score of at least 1, 2, 3, 4, 5, 10, 15, 20, 22, 23, 23.5, 24, 25, 26, 27, 50, 75, or 100 or more)) indicates an increased likelihood of response to therapy comprising a particular modality (e.g., platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin; and synthetic derivatives thereof).

Thus, in some embodiments the invention provides a method of predicting whether a patient will respond to a particular treatment comprising: determining whether a sample has a chromosomal aberration (e.g., of allelic imbalance, loss of heterozygosity, copy number aberrations, copy number gain, copy number decrease) at a plurality of assay (e.g., genomic) loci; analyzing a plurality of test loci within said plurality of assay loci for chromosomal aberrations; combining the data from (2) to derive a chromosomal aberration score reflecting the overall extent of chromosomal aberration in said plurality of test loci; correlating a high chromosomal aberration score to increased likelihood of response to a particular treatment.

In some embodiments, the data are combined in (3) in such a way that each test locus is assigned a weighting coefficient that determines its contribution to the chromosomal aberration score and telomeric loci are weighted such that they contribute at least 5% (or 10%, or 15%, or 20%, or 30%, or 40%, or 50%, or 60%, or 70%, or 80%, or 90%, or 95%, or 100%) to the chromosomal aberration score. In some embodiments, at least 5% (or 10%, or 15%, or 20%, or 30%, or 40%, or 50%, or 60%, or 70%, or 80%, or 90%, or 95%, or 100%) of the test loci in (2) are telomeric loci. In some embodiments the telomeric allelic imbalance score will count all telomeric regions showing allelic imbalance. In some embodiments this will include regions of allelic imbalance that encompass an entire chromosome. In some embodiments the telomeric allelic imbalance score will count all telomeric regions of at least some minimum size (e.g., 1 Mb, 2 Mb, 3 Mb, 4 Mb, 5 Mb, 6 Mb, 7 Mb, 8 Mb, 9 Mb, 10 Mb, 11 Mb, 12 Mb, 13 Mb, 14 Mb, 15 Mb, 16 Mb, 17 Mb, 18 Mb, 19 Mb, 20 Mb, 21 Mb, 22 Mb, 23 Mb, 24 Mb, 25 Mb, or more, or any range in between, such as between 5 and 25 Mb) showing allelic imbalance. In some embodiments, a telomeric allelic imbalance score is high if at least 1, 2, 3, 4, 5, 10, 15, 20, 25, 50, 75, or 100 or more telomeric regions have allelic imbalance.

Heterozygous SNPs can be used in the methods of the invention to determine the phenotype of a cancer are informative, meaning heterozygosity is observed in the nucleic acid sample from non-cancerous tissue and/or cells of a subject. According to the methods of the invention, these informative SNPs are examined in the nucleic acid sample from a cancerous tissue and/or cells of a subject to determine GCAS. In a further embodiment, the nucleic acid samples used to determine the number of heterozygous SNPs in the plurality of SNPs, that exhibit heterozygosity in genomic DNA of non-cancerous tissue of the species to which the cancer patient belongs, are taken from at least 1, 2, 5, 10, 20, 30, 40, 50, 100, or 250 different organisms of that species. A skilled artisan will understand that appropriate controls can be determined based upon the average frequency of SNP alleles that exist within the same ethnic group of the species to which the patient belongs. In certain embodiments, the informative SNPs used in the methods of the invention to determine and/or predict the phenotype of a cancer comprise at least one SNP on each chromosome of a subject (e.g., a telomeric region of each chromosome). In a related embodiment, the informative SNPs used in the methods of the invention to determine and/or predict the phenotype of a cancer comprise at least one SNP on each arm of each chromosome of a subject (e.g., a telomeric region of each arm of each chromosome).

In certain embodiments, the invention provides methods for determining the phenotype of a cancer wherein the phenotype is response to therapy. The therapy may be any anti-cancer therapy including, but not limited to, chemotherapy, radiation therapy, immunotherapy, small molecule inhibitors, shRNA, hormonal, and combinations thereof. Where GCAS represents copy deletions, copy gains, whole chromosome losses, whole chromosome gains and/or loss of heterozygosity, subjects whose cancerous tissue exhibit a GCAS below a threshold value are predicted to have a poorer response to therapy (e.g., radiation or chemotherapy) than those with high GCAS (above the threshold value). Where GCAS represents lack of copy or chromosome number changes and/or retention of heterozygosity, subjects whose cancerous tissue exhibits a GCAS above a threshold value are predicted to have a poorer response to therapy (e.g., radiation or chemotherapy) than those with low GCAS (below the threshold value).

By way of explanation, but without being bound by theory, it is believed that where the GCAS value represents loss of heterozygosity or allelic imbalance, it identifies cells harboring improperly repaired chromosomal DNA double-strand breaks and the genome-wide count of these chromosomal rearrangements in a specific tumor indicates the degree of DNA repair incompetence, independent of the specific causative DNA repair defect. In such subjects, the total number of chromosomal rearrangements in a tumor indicates the inability to repair DNA damage induced by anti-cancer therapies, and consequently predicts sensitivity to such anti-cancer therapies. Also by way of explanation and without being bound by theory, it is believed that GCAS representing copy gains may indicate genetic defects other than or in addition to DNA repair defects and that GCAS representing whole chromosome loss or gain may indicate mitotic checkpoint defects or chromosome segregation defects, and the like. Such aberrations in faithful DNA repair, segregation, check point control, etc. has been determined to be predictive of the cells harboring such aberrations to treatment with anti-cancer therapies (e.g., chemotherapeutics) in subjects.

The response to anti-cancer therapies relates to any response of the tumour to chemotherapy, preferably to a change in tumour mass and/or volume after initiation of neoadjuvant or adjuvant chemotherapy. Tumor response may be assessed in a neoadjuvant or adjuvant situation where the size of a tumour after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumour after biopsy or surgical resection. Response may be recorded in a quantitative fashion like percentage change in tumour volume or cellularity or using a semi-quantitative scoring system such as residual cancer burden (Symmans et al., J. Clin. Oncol. (2007) 25:4414-5 4422) or Miller-Payne score (Ogston et al., Breast (Edinburgh, Scotland) (2003) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

Additional criteria for evaluating the response to anti-cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to GCAS's that were determined prior to administration of any anti-cancer therapy. The outcome measurement may be pathologic response to therapy given in the neo-adjuvant setting. Alternatively, outcome measures, such as overall survival and disease-free survival can be monitored over a period of time for subjects following anti-30 cancer therapy for whom GCAS values are known. In certain embodiments, the same doses of anti-cancer agents are administered to each subject. In related embodiments, the doses administered are standard doses known in the art for anti-cancer agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. GCAS threshold values that correlate to outcome of an anti-cancer therapy can be determined using methods such as those described in the Example section.

In some embodiments, the test value representing the chromosomal aberration score is compared to one or more reference values (or index values), and optionally correlated to an increased (or not) likelihood of response to a particular treatment. For example, the index value may represent the average chromosomal aberration score for a set of individuals from a diverse cancer population or a subset of the population. For example, one may determine the average chromosomal aberration score in a random sampling of patients with cancer (or a particular cancer). This average chromosomal aberration score may be termed the "threshold index value," with patients having a chromosomal aberration score higher than this value expected to have a higher likelihood of response than those having a chromosomal aberration score lower than this value. In some embodiments the test value is correlated to an increased likelihood of response to a particular treatment if the test value exceeds the reference value by at least some amount (e.g., at least 0.5, 0.75, 0.85, 0.90, 0.95, 1, 2, 3, 4, 5, 6, 7, 8, 9, or 10 or more fold or standard deviations)

Alternatively the index value may represent the average chromosomal aberration score in a plurality of training patients with similar outcomes whose clinical and follow-up data are available and sufficient to define and categorize the patients by outcome, e.g., response to a particular treatment. See, e.g., Examples, infra. For example, a "response index value" can be generated from a plurality of training cancer patients characterized as having "response" to the particular treatment. A "no (or poor) response index value" can be generated from a plurality of training cancer patients defined as having "no (or poor) response" to the particular treatment. Thus, a response prognosis index value may represent the average chromosomal aberration score in patients having "response," whereas a no (or poor) response index value represents the average chromosomal aberration score in patients having no or poor response. Thus, when the determined chromosomal aberration score is closer to the response index value than to the no response index value, then it can be concluded that the patient is more likely to respond. On the other hand, if the determined 1 chromosomal aberration score is closer to the no response index value than to the response index value, then it can be concluded that the patient does not have an increased likelihood of response.

Prognosis may include the patient's likelihood of survival (e.g., progression-free survival, overall survival), wherein a relatively good prognosis would include an increased likelihood of survival as compared to some reference population (e.g., average patient with this patient's cancer type/subtype, average patient not having an LOH signature, patient not having increased number of AI or tAI etc.). Conversely, a relatively poor prognosis in terms of survival would include a decreased likelihood of survival as compared to some reference population (e.g., average patient with this patient's cancer type/subtype, average patient having an LOH signature, patient not having increased number of AI or tAI etc.).

Anti-Cancer Therapeutic Agents

The efficacy of anti-cancer therapies which damage DNA, as well as agents that take advantage of DNA repair defects but do not damage DNA themselves, such as poly ADP ribose polymerase (PARP) inhibitors, as well as chemotherapy or radiation therapy, is predicted according to the GCAS level of a cancer in a subject according to the methods described herein. In one embodiment, the efficacy of chemotherapies is predicted. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The foregoing examples of chemotherapeutic agents are illustrative, and are not intended to be limiting.

In a preferred embodiment, the chemotherapeutic agents are platinum compounds or platinum-comprising cancer therapies, such as cisplatin, carboplatin, oxaliplatin, nedaplatin, and iproplatin. Other antineoplastic platinum coordination compounds are well known in the art, can be modified according to well-known methods in the art, and include the compounds disclosed in U.S. Pat. Nos. 4,996,337, 4,946, 954, 5,091,521, 5,434,256, 5,527,905, and 5,633,243, all of which are incorporated herein by reference. In another embodiment, GCAS predicts efficacy of radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Anti-cancer therapies which damage DNA to a lesser extent than chemotherapy or radiation therapy may have efficacy in subjects determined to have relatively lower or higher GCAS determinations using the methods of the invention for determining the phenotype of a cancer. Examples of such therapies include immunotherapy, hormone therapy, and gene therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be used in such therapies.

Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In one embodiment, anti-cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Cancers for which Phenotype can be Determined

The methods of the invention can be used to determine the phenotype of many different cancers. Specific examples of types of cancers for which the phenotype can be determined by the methods encompassed by the invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the cancer cells are primary or metastatic cancer cells of ovarian cancer, breast cancer, lung cancer or esophageal cancer.

In some embodiments, the cancer whose phenotype is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

Subjects

In one embodiment, the subject for whom predicted efficacy of an anti-cancer therapy is determined, is a mammal (e.g., mouse, rat, primate, non-human mammal, domestic animal such as dog, cat, cow, horse), and is preferably a human. In another embodiment of the methods of the invention, the subject has not undergone chemotherapy or radiation therapy. In alternative embodiments, the subject has undergone chemotherapy or radiation therapy (e.g., such as with cisplatin, carboplatin, and/or taxane). In related embodiments, the subject has not been exposed to levels of radiation or chemotoxic agents above those encountered generally or on average by the subjects of a species. In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

In some embodiments, the patients are treatment naïve patients.

According to one aspect of the invention, GCAS can be used to determine the phenotype, i.e. responsiveness to therapy of a cancer in a subject, where the subject has previously undergone chemotherapy, radiation therapy, or has been exposed to radiation, or a chemotoxic agent. Such therapy or exposure could potentially damage DNA and alter the numbers of informative heterozygous SNPs in a subject. The altered number of informative heterozygous SNPs would in turn alter the GCAS of a subject. Because the non-cancerous DNA samples would exhibit greater or fewer heterozygous SNPs, the range of GCASs would be altered for a population of subjects. In certain embodiments, DNA damage from therapy or exposure in a subject or population of subjects occurs about 1 month, 2 months, 3 months, 4 months, 5 months, 6 months, 7 months, 8 months, 9 months, 10 months, 11 months, 1 year, 1.5 years, 2 years or more before determination of GCAS. To determine GCAS threshold values for subjects that exhibit DNA damage from therapy or exposure, a population of subjects is monitored who have had chemotherapy or radiation therapy, preferably via identical or similar treatment regimens, including dose and frequency, for said subjects.

Nucleic Acid Sample Preparation

Nucleic Acid Isolation

Nucleic acid samples derived from cancerous and non-cancerous cells of a subject that can be used in the methods of the invention to determine the phenotype of a cancer can be prepared by means well known in the art. For example, surgical procedures or needle biopsy aspiration can be used to collect cancerous samples from a subject. In some embodiments, it is important to enrich and/or purify the cancerous tissue and/or cell samples from the non-cancerous tissue and/or cell samples. In other embodiments, the cancerous tissue and/or cell samples can then be microdissected to reduce amount of normal tissue contamination prior to extraction of genomic nucleic acid or pre-RNA for use in the methods of the invention. In still another embodiment, the cancerous tissue and/or cell samples are enriched for cancer cells by at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range in between, in cancer cell content. Such enrichment can be accomplished according to methods well-15 known in the art, such as needle microdissection, laser microdissection, fluorescence activated cell sorting, and immunological cell sorting. In one embodiment, an automated machine performs the hyperproliferative cell enrichment to thereby transform the biological sample into a purified form enriched for the presence of hyperproliferative cells.

Collecting nucleic acid samples from non-cancerous cells of a subject can also be accomplished with surgery or aspiration. In surgical procedures where cancerous tissue is removed, surgeons often remove non-cancerous tissue and/or cell samples of the same tissue type of the cancer patient for comparison. Nucleic acid samples can be isolated from such non-cancerous tissue of the subject for use in the methods of the invention. In certain embodiments of the methods of the invention, nucleic acid samples from non-cancerous tissues are not derived from the same tissue type as the cancerous tissue and/or cells sampled, and/or are not derived from the cancer patient. The nucleic acid samples from non-cancerous tissues may be derived from any non-cancerous and/or disease-free tissue and/or cells. Such non-cancerous samples can be collected by surgical or non-surgical procedures. In certain embodiments, non-cancerous nucleic acid samples are derived from tumor-free tissues. For example, non-cancerous samples may be collected from lymph nodes, peripheral blood lymphocytes, and/or mononuclear blood cells, or any subpopulation thereof. In a preferred embodiment, the non-cancerous tissue is not precancerous tissue, e.g., it does not exhibit any indicia of a pre-neoplastic condition such as hyperplasia, metaplasia, or dysplasia.

In one embodiment, the nucleic acid samples used to compute GCAS (e.g., the number of heterozygous SNPs in the plurality of total SNPs that exhibit heterozygosity in genomic DNA of non-cancerous tissue of the species to which the cancer patient belongs) are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine heterozygosity of SNPs, can be fragments of genomic nucleic acid generated by restriction enzyme digestion and/or ligation to other nucleic acid, and/or amplification products of genomic nucleic acids, or pre-messenger RNA (pre-mRNA), amplification products of pre-mRNA, or genomic DNA fragments grown up in cloning vectors generated, e.g., by "shotgun" cloning methods. In certain embodiments, genomic nucleic acid samples are digested with restriction enzymes.

Amplification of Nucleic Acids

Though the nucleic acid sample need not comprise amplified nucleic acid, in some embodiments, the isolated nucleic acids can be processed in manners requiring and/or taking advantage of amplification. The genomic DNA samples of a subject optionally can be fragmented using restriction endonucleases and/or amplified prior to determining GCAS. In one embodiment, the DNA fragments are amplified using polymerase chain reaction (PCR). Methods for practicing PCR are well known to those of skill in the art. One advantage of PCR is that small quantities of DNA can be used. For example, genomic DNA from a subject may be about 150 ng, 175, ng, 200 ng, 225 ng, 250 ng, 275 ng, or 300 ng of DNA.

In certain embodiments of the methods of the invention, the nucleic acid from a subject is amplified using a single primer pair. For example, genomic DNA samples can be digested with restriction endonucleases to generate fragments of genomic DNA that are then ligated to an adaptor DNA sequence which the primer pair recognizes. In other embodiments of the methods of the invention, the nucleic acid of a subject is amplified using sets of primer pairs specific to loci of interest (e.g., RFLPs, STRs, SNPs, etc.) located throughout the genome. Such sets of primer pairs each recognize genomic DNA sequences flanking particular loci of interest (e.g., SNPs, RFLPs, STRs, etc.). A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

In other embodiments, where genomic DNA of a subject is fragmented using restriction endonucleases and amplified prior to determining GCAS, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51).

In yet other embodiments, where the DNA of a subject is fragmented using restriction endonucleases and amplified prior to determining GCAS, the amplification comprises expressing a nucleic acid encoding a gene, or a gene and flanking genomic regions of nucleic acids, from the subject. RNA (pre-messenger RNA) that comprises the entire transcript including introns is then isolated and used in the methods of the invention to determine GCAS and the phenotype of a cancer. In certain embodiments, no amplification is required. In such embodiments, the genomic DNA, or pre-RNA, of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

Hybridization

The nucleic acid samples derived from a subject used in the methods of the invention can be hybridized to arrays comprising probes (e.g., oligonucleotide probes) in order to identify informative loci of interest (e.g., SNPs, RFLPs, STRs, etc.). Hybridization can also be used to determine whether the informative loci of interest (e.g., SNPs, RFLPs, STRs, etc.) identified exhibit chromosomal aberrations (e.g., allelic imbalance, loss of heterozygosity, total copy number change, copy number gain, and copy number loss) in nucleic acid samples from cancerous tissues and/or cells of the subject. In preferred embodiments, the probes used in the methods of the invention comprise an array of probes that can be tiled on a DNA chip (e.g., SNP oligonucleotide probes). In some embodiments, heterozygosity of a SNP locus is determined by a method that does not comprise detecting a change in size of restriction enzyme-digested nucleic acid fragments. In other embodiments, SNPs are analyzed to identify allelic imbalance. Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays such as those used to analyze SNPs in MIP assays. The single-stranded synthetic oligodeoxyribonucleic acid DNA probes of an array may need to be denatured prior to contact with the nucleic acid samples from a subject, e.g., to remove hairpins or dimers which form due to self-complementary sequences.

Optimal hybridization conditions will depend on the length of the probes and type of nucleic acid samples from a subject. General parameters for specific (i.e., stringent) hybridization conditions for nucleic acids are described in Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51 and 11.55-11.61; Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization With Nucleic Acid Probes, Elsevier Science Publishers B. V. and Kricka, 1992, Nonisotopic DNA Probe Techniques, Academic Press, San Diego, Calif.

Oligonucleotide Nucleic Acid Arrays

In some embodiments of the methods of the present invention, DNA arrays can be used to determine whether nucleic acid samples exhibit chromosomal aberrations (e.g., allelic imbalance, loss of heterozygosity, total copy number change, copy number gain, and copy number loss) by measuring the level of hybridization of the nucleic acid sequence to oligonucleotide probes that comprise complementary sequences. Hybridization can be used to determine the presence or absence of heterozygosity. Various formats of DNA arrays that employ oligonucleotide "probes," (i.e., nucleic acid molecules having defined sequences) are well known to those of skill in the art. Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

Numerous variations on nucleic acid arrays useful in the invention are known in the art. These include Affymetrix 500K GeneChip array; Affymetrix OncoScan™ FFPE Express 2.0 Services (Formerly MIP CN Services), and the like.

Preferably, the microarrays are made from materials that are stable under binding (e.g., nucleic acid hybridization) conditions. The microarrays are preferably small, e.g., between about 1 cm2 and 25 cm2, preferably about 1 to 3 cm2. However, both larger and smaller arrays are also contemplated and may be preferable, e.g., for simultaneously evaluating a very large number of different probes. Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. Using DNA array assays, complex mixtures of labeled nucleic acids, e.g., nucleic acid fragments derived a restriction digestion of genomic DNA from non-cancerous tissue, can be analyzed. DNA array technologies have made it possible to determine heterozygosity of a large number of informative loci of interest (e.g., SNPs, RFLPs, STRs, etc.) throughout the genome.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors And Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules corresponding to each informative locus of interest (e.g., SNPs, RFLPs, STRs, etc.).

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof. The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

In some embodiments, the high-density oligonucleotide arrays used in the methods of the invention comprise oligonucleotides corresponding to informative loci of interest (e.g., SNPs, RFLPs, STRs, etc.). The oligonucleotide probes may comprise DNA or DNA "mimics" (e.g., derivatives and analogues) corresponding to a portion of each informative locus of interest (e.g., SNPs, RFLPs, STRs, etc.) in a subject's genome. The oligonucleotide probes can be modified at the base moiety, at the sugar moiety, or at the phosphate backbone. Exemplary DNA mimics include, e.g., phosphorothioates. For each SNP locus, a plurality of different oligonucleotides may be used that are complementary to the sequences of sample nucleic acids. For example, for a single informative locus of interest (e.g., SNPs, RFLPs, STRs, etc.) about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more different oligonucleotides can be used. Each of the oligonucleotides for a particular informative locus of interest may have a slight variation in perfect matches, mismatches, and flanking sequence around the SNP. In certain embodiments, the probes are generated such that the probes for a particular informative locus of interest comprise overlapping and/or successive overlapping sequences which span or are tiled across a genomic region containing the target site, where all the probes contain the target site. By way of example, overlapping probe sequences can be tiled at steps of a predetermined base intervals, e. g. at steps of 1, 2, 3, 4, 5, 6, 7, 8, 9, or 10 bases intervals. In certain embodiments, the assays can be performed using arrays suitable for use with molecular inversion probe protocols such as described by Wang et al. (2007) *Genome Biol.* 8, R246. For oligonucleotide probes targeted at nucleic acid species of closely resembled (i.e., homologous) sequences, "cross-hybridization" among similar probes can significantly contaminate and confuse the results of hybridization measurements. Cross-hybridization is a particularly significant concern in the detection of SNPs since the sequence to be detected (i.e., the particular SNP) must be distinguished from other sequences that differ by only a single nucleotide. Cross-hybridization can be minimized by regulating either the hybridization stringency condition and/ or during post-hybridization washings. Highly stringent conditions allow detection of allelic variants of a nucleotide sequence, e.g., about 1 mismatch per 10-30 nucleotides. There is no single hybridization or washing condition which is optimal for all different nucleic acid sequences. For particular arrays of informative loci of interest, these conditions can be identical to those suggested by the manufacturer or can be adjusted by one of skill in the art. In preferred embodiments, the probes used in the methods of the invention are immobilized (i.e., tiled) on a glass slide called a chip. For example, a DNA microarray can comprises a chip on which oligonucleotides (purified single-stranded DNA sequences in solution) have been robotically printed in an (approximately) rectangular array with each spot on the array corresponds to a single DNA sample which encodes an oligonucleotide. In summary the process comprises, flooding the DNA microarray chip with a labeled sample under conditions suitable for hybridization to occur between the slide sequences and the labeled sample, then the array is washed and dried, and the array is scanned with a laser microscope to detect hybridization. In certain embodiments there are at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 50,000, 60,000, 70,000, 80,000, 90,000, 100,000 or more or any range in between, of informative loci of interest for which probes appear on the array (with match/mismatch probes for a single locus of interest or probes tiled across a single locus of interest counting as one locus of interest). The maximum number of informative loci of interest being probed per array is determined by the size of the genome and genetic diversity of the subjects species. DNA chips are well known in the art and can be purchased in pre-5 fabricated form with sequences specific to particular species. In some embodiments, the Genome-Wide Human SNP Array 6.0™ and/or the 50K XbaI arrays (Affymetrix, Santa Clara, Calif.) are used in the methods of the invention. In other embodiments, SNPs and/or DNA copy number can be detected and quantitated using sequencing methods, such as "next-generation sequencing methods" as described further above.

Signal Detection

In some embodiments, nucleic acid samples derived from a subject are hybridized to the binding sites of an array described herein. In certain embodiments, nucleic acid samples derived from each of the two sample types of a subject (i.e., cancerous and non-cancerous) are hybridized to separate, though identical, arrays. In certain embodiments, nucleic acid samples derived from one of the two sample types of a subject (i.e., cancerous and non-cancerous) is hybridized to such an array, then following signal detection the chip is washed to remove the first labeled sample and reused to hybridize the remaining sample. In other embodiments, the array is not reused more than once. In certain embodiments, the nucleic acid samples derived from each of the two sample types of a subject (i.e., cancerous and non-cancerous) are differently labeled so that they can be distinguished. When the two samples are mixed and hybridized to the same array, the relative intensity of signal from each sample is determined for each site on the array, and any relative difference in abundance of an allele of informative loci of interest detected. Signals can be recorded and, in some embodiments, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the array, a ratio of the emission of the two fluorophores can be calculated, which may help in eliminating cross hybridization signals to more accurately determining whether a particular SNP locus is heterozygous or homozygous.

Labeling

In some embodiments, the nucleic acids samples, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, 32P and 14C. Fluorescent molecules suitable for the present invention include, but are not limited to, fluorescein and its derivatives, rhodamine and its derivatives, texas red, 5'carboxy-fluorescein ("FAM"), 2',7'-dimethoxy-4',5'-dichloro-6-carboxy-fluorescein ("JOE"), N, N, N',N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto. Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) *Genome Res.* 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) *Genome*

Res. 6, 639-645. Alternatively, a fiber-optic bundle can be used such as that described by Ferguson et al. (1996) *Nat. Biotech.* 14, 1681-1684. The resulting signals can then be analyzed to determine the presence or absence of heterozygosity or homozygosity for informative loci of interest (e.g., SNPs, RFLPs, STRs, etc.) using computer software.

Algorithms for Analyzing Informative Loci of interest

Once the hybridization signal has been detected the resulting data can be analyzed using algorithms. In certain embodiments, the algorithm for determining heterozygosity at informative loci of interest (e.g., SNPs, RFLPs, STRs, etc.) is based on well known methods for calling allelic imbalance (AI), loss of heterozygosity (LOH), copy number aberrations (CNA), copy number gain (CNG), and copy number decrease (CND). For example, AI can be determined using major copy proportion (MCP) wherein AI for a given SNP is called, when the MCP value is greater than 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.92, 0.93, 0.94, 0.95, 0.96, 0.97, 0.98, or 0.99. Once calling is determined, enumeration methods can further be applied. For example, GCAS can be determined, for example, by: 1) the count of the total number of SNPs affected by AI or copy gain or LOH, 2) the count of the number of regions affected by AI (e.g., NAI as described further in the Examples; a single region is defined as a string of neighboring SNPs all showing AI bounded on at least one side by SNPs showing no AI/retention of heterozygosity. The region size is defined by the length of the chromosome represented by the string of SNPs with AI); 3) the count of the number of chromosomes with whole chromosome loss, or 4) the count of the number of chromosomal regions with CNA, CNG, CND, etc. Additional representative illustrations of such well known algorithms are provided in the Examples section below.

Computer Implementation Systems and Methods

In certain embodiments, the methods of the invention implement a computer program to calculate a chromosomal aberration score (e.g., GCAS, telomeric aberration score, telomeric allelic imbalance score, etc.). For example, a computer program can be used to perform the algorithms described herein. A computer system can also store and manipulate data generated by the methods of the present invention which comprises a plurality of hybridization signal changes/profiles during approach to equilibrium in different hybridization measurements and which can be used by a computer system in implementing the methods of this invention. In certain embodiments, a computer system receives probe hybridization data; (ii) stores probe hybridization data; and (iii) compares probe hybridization data to determine the state of informative loci of interest in said nucleic acid sample from cancerous or pre-cancerous tissue. The GCAS is then calculated. In some embodiments, a computer system (i) compares the determined GCAS to a threshold value; and (ii) outputs an indication of whether said GCAS is above or below a threshold value, or a phenotype based on said indication. In certain embodiments, such computer systems are also considered part of the present invention.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; CRLMM software described in Silver et al. (2007) *Cell* 128, 991-1002; Aroma Affymetrix software described in Richardson et al. (2006) *Cancer Cell* 9, 121-132. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.). In certain embodiments, the computer comprises a database for storage of hybridization signal profiles. Such stored profiles can be accessed and used to calculate GCAS. For example, of the hybridization signal profile of a sample derived from the non-cancerous tissue of a subject and/or profiles generated from population-based distributions of informative loci of interest in relevant populations of the same species were stored, it could then be compared to the hybridization signal profile of a sample derived from the cancerous tissue of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Once a laboratory technician or laboratory professional or group of laboratory technicians or laboratory professionals determines whether a sample has a chromosomal aberration at a plurality of assay loci as described above (e.g., step (1) in many of the methods above), the same or a different laboratory technician or laboratory professional (or group) can analyze a plurality of test loci to determine whether they have a chromosomal aberration (e.g., step (2) in many of the methods above). Next, the same or a different laboratory technician or laboratory professional (or group) can combine the chromosomal aberration data from the test loci to derive a chromosomal aberration score (e.g., step (3) in many of the methods above). Optionally, the same or a different laboratory technician or laboratory professional (or group) can correlate a high chromosomal aberration score to an increased likelihood of response to a particular therapy (e.g., those mentioned above). For example, one or more laboratory technicians or laboratory professionals can identify a patient having cancer cells that were detected to have a high chromosomal aberration score by associating that high chromosomal aberration score or the result (or results or a summary of results) of the performed diagnostic analysis with the corresponding patient's name, medical record, symbolic/numerical identifier, or a combination thereof. Such identification can be based solely on detecting the presence of a high chromosomal aberration score or can be based at least in part on detecting the presence of a high chromosomal aberration score. For example, a laboratory technician or laboratory professional can identify a patient having cancer cells that were detected to have a high chromosomal aberration score as having cancer cells with an increased likelihood of response to a particular therapy based on a combination of a high chromosomal aberration score and the results of other genetic and biochemical tests performed at the testing laboratory.

Figure 23:
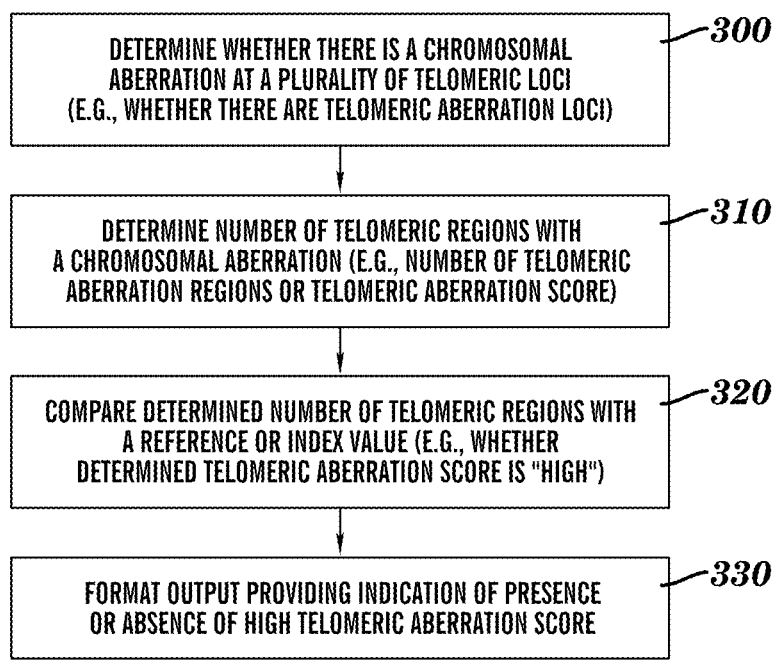
FIG. 23 shows an exemplary process by which a computing system can determine a chromosomal aberration score

FIG. 23 shows an exemplary process by which a computing system can determine a chromosomal aberration score. The process begins at box 300, where data regarding the genotype (e.g., relative or absolute copy number, homozygous, heterozygous) of a plurality of loci along a chromosome is collected by the computing system. As described herein, any appropriate assay such as a SNP array-based assay or sequencing-based assay can be used to assess loci along a chromosome for genotype. In some cases, a system including a signal detector and a computer can be used to collect data (e.g., fluorescent signals or sequencing results) regarding the genotype of the plurality of loci. At box 310, data regarding the genotype of a plurality of loci as well as the location or spatial relationship of each locus is assessed by the computing system to determine, e.g., the length of any chromosomal aberration (e.g., allelic imbalance) regions present along a chromosome or the number of telomeric aberration (e.g., allelic imbalance) regions. At box 320, data regarding the number of chromosomal aberration regions detected and optionally the length or the location of each detected chromosomal aberration region is assessed by the computing system to determine the number of chromosomal aberration regions that are telomeric regions. At box 330, the computing system formats an output providing an indication of the presence or absence of a high chromosomal aberration score. Once formatted, the computing system can present the output to a user (e.g., a laboratory technician, clinician, or medical professional). As described herein, the presence or absence of a high chromosomal aberration score can be used to provide an indication about possible cancer treatment regimens.

Figure 24:
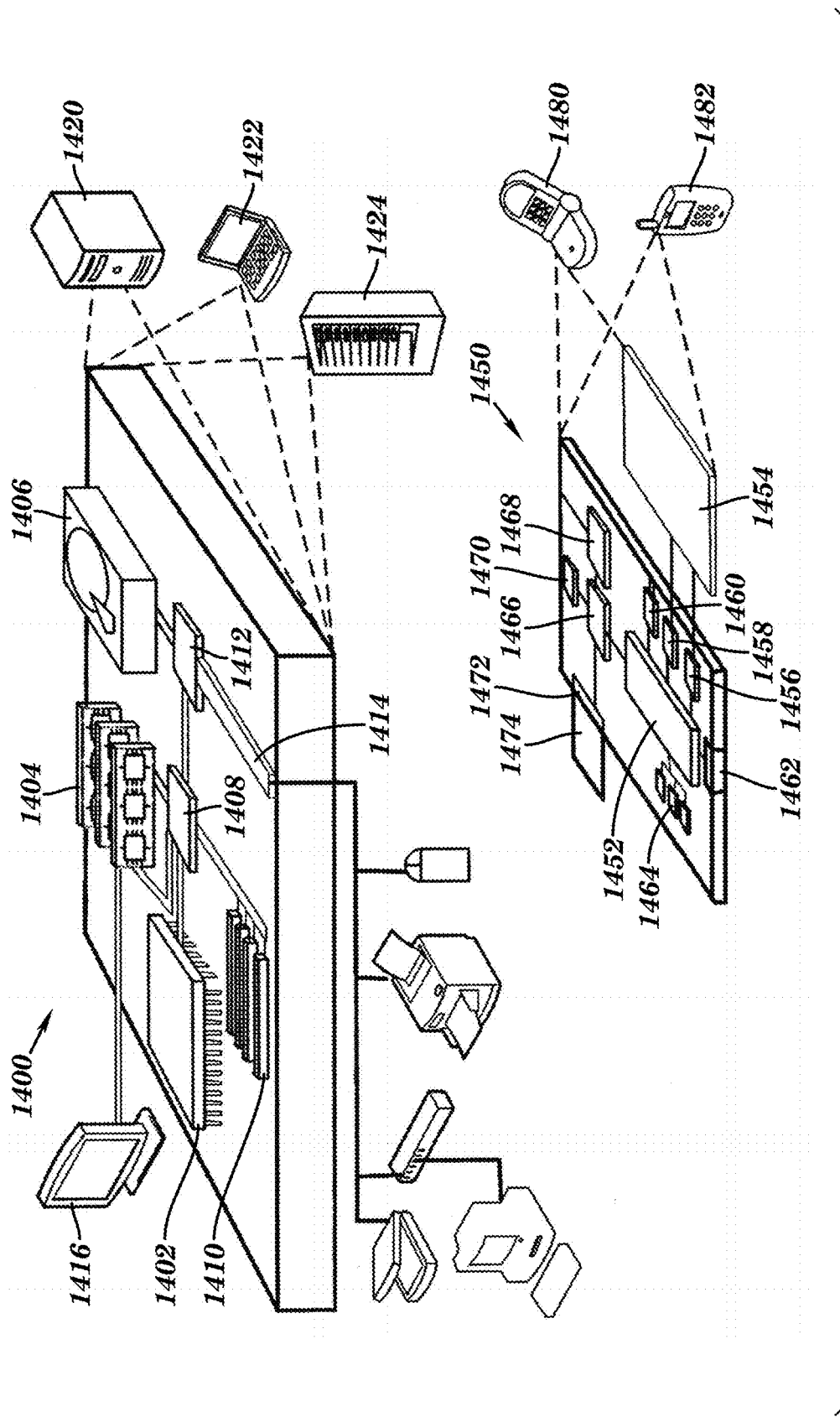
FIG. 24 is a diagram of an example of a computer device 1400 and a mobile computer device 1450, which may be used with the techniques described herein.

FIG. 24 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

The results of any analyses according to the invention will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs or diagrams showing genotype or LOH (or HRD status) information can be used in explaining the results. The statements and visual forms can be recorded on a tangible medium such as papers, computer readable media such as floppy disks, compact disks, flash memory, etc., or in an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on an LOH signature for at least one patient sample. The method comprises the steps of (1) determining an LOH signature according to methods of the present invention; and (2) embodying the result of the determining step in a transmittable form. The transmittable form is a product of such a method.

In some cases, a computing system provided herein can be configured to include one or more sample analyzers. A sample analyzer can be configured to produce a plurality of signals about genomic DNA of at least one pair of human chromosomes of a cancer cell. For example, a sample analyzer can produce signals that are capable of being interpreted in a manner that identifies the homozygous or heterozygous nature of loci along a chromosome. In some cases, a sample analyzer can be configured to carry out one or more steps of a SNP array-based assay or sequencing-based assay and can be configured to produce and/or capture signals from such assays. In some cases, a computing system provided herein can be configured to include a computing device. In such cases, the computing device can be configured to receive signals from a sample analyzer. The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer, from another computing device, from a SNP array-based assay, or from a sequencing-based assay. The analysis of such signals can be carried out to determine genotypes, chromosomal aberration at certain loci, regions of chromosomal aberration, the number of chromosomal aberration regions, to determine the location of chromosomal aberration regions (e.g., telomeric), to determine the number of chromosomal aberration regions having a particular location (e.g., telomeric), to determine whether or not a sample is positive for a high chromosomal aberration score, to determine a likelihood that a cancer patient will respond to a particular cancer treatment regimen (e.g., a regimen as described above), or to determine a combination of these items.

In some cases, a computing system provided herein can include computer-executable instructions or a computer program (e.g., software) containing computer-executable instructions for formatting an output providing an indication about the number of chromosomal aberration regions, the location of chromosomal aberration regions (e.g., telomeric), the number of LOH regions having a particular location (e.g., telomeric), whether or not a sample is positive for a high chromosomal aberration score, a likelihood that a cancer patient will respond to a particular cancer treatment regimen (e.g., a regimen as described above), or a combination of these items. In some cases, a computing system provided herein can include computer-executable instructions or a computer program (e.g., software) containing computer-executable instructions for determining a desired cancer treatment regimen for a particular patient based at least in part on the presence or absence of a high chromosomal aberration score.

In some cases, a computing system provided herein can include a preprocessing device configured to process a sample (e.g., cancer cells) such that a SNP array-based assay or sequencing-based assay can be performed. Examples of preprocessing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

In general, one aspect of this invention features a method for assessing LOH in a cancer cell or genomic DNA thereof. In some embodiments, the method comprises, or consists essentially of, (a) detecting, in a cancer cell or genomic DNA derived therefrom, LOH regions in at least one pair of human chromosomes of the cancer cell (e.g., any pair of human chromosomes other than a human X/Y sex chromosome pair); and (b) determining the number and size (e.g., length) of said LOH regions. In some embodiments, LOH regions are analyzed in a number of chromosome pairs that are representative of the entire genome (e.g., enough chromosomes are analyzed such that the number and size of LOH regions are expected to be representative of the number and size of LOH regions across the genome). In some embodiments, the method further comprises determining the total number of LOH regions that are longer than about 1.5, 5, 12, 13, 14, 15, 16, 17 or more (preferably 14, 15, 16 or more, more preferably 15 or more) megabases but shorter than the entire length of the respective chromosome which the LOH region is located within (Indicator LOH Regions). Alternatively or additionally, the total combined length of such Indicator LOH Regions is determined. In some specific embodiments, if that total number of Indicator LOH Regions or total combined length of Indicator LOH Regions is equal to or greater than a predetermined reference number, then said cancer cell or genomic DNA or a patient having said cancer cell or genomic DNA is identified as having an HDR-deficiency LOH signature.

Other embodiments of the present invention are described in the following Examples. The present invention is further illustrated by the following examples which should not be construed as further limiting.

The following paragraphs define the invention in more detail

1. An assay for selecting therapy for a subject having cancer, the assay comprising
   subjecting a biological sample comprising a cancer cell or nucleic acid from a cancer cell taken from the subject to telomeric allelic imbalance (tAI) analysis;
   detecting the number of telomeric allelic imbalance (NtAI) in the cancer cell or nucleic acid from the cancer cell, and
   selecting a platinum-comprising therapy for the subject when the NtAI is detected to be above a reference value based on the recognition that platinum-comprising therapy is effective in patients who have NtAI above the reference value; and selecting a non-platinum-comprising cancer therapy for the subject when the NtAI is detected to be below a reference value based on the recognition that platinum-comprising cancer therapy is not effective in patients who have the NtAI below a reference value.

2. The assay of paragraph 1 further comprising the step of treating the subject with the selected therapy.

3. The assay of any of the preceding paragraphs, wherein the cancer is breast cancer or ovarian cancer.

4. The assay of any of the preceding paragraphs, wherein the reference value is 22.

5. The assay of any of the preceding paragraphs, wherein the reference value is 24.

6. The assay of any of the preceding paragraphs, wherein the reference value is 27.

7. The assay of any of the preceding paragraphs, wherein the cancer cell does not have mutations in the BRCA1 and/or BRCA2 gene.

8. The assay of any of the preceding paragraphs further comprising a step of assaying for BRCA1 mRNA expression or methylation status of the BRCA1 promoter, detecting the amount of BRCA1 mRNA expression or the amount of methylation of the BRCA1 promoter, wherein the platinum comprising therapy is selected when decreased expression of BRCA1 or increased methylation of BRCA1 promoter is detected.

9. A method for selecting platinum-comprising therapy for a subject having cancer comprising
   subjecting a biological sample taken from the subject to allelic imbalance (AI) analysis;
   detecting the number of AI; and
   selecting platinum-comprising cancer therapy for the subject when the number of AIs is above a reference value based on the recognition that platinum-comprising cancer therapy is effective in patients who have the number of AIs is above a reference value.

10. The method of any of the preceding paragraphs further comprising the step of treating the subject with platinum-comprising cancer therapy when platinum-comprising cancer therapy is selected.

11. The method of any of the preceding paragraphs, wherein the cancer is selected from breast cancer and ovarian cancer.

12. The method of any of the preceding paragraphs, wherein the breast cancer does not have a BRCA1 mutations.

13. The method of any of the preceding paragraphs, wherein the allelic imbalance is within about 25 kB of a copy number variation (CNV).

14. The method of any of the preceding paragraphs, wherein the CNV is pericentromeric or subtelomeric CNV.

15. The method of any of the preceding paragraphs, wherein the allelic imbalance is telomeric allelic imbalance.

16. A method comprising:
    detecting, in a cancer cell or genomic DNA derived therefrom, allelic imbalance in a representative number of pairs of human chromosomes of the cancer cell; and
    determining the number of allelic imbalance.

17. The method of Paragraph 16, said representative number of pairs of human chromosomes is representative of the entire genome.

18. The method of Paragraph 16-17, further comprising correlating an increased number of allelic imbalance regions to an increased likelihood of deficiency in HDR.

19. The method of paragraph 16-18, further comprising correlating an increased number of allelic imbalance regions to an increased likelihood of said cancer cell to respond to platinum comprising cancer therapy.

20. The method of paragraph 16-19, further comprising correlating a non-increased number of allelic imbalance regions to a decreased likelihood of said cancer cell to respond to platinum comprising cancer therapy.

21. The method of paragraph 16-21, wherein the platinum comprising cancer therapy comprises cisplatin, carboplatin, oxalaplatin, or picoplatin.

22. A method comprising:
    a) detecting, in a cancer cell or genomic DNA derived therefrom, LOH regions in a representative number of pairs of human chromosomes of the cancer cell; and
    b) determining the number and size of said LOH regions.

23. The method of Paragraph 22, said representative number of pairs of human chromosomes is representative of the entire genome.

24. The method of Paragraph 22-23, further comprising correlating an increased number of LOH regions of a particular size to an increased likelihood of deficiency in HDR.

25. The method of Paragraph 22-24, wherein said particular size is longer than about 1.5, 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases and less than the length of the entire chromosome that contains the LOH region.

26. The method of any of the paragraphs 22-25, wherein 6, 7, 8, 9, 10, 11, 12 or 13 or more LOH regions of said particular size are correlated to an increased likelihood of deficiency in HDR.

27. A method of determining prognosis in a patient comprising:
    a) determining whether the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, an
    b) (1) determining, based at least in part on the presence of the LOH signature, that the patient has a relatively good prognosis, or b)(2) determining, based at least in part on the absence of the LOH signature, that the patient has a relatively poor prognosis 28. A composition comprising a therapeutic agent selected from the group consisting of DNA damaging agent, anthracycline, topoisomerase I inhibitor, and PARP inhibitor for use in treating a cancer selected from the group consisting of breast cancer, ovarian cancer, liver cancer, esophageal cancer, lung cancer, head and neck cancer, prostate cancer, colon cancer, rectal cancer, colorectal cancer, and pancreatic cancer in a patient with more than a reference number of LOH regions in at least one pair of human chromosomes of a cancer cell of the patient that are longer than a first length but shorter than the length of the whole chromosome containing the LOH region, wherein the at least one pair of human chromosomes is not a human X/Y sex chromosome pair, wherein the first length is about 1.5 or more megabases.

29. The composition of any of the preceding Paragraphs, wherein said LOH regions are determined in at least two, five, ten or 21 pairs of human chromosomes.

30. The composition of any of the preceding paragraphs, wherein the total number of said LOH regions is 9, 15, 20 or more.

31. The composition of any of the preceding paragraphs, wherein said first length is about 6, 12, or 15 or more megabases.

32. The composition of any of the preceding paragraphs, wherein said reference number is 6, 7, 8, 9, 10, 11, 12 or 13 or greater.

33. A method of treating cancer in a patient, comprising:
a) determining in a sample from said patient the number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases;
b) providing a test value derived from the number of said LOH regions;
c) comparing said test value to one or more reference values derived from the number of said LOH regions in a reference population (e.g., mean, median, terciles, quartiles, quintiles, etc.); and
d) administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or
e) recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value.

34. The method of Paragraph 33, wherein said LOH regions are determined in at least two, five, ten or 21 pairs of human chromosomes.

35. The method of Paragraph 33-34, wherein the total number of said LOH regions is 9, 15, 20 or more.

36. The method of Paragraph 33-35, wherein said first length is about 6, 12, or 15 or more megabases.

37. The method of Paragraph 33-36, wherein said reference number is 6, 7, 8, 9, 10, 11, 12 or 13 or greater.

38. The method of Paragraph 33-37, wherein said chemotherapy is selected from the group consisting of a DNA damaging agent, an anthracycline, and a topoisomerase I inhibitor and/or wherein said synthetic lethality agent is a PARP inhibitor drug.

39. The method of Paragraph 33-38, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, and/or said PARP inhibitor is iniparib, olaparib or velapirib.

40. A composition comprising a therapeutic agent selected from the group consisting of platinum comprising cancer therapy and anthracycline for use in treating a cancer selected from the group consisting of breast cancer, ovarian cancer, liver cancer, esophageal cancer, lung cancer, head and neck cancer, prostate cancer, colon cancer, rectal cancer, colorectal cancer, and pancreatic cancer in a patient with increased allelic imbalance.

41. The composition of paragraph 40, wherein the allelic imbalance is telomeric allelic imbalance.

42. The composition of paragraph 40-41, wherein the allelic imbalance is within about 25 kB of a copy number variation (CNV).

43. The composition of paragraph 40-42, wherein the patient is further determined not to carry a BRCA1 and/or BRCA2 mutation.

44. The composition of paragraph 40-43, wherein the patient is further determined to have decreased BRCA1 mRNA amount in the cancer cell and/or is further determined to have increased methylation of the BRCA1 promoter region.

45. A method for predicting the outcome of anti-cancer treatment of a subject with a cell hyperproliferative disorder, comprising determining a global chromosomal aberration score (GCAS), comprising obtaining a biological sample from the subject and determining whether a plurality of chromosomal regions displaying a chromosomal aberration exists within a plurality of chromosomal loci, wherein said chromosomal aberrations are selected from the group consisting of allelic imbalance (NAI), loss of heterozygosity (NLOH), copy number aberrations (NCNA), copy number gain (NCNG), copy number decrease (NCND) and combinations thereof, relative to a control, and wherein the presence of a plurality of chromosomal regions displaying said chromosomal aberrations predicts the outcome of anti-cancer treatment of the subject.

46. The method of paragraph 45, wherein the anti-cancer treatment is chemotherapy treatment.

47. The method of paragraph 45-46, wherein the chemotherapy treatment comprises platinum-based chemotherapeutic agents.

48. The method of paragraph 45-47, wherein the platinum-based chemotherapeutic agents are selected from the group consisting of cisplatin, carboplatin, oxaliplatin, nedaplatin, and iproplatin.

49. The method of paragraph 45-48, wherein the subject is a human.

50. The method of paragraph 45-49, wherein the cell hyperproliferative disorder is selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, colon cancer, melanoma, and vagina.

51. The method of paragraph 45-50, wherein the biological sample is selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow.

52. The method of paragraph 45-51, wherein the biological sample is enriched for the presence of hyperproliferative cells to at least 75% of the total population of cells.

53. The method of paragraph 45-52, wherein the enrichment is performed according to at least one technique selected from the group consisting of needle microdissection, laser microdissection, fluorescence activated cell sorting, and immunological cell sorting.

54. The method of paragraph 45-53, wherein an automated machine performs the at least one technique to thereby transform the biological sample into a purified form enriched for the presence of hyperproliferative cells.

55. The method of paragraph 45-54, wherein the biological sample is obtained before the subject has received adjuvant chemotherapy.

56. The method of paragraph 45-55, wherein the biological sample is obtained after the subject has received adjuvant chemotherapy.

57. The method of paragraph 45-56, wherein the control is determined from a non-cell hyperproliferative cell sample from the patient or member of the same species to which the patient belongs.

58. The method of paragraph 45-58, wherein the control is determined from the average frequency of genomic locus appearance of chromosomal regions of the same ethnic group within the species to which the patient belongs.

59. The method of paragraph 45-58, wherein the control is from non-cancerous tissue that is the same tissue type as said cancerous tissue of the subject.

60. The method of paragraph 45-59, wherein the control is from non-cancerous tissue that is not the same tissue type as said cancerous tissue of the subject.

61. The method of paragraph 45-60, wherein NAI is determined using major copy proportion (MCP).

62. The method of paragraph 45-61, wherein NAI for a given genomic region is counted when MCP is greater than 0.70.

63. The method of paragraph 45-62, wherein the plurality of chromosomal loci are randomly distributed throughout the genome at least every 100 Kb of DNA.

64. The method of paragraph 45-63, wherein the plurality of chromosomal loci comprise at least one chromosomal locus on each of the 23 human chromosome pairs.

65. The method of paragraph 45-64, wherein the plurality of chromosomal loci comprise at least one chromosomal locus on each arm of each of the 23 human chromosome pairs.

66. The method of paragraph 45-65, wherein the plurality of chromosomal loci comprise at least one chromosomal locus on at least one telomere of each of the 23 human chromosome pairs.

67. The method of paragraph 45-66, wherein the plurality of chromosomal loci comprise at least one chromosomal locus on each telomere of each of the 23 human chromosome pairs.

68. The method of paragraph 45-67, wherein the chromosomal aberrations have a minimum segment size of at least 1 Mb.

69. The method of paragraph 45-68, wherein the chromosomal aberrations have a minimum segment size of at least 12 Mb.

70. The method of paragraph 45-69, wherein the plurality of chromosomal aberrations comprises at least 5 chromosomal aberrations.

71. The method of paragraph 45-70, wherein the plurality of chromosomal aberrations comprises at least 13 chromosomal aberrations.

72. The method of paragraph 45-71, wherein the chromosomal loci are selected from the group consisting of single nucleotide polymorphisms (SNPs), restriction fragment length polymorphisms (RFLPs), and simple tandem repeats (STRs).

73. The method of paragraph 45-72, wherein the chromosomal loci are analyzed using at least one technique selected from the group consisting of molecular inversion probe (MIP), single nucleotide polymorphism (SNP) array, in situ hybridization, Southern blotting, transcriptional arrays, array comparative genomic hybridization (aCGH), and next-generation sequencing.

74. The method of paragraph 45-73, wherein outcome of treatment is measured by at least one criteria selected from the group consisting of survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

75. The method of paragraph 45-74, further comprising determining a suitable treatment regimen for the subject.

76. The method of paragraph 45-75, wherein said suitable treatment regimen comprises at least one platinum-based chemotherapeutic agent when a plurality of genomic chromosomal aberrations is determined or does not comprise at least one platinum-based chemotherapeutic agent when no plurality of genomic chromosomal aberrations is determined.

EXAMPLES

Example 1: Materials and Methods For Example 2

Pathologic response after neoadjuvant cisplatin therapy in the TNBC cohort was measured using the semi-quantitative Miller-Payne scale as described (Silver et al. (2010) *J. Clin. Oncol.* 28, 1145-1153; Ogston et al. (2003) *Breast* 12, 320-327). MIP genotyping was performed as described (Wang et al. (2007) *Genome Biol.* 8, R246). Allele signal intensity and genotypes from MIP genotyping or public SNP array analyses were processed by the CRLMM algorithm (Lin et al. (2008) *Genome Biol.* 9, R63) as implemented in the R package "oligo". DNA copy number was determined using the R package "AromaAffymetrix" (Bengtsson et al. (2008) *Bioinformatics* 24, 759-767). Processed genotype data was exported to dChip (available on the world wide web at http://biosunl.harvard.edu/complab/dchip/) for major copy proportion (MCP) determination, defined as ratio of major copy number to major+minor copy number (Li et al. (2008) *Bioinformatics* 9, 204). An estimate of level of normal DNA contamination was made from the genomic MCP curve as described (Li et al. (2008) *Bioinformatics* 9, 204). Breast or ovarian cases estimated to have 75% or more tumor content were included in analyses. Allelic imbalance (AI) for specific purposes of some Examples described herein was defined as MCP>0.7 and regions of AI defined as more than 10 consecutive probes with AI. Telomeric AI for specific purposes of some Examples described herein was defined as AI regions that extend to telomere and do not cross the centromere. Association between NtAI,12 and response to cisplatin in TNBC subjects was estimated by area under curve (AUC) of receiver operator characteristic (ROC) curve; p value is from two-sided Wilcoxon's rank test. Association between telomeric AI and time to recurrence of ovarian cancer after platinum therapy was estimated by Kaplan Meier analysis using a cutoff of 13 to define high NtAI,12 group; p value is based on log-rank test. A complete listing of materials and methods is as follows:

Cell Lines and Drug Sensitivity Assays

Figure 1A:
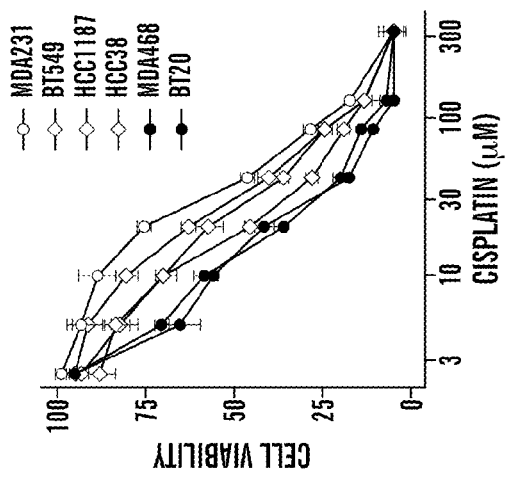
Figure 3A:
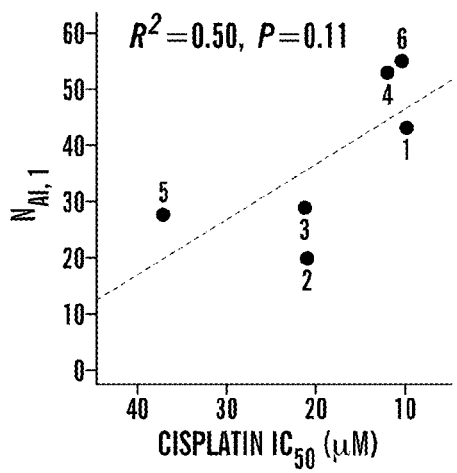
FIGS. 3A-3D show the association between cisplatin sensitivity and number of genomic abnormalities in a panel of TNBC cell lines.
Figure 3B:
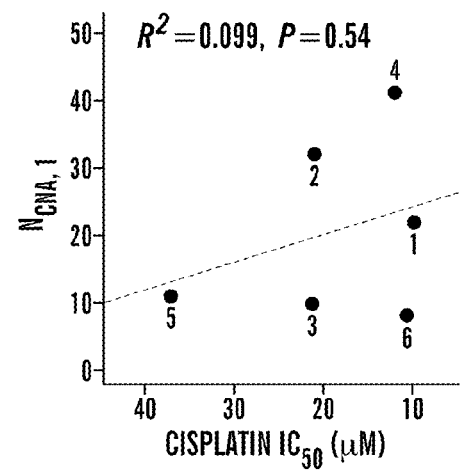
Figure 3C:
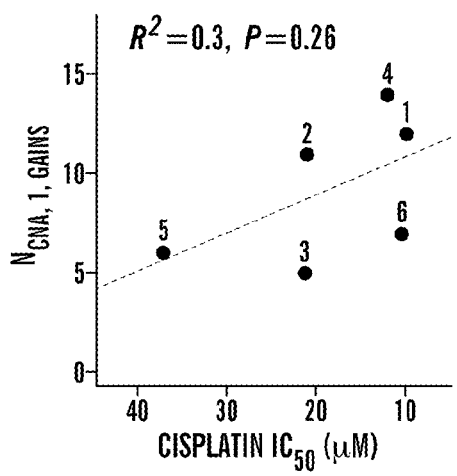
Figure 3D:
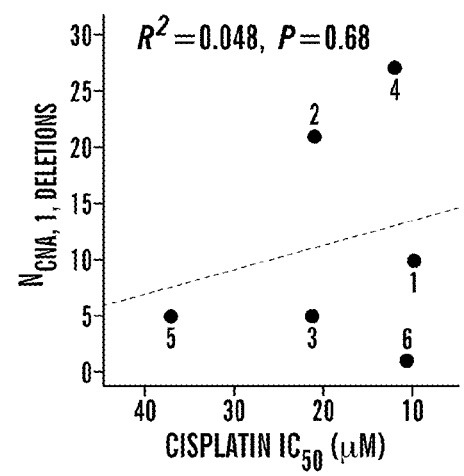

Tripe-negative breast cancer cell lines BT20, BT549, HCC1187, HCC38, MDA-MB231 and MDA-MB468 were maintained at 37° C. with 5% CO2 in RPMI 1640 medium and/or MEM medium supplemented with 10% FBS or other supplements as recommended by ATCC for each cell line. To test drug sensitivity, cells were exposed to a series of concentrations of cisplatin for 48 hours. Viable cell number was quantified using CellTiter 96 Aqueous One Solution Cell Proliferation Assay according to the manufacturer's instructions (Promega). The results are presented as the percentage of viable cells in drug-treated wells vs. media-treated control wells and plotted as a drug-does dependent cell survival curves (FIG. 1A). Drug sensitivity was quantified as the does of drug causing a 50% reduction of growth (IC50). This data was originally generated for a separate study in which it was reported as "data not shown" in Li et al. (2010) *Nat. Med.* 16, 214-218.

Breast Cancer Cohort

A total of 28 mainly sporadic TNBC patients were treated with cisplatin monotherapy in the neo-adjuvant setting (Silver et al. (2010) *J. Clin. Oncol.* 28, 1145-1153). Cisplatin response was measured using the semiquantitative Miller-Payne score by pathological assessment of surgical samples after therapy (Ogston et al. (2003) *Breast* 12, 320-327). Pathologic complete response is equivalent to Miller-Payne score and is defined as no residual invasive carcinoma in breast or lymph nodes.

Preparation of Breast Cancer Samples

A frozen core biopsy of the tumor was obtained before treatment started. Tumor tissue was available in the frozen core biopsy for 24 of 28 cases and in formalin fixed paraffin embedded diagnostic core biopsy samples from an additional 3 cases. Tumor cells were enriched by needle microdissection to remove stroma from hematoxylin and eosin (H & E) stained tissue sections. The remaining tissue on slides was examined by microscopy for estimation of enrichment. DNA was extracted from enriched tumor cells by proteinase K and RNase A digestions, phenol/chloroform extraction followed by ethanol precipitation. Adequate DNA for MIP genotyping analysis (minimum 80 ng) was obtained from all 27 cases for which tumor tissue was available. Paired normal DNA from each patient was obtained from peripheral blood lymphocytes.

Molecular Inversion Probe (MIP) Genotyping Analysis

DNA from breast tumor biopsy samples were sent to Affymetrix, Inc. (Santa Clara, Calif.) for MIP targeted genotyping analysis which generated allele signal intensity and genotypes for 42,000 individual single nucleotide polymorphisms (SNP). The complete MIP genotype data set is available on the NCBI GEO database.

Public Datasets

Affymetrix SNP 6.0 genomic profiles of six triple negative breast cancer cell lines, BT20, BT549, HCC1187, HCC38, MDA-MB231 and MDA-MB468, were acquired from the Welcome Trust Sanger Institute (information available on the world wide web at http://www.sanger.ac.uk/).

SNP data representing 118 ovarian carcinoma tumors arrayed on the Affymetrix 50K XbaI platform were acquired from the gene expression omnibus (GEO, GSE13813; Etemadmoghadam et al. (2009) *Clin. Cancer Res.* 15, 1417-1427). Of these, 38 tumors were of the serous subtype, had residual tumor after surgical debulking of less than 1 cm, and had received either adjuvant cisplatin or carboplatin treatment. Most patients (35 of 38) had also received taxane treatment.

Genotype and Copy Number Analysis

Allele signal intensity and genotypes from MIP genotyping or SNP array analyses were processed by the CRLMM algorithm (Lin et al. (2008) *Genome Biol.* 9, R63) as implemented in the R package "oligo". DNA copy number was determined using the R package "AromaAffymetrix" (Bengtsson et al. (2008) *Bioinformatics* 24, 759-767). Processed genotype data was exported to dChip (available on the world wide web at http://biosunl.harvard.edu/complab/dchip/) for major copy proportion (MCP) determination.

MCP is defined as the ratio of the major allele copy number to the major+minor allele copy number (Li et al. (2008) *Bioinformatics* 9, 204). The degree of normal cell contamination was estimated by the degree of shift in the MCP curve of the majority of regions showing allelic imbalance across genome, excluding all regions of copy number gain (The shift observed in the genomic MCP curves in paired normal and tumor cell line mixture experiments was used as reference to estimate normal contamination as described (Waddell et al. (2009) *Breast Cancer Res. Treat.* (December 4; e-published)). Accordingly, 21 of the 27 breast tumor samples and 33 of 38 of the ovarian cancer cases were estimated to have 25% or less of normal DNA contamination (75% tumor content) and were deemed acceptable for subsequent analysis.

Allelic imbalance (AI) was defined for purposes of some Examples described herein as MCP>0.70, which allows detection of the majority of loss of heterozygosity (LOH) events and of high-copy monoallelic amplifications in samples with 25% or less contamination or heterogeneity, but also excludes low-level copy gains (4-copy gains or less). Regions of AI were defined for purposes of some Examples described herein as more than 10 consecutive probes showing AI. In the TNBC dataset, the AI regions defined by these criteria included all callable LOH regions as determined from conventional genotype comparison. The total copy numbers (combining both alleles) were segmented by the circular binary segmentation algorithm. Eighty five percent of AI regions had total copy number near diploid or below, 9% of the AI regions showed total copy gain of 3, and 6% with total copy gain 4. Thus, the identified AI regions predominantly represent LOH or uniparental chromosomal deletion.

Association Between Number of Genomic Aberrations and Platinum Sensitivity In Vitro The numbers of regions of AI or regions with copy number aberration were compared to cell line-specific IC50 values after applying a 1 Mb minimum size filter to remove very small regions that could be caused by noise in the SNP 6.0 data (FIG. 3). For comparison of telomeric and interstitial AI regions, telomeric AI was defined for purposes of the Examples described herein as AI that extends to the telomere but does not cross the centromere. Conversely, interstitial AI was defined for purposes of the Examples described herein as AI regions that do not involve the telomere. To investigate if there was an optimum minimum size of telomeric AI or copy number alteration segments that showed a superior correlation to the cisplatin IC50, linear regression was used to compare the IC50 values with the total number of segments larger than a certain threshold, which was increased by 1 Mb intervals between 0 and 100 Mb (FIG. 5).

Association Between Number of Telomeric AI Regions and Platinum Sensitivity in Tumors Total number of regions of telomeric AI was determined for each TNBC case with at least 75% tumor content. The optimal minimum telomeric AI segment size threshold of 12 Mb found in the cell lines were applied, and NtA1,12 were counted for each subject. ROC (Receiver Operating Characteristic) curve analysis was performed to evaluate the capability of the total number of telomeric AI segments to predict pCR (Miller-Payne score 5) to cisplatin treatment.

The association of NtAI,12 with pCR to cisplatin was estimated by the area under the curve (AUC); the corresponding p-value is from two-sided Wilcoxon's rank test. Based on the ROC analysis, a NtAI.12 of 13 resulted in 100% sensitivity for prediction of pCR in the TNBC cisplatin treated cohort.

The association between NtA1,12 and time to recurrence after platinum-based therapy in the ovarian cancer cohort was estimated by Kaplan-Meier analysis with the "high NtA1,12" group defined as at least 13 regions of NtA1,12. P value is based on a log-rank test.

Example 2: Total Number of Chromosomal Rearrangements is Predictive of Chemotherapeutic Drug Sensitivity Without being bound by theory, it is believed that intrachromosomal loss of heterozycosity (LOH) or allelic imbalance (AI) results from improper repair of chromosomal DNA double-strand breaks and that the genome-wide count of these chromosomal rearrangements in a specific tumor may indicate the degree of DNA repair incompetence, independent of the specific causative DNA repair defect. Therefore, the total number of chromosomal rearrangements in a tumor reflects the inability to repair DNA damage induced by drugs like cisplatin, and consequently predicts sensitivity to these agents. Cisplatin sensitivity of six TNBC cell lines for which SNP array data was available from Wellcome Trust Sanger Institute, UK, was thus determined (FIG. 1A). AI was determined by major copy proportion (MCP) analysis, a method less sensitive to normal contamination in heterogeneous tumor samples (Li et al. (2008) *Bioinformatics* 9, 204).

The MCP is the number of major copy alleles at a locus divided by the sum of the number of major plus minor copy alleles (FIG. 2). Gains or reductions in total DNA copy number at each chromosomal region were inferred using dChip software (Lin et al. (2004) *Bioinformatics* 20, 1233-1240).

The DNA repair lesion(s) rendering cells sensitive to cisplatin may preferentially induce chromosomal alterations of a specific type or with a specific size range. In the six cell lines, the association between cisplatin sensitivity and each of four measures of chromosomal alterations was tested. The four measures were (1) the number of chromosome regions with AI (NAI), (2) the number of copy number aberrations (NCNA), (3) the number of regions with copy number gain, and (4) the number of regions with copy number decrease (FIG. 3). Of these four measures, the NAI was most strongly correlated with cisplatin sensitivity ($R2=0.5$).

Figure 4A:
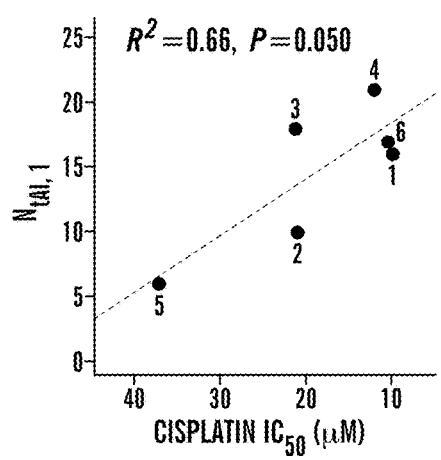
FIGS. 4A-4B show the association between cisplatin sensitivity and count of either telomeric or interstitial AI regions in a panel of TNBC cell lines.
Figure 4B:
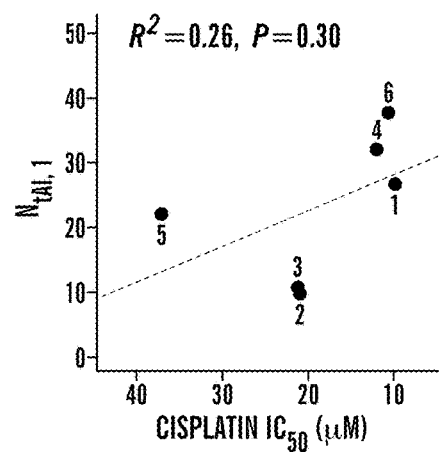

Known defects in DNA double strand break repair, including loss of BRCA1 or mutations in the Bloom helicase, cause the spontaneous formation of triradial and quadriradial chromosome structures, which are cytologic indications of aberrant recombination (Silver et al. (2007) *Cell* 128, 991-1002; Luo et al. (2000) *Nat. Genet.* 26, 424-429; Xu et al. (1999) *Mol. Cell* 3, 389-395). The resolution of these chromosome rearrangements at mitosis can result in loss of distal (telomeric) chromosome fragments and large regions of AI (Luo et al. (2000) *Nat. Genet.* 26, 424-429; Vrieling (2001) *Nat. Genet.* 28, 101-102). Thus, telomeric and interstitial (non-telomeric) AI regions were compared and it was found that the correlation between cisplatin sensitivity and AI was stronger when limited to AI regions involving telomeres, whereas only weak association was seen between cisplatin sensitivity and the number of interstitial AI regions (FIG. 4).

Next, it was determined if the correlations could be improved between cisplatin sensitivity and measures of genomic aberrations by testing a range of minimum segment sizes, in TNBC cell lines (FIG. 1B and FIGS. 5A-5C). Significant correlation with cisplatin sensitivity was seen using minimum telomeric AI segment size cutoffs between 5 and 25 Mb with the highest level of correlation seen for total number of segments with telomeric AI (NtAI) of at least 12 MB ($R2=0.8$; $P=0.016$; FIG. 1C). Testing for optimum minimum segment size did not appreciably improve the correlation between cisplatin sensitivity and measures of copy number aberrations, which remained not significant (FIGS. 5D-5F).

Whether the same association between NtAI and cisplatin sensitivity was present in clinical tumor samples using the optimum segment size cutoff of 12 MB (NtAI,12) was also investigated. NtAI,12 was compared to chemotherapy response in subjects with TNBC treated with preoperative cisplatin monotherapy (Silver et al. (2010) *J. Clin. Oncol.* 28, 1145-1153). Cryostat tissue sections of pre-treatment core biopsies were enriched for tumor cells by needle microdissection, and DNA was extracted for genotyping. Genotypes of 42,000 SNPs were determined with the Molecular Inversion Probe (MIP) targeted genotyping system (Affymetrix, Inc.) (Wang et al. (2007) *Genome Biol.* 8, R246). The degree of normal cell contamination was estimated from the MIP genotype data as described (Li et al. (2008) *Bioinformatics* 9, 204). No association was observed between the degree of normal contamination and response to cisplatin ($R2=0.004$, $P=0.75$).

Figure 6A:
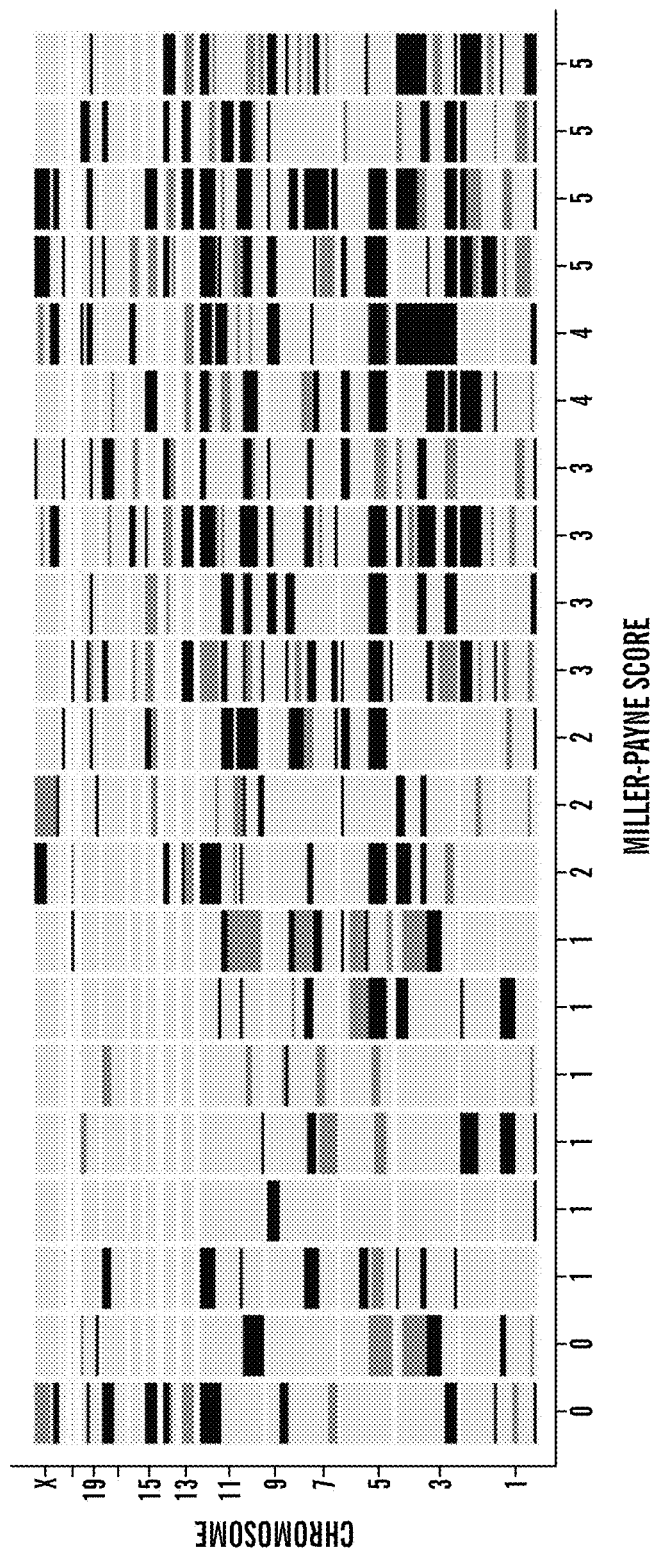
FIGS. 6A-6C show AI regions and cisplatin response in breast cancer. Pathologic response to cisplatin was assessed by the Miller-Payne (MP) score, which can range from 0 (progression) to 5 (pathologic complete response, pCR).
Figure 6C:
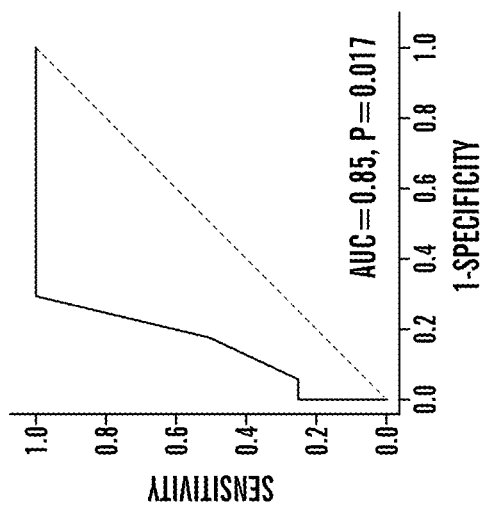
Figure 6B:
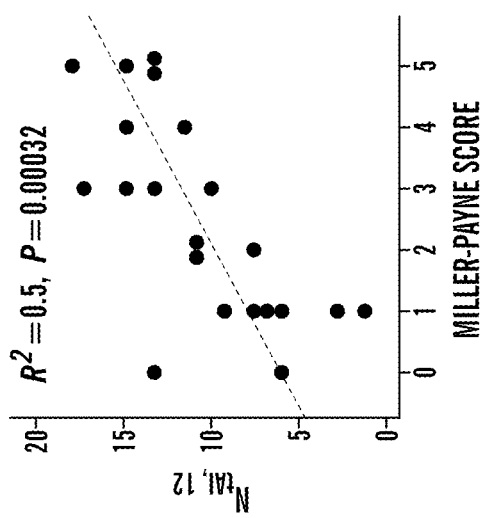
Figure 7:
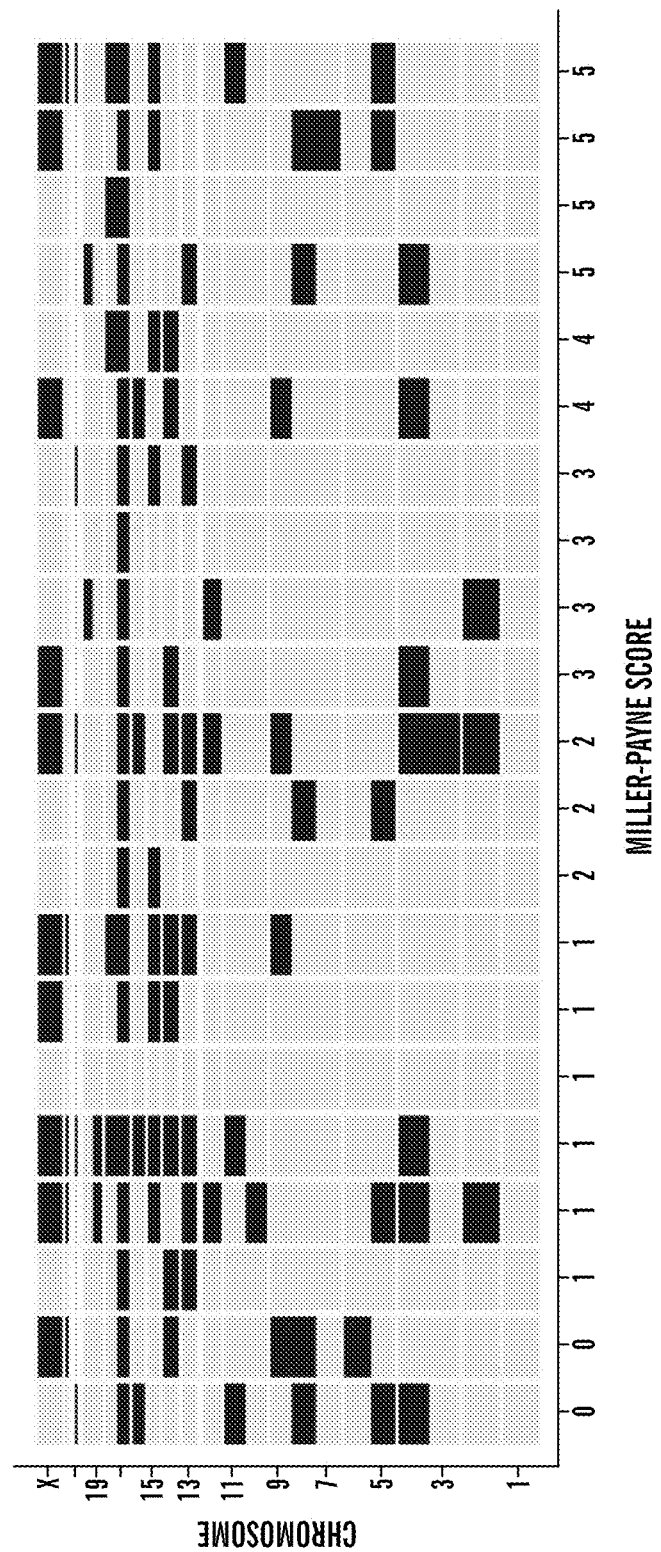
FIG. 7 shows whole chromosome allelic imbalance (isodisomy) and cisplatin sensitivity in breast cancers. Regions of whole chromosome AI are indicated in red for each chromosomal location. Each row defined by thin white lines represents a different chromosome and chromosome numbers are indicated along the left side. Each column represents an individual tumor sample. The Miller-Payne (MP) pathologic response score for each tumor is indicated along the bottom. Cases are arranged in order of increasing pathologic response to cisplatin (0=progression, 5=pathologic complete response (pCR)).

MIP genotype data from 21 cases with at least 75% tumor cell content were evaluated by MCP analysis to define the regions of telomeric, interstitial, or whole chromosome AI across the genome (FIG. 6A and FIG. 7). A correlation between the NtAI,12 and the response rate was observed, as quantified by the Miller-Payne score ($R2=0.5$; $P=0.00032$; FIG. 6B; Ogston et al. (2003) *Breast* 12, 320-327), with higher numbers of tAI regions associated with greater sensitivity to cisplatin. Receiver operating characteristic (ROC) curve analysis revealed that NtAI,12 was significantly associated with pathologic complete response to cisplatin (Miller-Payne 5) by the area under the curve ($AUC=0.85$; $P=0.017$; FIG. 6C). There was no apparent association between number of interstitial AI segments (FIG. 6A) or level of whole chromosome AI (FIG. 7) and response to cisplatin.

Figures 8A, 8B:
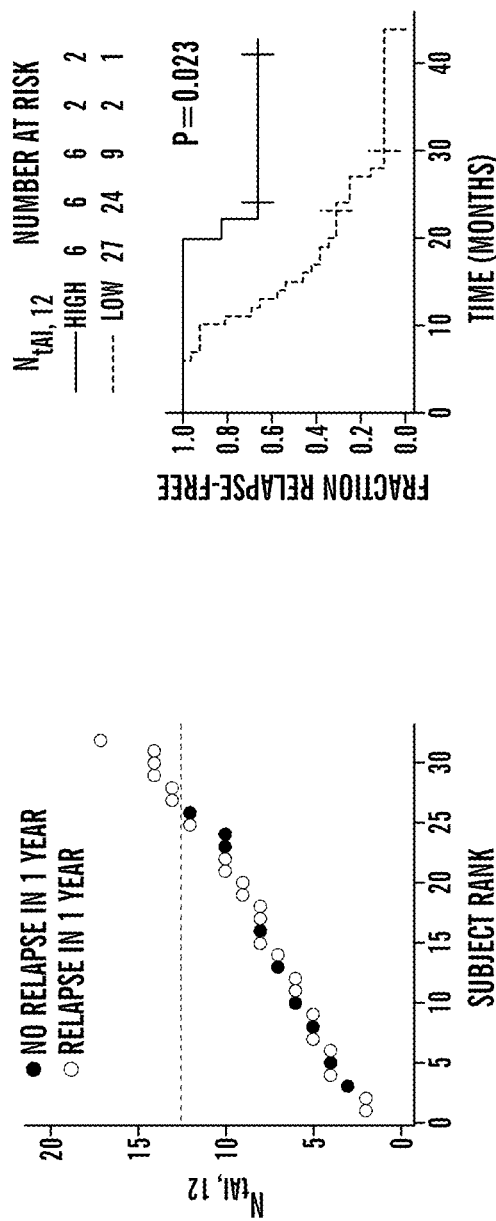
FIGS. 8A-8B show AI regions and time to relapse in serous ovarian cancer treated with platinum based therapy.

Serous ovarian carcinoma is often treated with platinum-based therapies. A publicly available SNP array data set of ovarian carcinomas treated with cisplatin or carboplatin plus a taxane (Etemadmoghadam et al. (2009) *Clin. Cancer Res.* 15, 1417-1427) was investigated and 33 cases of the serous subtype treated after optimal surgical debulking (residual tumor <1 cm) and reasonable tumor purity (>75%, estimated from SNP data) were identified. NtAI,12 was determined by MCP analysis. In these platinum-treated ovarian cancer cases, an association was found between higher levels of telomeric AI in tumors and absence of relapse within a year (FIG. 8A). The ROC analysis in the TNBC cohort was used to define a cutoff value of NtAI,12 of at least 13 events, which gave the greatest sensitivity for the classification of pCR to platinum therapy in the TNBC cohort. This cutoff was used to classify the ovarian cancer cohort into high and low NtAI,12 groups and longer disease-free survival, a surrogate indicator of higher sensitivity to platinum, was found in the high NtAI,12 group (FIG. 8B).

Figure 9:
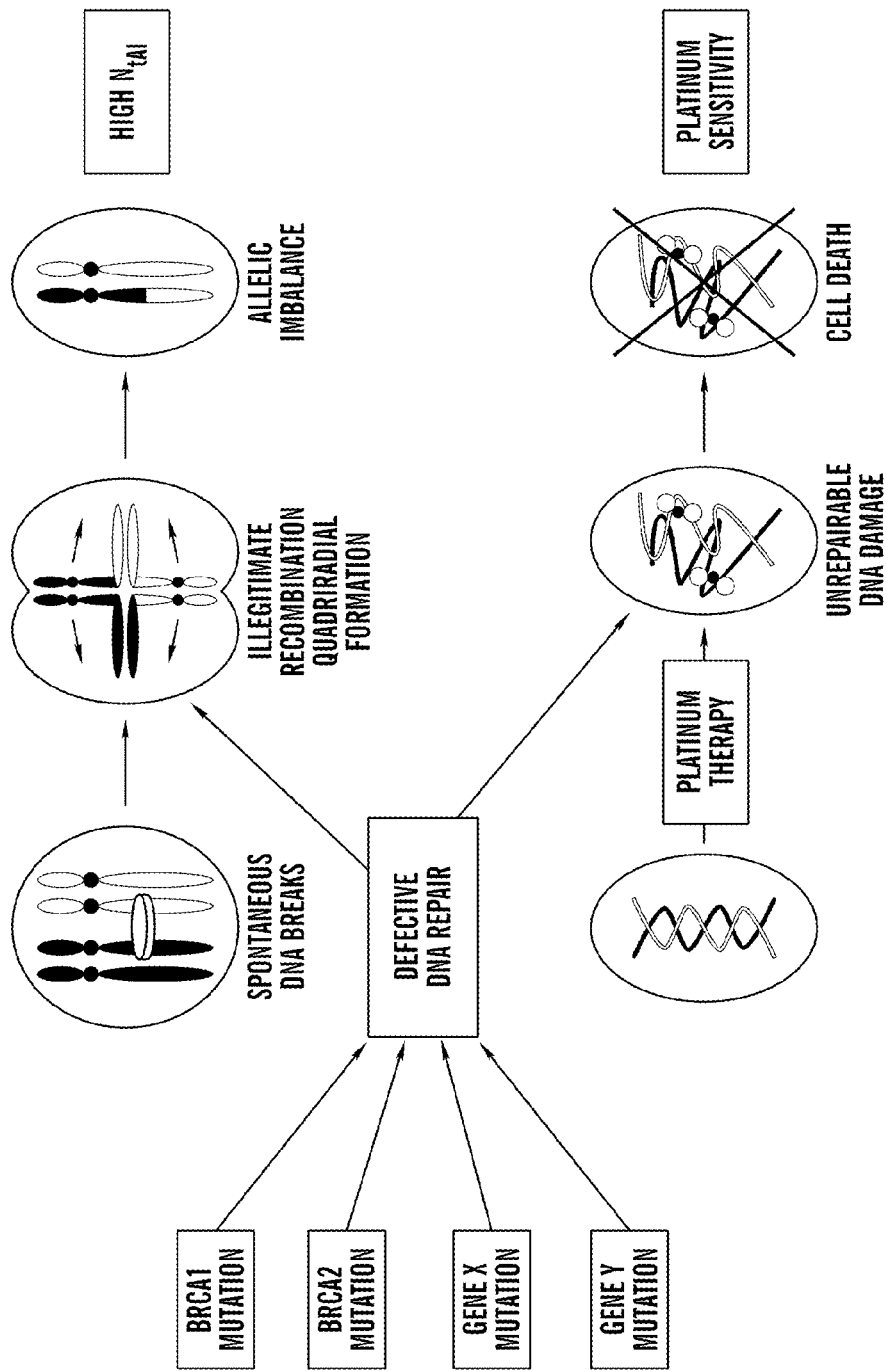
FIG. 9 shows a model relating DNA repair to accumulation of AI and response to platinum agents. Various genetic lesions can result in defects in common pathways of DNA repair, leading first to abnormal repair of spontaneous DNA breaks, then to illegitimate chromosome recombination and aberrant quadriradial chromosome formation, and finally to high levels of telomeric allelic imbalance. In parallel, the defective DNA repair pathway can also result in the inability of the tumor cell to repair drug-induced DNA damage, leading to tumor sensitivity to drugs such as platinum salts. Thus, the level of telomeric AI in a tumor serves as an indicator of defective DNA repair and predicts sensitivity to treatment with genotoxic agents.

Thus, chromosomal instability, manifested by high levels of telomeric AI, characterize subsets of TNBC and ovarian cancer, and further, higher levels of these changes predict specific therapeutic vulnerabilities. Although sporadic TNBC appear similar to BRCA1-associated breast cancer in the patterns of chromosomal alterations and various other immuno-phenotypes and histological features, the precise molecular defect(s) in maintenance of chromosomal stability in these tumors is unknown. The results of the examples described herein indicate that the burden of chromosome rearrangements resulting from improperly repaired DNA strand breaks are indicators of DNA repair defects that sensitize cells to certain chemotherapies (FIG. 9). As such, levels of allelic imbalance provide an accurate biomarker for predicting tumor sensitivity to treatment with genotoxic agents, irrespective of knowledge of the causative DNA repair lesion.

Example 3

In this study, we utilized two preoperative clinical trials in women with triple negative breast cancer treated with cisplatin, in which pathologic response at the time of surgery provided an experimental endpoint. Sporadic triple negative breast cancers are heterogeneous in their responses to platinum salts, chemotherapeutic agents that depend in part on DNA repair defects for their cytotoxic activity (Sakai, W., et al. Secondary mutations as a mechanism of cisplatin resistance in BRCA2-mutated cancers. Nature 2008; 451: 1116-1120; Edwards, S. L., et al. Resistance to therapy caused by intragenic deletion in BRCA2. Nature 2008; 451: 1111-1115). Lesions in DNA repair caused by BRCA1 or BRCA2 dysfunction lead to platinum sensitivity; we reasoned that the types of chromosomal aberrations arising in the context of BRCA dysfunction might also be associated with platinum sensitivity in wtBRCA (wild type BRCA) cancers. Based on results in cell lines, we chose to enumerate one such chromosomal abnormality, telomeric allelic imbalance (NtAI) in pre-treatment tumor genomes and to relate this to pathologic response after cisplatin, an exemplary platinum comprising therapy.

NtAI was associated with response to platinum treatment in our TNBC cisplatin trials and in platinum treated serous ovarian cancer and suggests the burden of this genomic abnormality exposes an underlying deficiency of DNA repair in the platinum-sensitive subset of these cancers. Allelic imbalance propagated from a given chromosomal location to the telomere suggests the operation of error-prone processes giving rise to abnormal crossover or template switching events, rather than error-free DNA repair.

We found the breakpoints of tAI regions are non-random and enriched for CNVs. This pattern also suggests defective DNA repair. CNVs are associated with other repeat sequences such as Alu repeats, are concentrated in pericentromeric and subtelomeric regions, and are associated also with common fragile sites (McVean, G. What drives recombination hotspots to repeat DNA in humans? Philos Trans R Soc Lond B Biol Sci 2010; 365: 1213-1218; Puliti, A., et al. Low-copy repeats on chromosome 22q11.2 show replication timing switches, DNA flexibility peaks and stress inducible asynchrony, sharing instability features with fragile sites. Mutat Res 2010; 686: 74-83). These repeat elements are thought to result in replication "slow zones" prone to replication stalling and formation of DNA double strand breaks (Richard, G. F., Kerrest, A., and Dujon, B. Comparative genomics and molecular dynamics of DNA repeats in eukaryotes. Microbiol Mol Biol Rev 2008; 72: 686-727; Cha, R. S. and Kleckner, N. ATR homolog Mec1 promotes fork progression, thus averting breaks in replication slow zones. Science 2002; 297: 602-606). Furthermore, downregulation of Rad51 or inhibition of BRCA1 increases the fragility at such sites when cells are under replication stress (Arlt, M. F., et al., BRCA1 is required for common-fragile-site stability via its G2/M checkpoint function. Mol Cell Biol 2004; 24: 6701-6709; Schwartz, M., et al. Homologous recombination and nonhomologous end-joining repair pathways regulate fragile site stability. Genes Dev 2005; 19: 2715-2726). The observed association of low BRCA1 expression levels in many tumors with high NtAI suggests deficient homologous recombination, impaired S or G2/M checkpoint function, or a combination of these factors underlies the generation of this type of genomic abnormality.

Cisplatin forms inter-strand crosslinks on DNA that lead to stalled replication forks and DNA double stand breaks that must be repaired if the cell is to survive. It is likely these breaks are repaired using similar mechanisms to those employed at stalled replication forks and DNA breaks generated at sites of CNVs. Therefore, high pre-treatment NtAI identifies tumors unable to accurately repair breaks and restart stalled replication forks at sites of CNV. These same tumors are also unable to contend with stalled forks at sites of cisplatin crosslinks.

While allelic imbalance at sites of CNV may reflect inefficient error-free repair, other explanations should be considered. Both triple negative cohorts showed a significant relationship between NtAI and pathologic response to cisplatin chemotherapy. Nevertheless, there were patients in both trials whose tumors showed poor response to cisplatin therapy despite having high NtAI. Similarly, a few of the BRCA1-mutated ovarian cancers had high NtAI yet were resistant to platinum therapy. Since NtAI is a summation of ongoing and past DNA lesions, resistance mechanisms acquired after generation of tAI would confound the relationship between NtAI and response. In carriers of BRCA1 or BRCA2 mutations, some tumors that become resistant to platinum agents carry a reversion mutation that partially or completely restores BRCA1 or BRCA2 function and restores homologous recombination (Sakai, W., et al. Secondary mutations as a mechanism of cisplatin resistance in BRCA2-mutated cancers. Nature 2008; 451: 1116-1120; Edwards, et al. Resistance to therapy caused by intragenic deletion in BRCA2. Nature 2008; 451: 1111-1115; Swisher, E. M., et al., Secondary BRCA1 mutations in BRCA1-mutated ovarian carcinomas with platinum resistance. Cancer Res 2008; 68: 2581-2586). Reversion has also been seen in a cell line with a BRCA2 mutation selected for PARP inhibitor resistance (Edwards, et al. Resistance to therapy caused by intragenic deletion in BRCA2. Nature 2008; 451: 1111-1115). Reversion mutations and in cis compensating mutations were observed in Fanconi anemia patients, resulting in improvement in their bone marrow function (Kalb, R., et al., Fanconi anemia: causes and consequences of genetic instability. Genome Dyn 2006; 1:218-242). Inactivation of TP53BP1 restores the balance between homologous recombination and non-homologous end joining in BRCA1-mutated cells and renders them resistant to PARP inhibitors (Bouwman, P., et al. 53BP1 loss rescues BRCA1 deficiency and is associated with triple-negative and BRCA-mutated breast cancers. Nat Struct Mol Biol 2010; 17: 688-695; Bunting, S. F., et al. 53BP1 inhibits homologous recombination in Brca1-deficient cells by blocking resection of DNA breaks. Cell 2010; 141: 243-254). Finally, drug transporters may prevent accumulation of platinum agents in tumor cells (Burger, H., et al., Drug transporters of platinum-based anticancer agents and their clinical significance. Drug Resist Updat 2011). Therefore, reversion of or compensation for a preexisting DNA repair defect may generate a tumor with high NtAI but resistance to platinum treatment; other platinum resistance mechanisms unrelated to DNA repair would have the same effect.

Our analysis suggests an outline of the molecular taxonomy of TNBC and ovarian cancer with respect to DNA repair and drug sensitivity. Most platinum resistant breast or ovarian cancers are tumors with repair proficiency and low NtAI. Two subsets of wtBRCA tumors possess high NtAI and are sensitive to platinum-containing drugs. In one of these subsets, repair deficiency may be the consequence of low BRCA1 expression and in the other subset, repair may be crippled by mechanisms that do not depend upon BRCA1 expression. These observations will no doubt be further refined; inclusion of reversion mutations, compensations by other events in DNA repair pathways, other mechanisms of drug resistance, and other as yet unappreciated factors may help to enhance our prediction of drug sensitivity in the future.

In conclusion, a summary measure of telomeric chromosome aberrations in the tumor genome, NtAI, predicts sensitivity to platinum treatment. Our findings implicate NtAI as a marker of impaired DNA double-strand break repair. Assays to determine NtAI are feasible using formalin fixed paraffin embedded tumor material and recent algorithms such as ASCAT permit accurate determination of copy number and allelic imbalance in a majority of samples despite low tumor cell content. NtAI may prove useful in predicting response to a variety of therapeutic strategies exploiting defective DNA repair.

Materials and Methods

Cell lines and drug sensitivity assays: Drug sensitivity measurements in breast cancer cell lines BT20, BT549, HCC1187, HCC1143, MDA-MB-231, MDA-MB-468, HCC38, MDA-MB-453 (triple negative), CAMA-1, MCF7, T47D (ER positive), BT474, HCC1954 and MDA-MB-361 (HER2positive) was originally generated for a separate study in which it was reported as "data not shown" in a recently published manuscript (Li, Y., et al. Amplification of LAPTM4B and YWHAZ contributes to chemotherapy resistance and recurrence of breast cancer. Nat Med 2010; 16: 214-218). Briefly, cells were exposed to a series of concentrations of various chemotherapeutic agents for 48 hours. Viable cell number was quantified using CellTiter 96 AQueous One Solution Cell Proliferation Assay according to the manufacturer's instructions (Promega). Drug sensitivity was quantified as the dose of drug resulting in a 50% reduction of growth (IC50). We found MCF7 to be highly resistant to all of the chemotherapeutic agents tested, consistent with its reported caspase-3 deficiency and resistance to drug induced apoptosis (Yang, X. H., et al., Reconstitution of caspase 3 sensitizes MCF-7 breast cancer cells to doxorubicin- and etoposide-induced apoptosis. Cancer Res 2001; 61: 348-354). In our analyses with measures of genomic aberration, MCF7 was the only clear outlier and for these reasons, was excluded from our analyses.

Breast Cancer Cohorts and Assessment of Therapeutic Response

For this study, subjects were included for analysis of response to cisplatin if they progressed on therapy or if they received at least 3 of 4 cycles of the planned cisplatin therapy, had received no other non-protocol therapy before surgery, and if an adequate amount of tumor was available from the pre-treatment biopsy. Therapeutic response was measured using the semiquantitative Miller-Payne grading system, which estimates the percent reduction in invasive tumor volume and cellularity based on pathological assessment of surgical samples after therapy (Ogston, K. N., et al., A new histological grading system to assess response of breastcancers to primary chemotherapy: prognostic significance and survival. Breast 2003; 12: 320-327). Cisplatin-1 consists of 28 mainly sporadic TNBC patients treated with preoperative cisplatin monotherapy, of whom 4 progressed on therapy and 24 completed 4 cycles of cisplatin therapy (Silver, D. P., et al. Efficacy of neoadjuvant Cisplatin in triple-negative breast cancer. J Clin Oncol 2010; 28: 1145-1153). Cisplatin-2 consists of 51 TNBC patients treated with preoperative cisplatin and bevacizumab, of which one patient progressed on therapy and 44 patients completed 4 cycles of cisplatin therapy prior to surgery (Ryan, P. D., et al. Neoadjuvant cisplatin and bevacizumab in triple negative breast cancer (TNBC): Safety and Efficacy. J Clin Oncol 2009; 27: 551). Two patients included in this study were taken to surgery after completing 3 cycles of cisplatin therapy due to the development of toxicity; in both cases there was no appreciable pathologic response in the excised tumor after 3 cycles of cisplatin.

Preparation of Breast Cancer Samples

For both trials, core biopsies of tumor were obtained before initiation of treatment. Adequate tumor for analysis was present for 27 of 28 subjects in Cisplatin-1 and 37 of 51 subjects in Cisplatin-2. H&E stained tissue sections of pre-treatment core needle biopsies were examined microscopically; for all biopsies for which enrichment was deemed feasible, sections were manually microdissected using an 18-gauge needle. DNA was extracted by proteinase K and RNase A digestions, phenol/chloroform extraction, and ethanol precipitation. Paired normal DNA from patients was obtained from peripheral blood lymphocytes for all cases in Cisplatin-1 and from 10 cases in Cisplatin-2.

TCGA Ovarian and Breast Cancer Cohorts

Public SNP array data, expression data, and clinical annotation data was obtained for the TCGA ovarian (Bell, D., et al., Integrated genomic analyses of ovarian carcinoma. Nature 2011; 474: 609-615) and breast cancer cohorts from the TCGA web site (http://tcga-data.nci.nih.gov/tcga/). BRCA1 and BRCA2 mutation status for the ovarian cancers was obtained from cBIO data portal (http://bit.ly/wpwRXd). In the ovarian cohort, we identified 218 samples with SNP data that passed ASCAT, BRCA mutation status, and interpretable clinical annotations for treatment and outcomes indicating initial treatment with adjuvant platinum-based chemotherapy, predominantly the combination of carboplatin and docetaxel. We classified "treatment sensitive" as those annotated as partial or complete response to initial treatment and no progression or recurrence within 6 months of initial treatment (n=187); "treatment resistant" were those annotated as stable or progressive disease on initial therapy or disease recurrence or progression within 6 months (n=31). In the breast cohort, we identified 78 samples with matched gene expression and SNP data that passed ASCAT, which were classified as ER-/HER2-based on clustering of the ESR1 and ERBB2 gene (see supplementary methods).

Genotyping and Copy Number Analysis

DNA was sent to Affymetrix, Inc. (Santa Clara, Calif.) for determination of genotypes using the molecular inversion probe based genotyping system, OncoScan FFPE Express (Wang, Y., et al. Analysis of molecular inversion probe performance for allele copy number determination. Genome Biol 2007; 8: R246). The commercial assay, which determines genotype of 330,000 SNPs was used for analysis of the Cisplatin-2 trial. An early version of the OncoScan assay which genotypes 42,000 SNPs was used for the Cisplatin-1 trial. Allele signal intensity and genotypes from the OncoScan genotyping assay were processed and provided to us by Affymetrix. The OncoScan SNP genotype data for the cisplatin therapy trials is submitted to the NCBI GEO database under accession GSE28330. Public SNP array raw data for the breast cancer cell lines were obtained from the Sanger Institute Catalogue Of Somatic Mutations In Cancer web site, world wide web "dot" sanger "dot" ac "dot" uk/cosmic (Bamford, S., et al. The COSMIC (Catalogue of Somatic Mutations in Cancer) database and website. Br J Cancer 2004; 91: 355-358), public SNP array data from an independent breast cancer cell line study, Heiser et al. (Heiser, L. M., et al. Subtype and pathway specific responses to anticancer compounds in breast cancer. Proc Natl Acad Sci USA 2011), and public SNP array data from the TCGA ovarian (Bell, D., et al., Integrated genomic analyses of ovarian carcinoma. Nature 2011; 474: 609-615) and breast cancer cohorts were preprocessed by the AROMAv2 and CalMaTe algorithms (Bengtsson, H., Wirapati, P., and Speed, T. P. A single-array preprocessing method for estimating full-resolution raw copy numbers from all Affymetrix genotyping arrays including GenomeWideSNP 5 & 6. Bioinformatics 2009; 25:2149-2156) and, when a paired normal samples was available, TumorBoost (Bengtsson, H., Neuvial, P., and Speed, T. P. TumorBoost: normalization of allele-specific tumor copy numbers from a single pair of tumor-normal genotyping microarrays. BMC Bioinformatics 2010; 11:245). Processed genotype data from OncoScan genotyping and public SNP array data was analyzed for allele-specific copy numbers and tumor cell content by the algorithm "Allele-specific copy number analysis of tumors", ASCAT (Van Loo, P., et al. Allele-specific copy number analysis of tumors. Proc Natl Acad Sci USA 2010; 107: 16910-16915). ASCAT is designed to correct for normal cell contamination and tumor cell ploidy, but occasionally fails to fit a model to a given sample. In this study, ASCAT failed to process 3 of 14 cell lines from Sanger, 15 of 42 cell lines from Heiser et al., and 5 of 37 samples from the Cisplatin-2 trial. Allelic imbalance was defined as any time the copy number of the two alleles were not equal, and at least one allele was present (FIG. 16). To ensure that all trial cases were comparable, we eliminated cases estimated by ASCAT to have less than 36% tumor cell content, the highest level of normal cell admixture in the Cisplatin-1 trial, which was the trial with an overall greater tumor purity. Thus we included all 27 samples with SNP array data from the Cisplatin-1 trial, 26 out of 32 samples with SNP array data that passed ASCAT from the Cisplatin-2 trial.

A minimum number of consecutive probes showing an aberration was required in order to call regions of AI and CNA with confidence. To ensure similar aberration detection across the three platforms that were used, the minimum number of probes required to define a region of aberration was set to be proportional to the overall SNP density of the platform. The probe densities of the platforms were 42,000/genome OncoScan (prototype), 330,000/genome OncoScan FFPE Express, and 900,000/genome SNP6.0 for an approximate ratio of 1:8:20. Minimum probe requirements of 25 probes for 42k OncoScan prototype, 200 probes for 330k OncoScan FFPE Express, and 500 probes for SNP6.0 platform were chosen based on optimizing for correlation of aberration measurement in a subset of samples with replicate data generated on both versions of the OncoScan platform (See also Supplementary Methods).

Telomeric AI and telomeric CNA are defined as regions that extend to one of the sub-telomeres but do not cross the centromere. Copy number of telomeric AI regions was defined as the mean copy number of the probes mapping to the region. Copy loss was defined as a mean of less than 1.5 copies and copy gain was defined as a mean of greater than 2.5 copies. Association between NtAI and response to cisplatin in the TNBC clinical trials was measured by the AUC of the ROC curve for binary response. Statistical significance was assessed by Wilcoxon's rank sum test. All P values are two-sided.

Enrichment of Copy Number Variants at Site of DNA Breakpoints

The genomic location of common copy number variants (CNVs) was acquired from the Database of Genomic Variants (http://projects.tcag.ca/variation/). Mapping for HG17 and HG18 was acquired in order to match the SNP probe mapping of the 42K prototype and 330K commercial OncoScan platforms, respectively. CNVs were considered associated with a breakpoint if they overlapped within a 25 kb window on either side of the breakpoint. To test for enrichment, we performed 1000 permutations for each cohort, where we randomly shuffled the location of the DNA breakpoints based on the location of the SNP probes, and determined how many were associated with CNVs.

BRCA1 Transcript Quantitation and Promoter Methylation Analysis

BRCA1 exon 16/17 and RPLPO (control) quantitative polymerase chain reaction assay was performed as previously described (Silver, D. P., et al. Efficacy of neoadjuvant Cisplatin in triple-negative breast cancer. J Clin Oncol 2010; 28:1145-1153) using amplified tumor cDNA generated using Ovation RNA Amplification System V2 kit (NuGen Technologies, Inc., San Carlos, Calif.). BRCA1 promoter methylation assay was performed as previously described (Silver, D. P., et al. Efficacy of neoadjuvant Cisplatin in triple-negative breast cancer. J Clin Oncol 2010; 28:1145-1153).

BRCA1 Expression in Public TCGA Cohorts.

Public normalized and summarized Agilent based gene expression data was acquired from the TCGA for all breast cancer samples (level 3). Raw Affymetrix CEL files were obtained for ovarian cancer samples (level 1). Expression data for all TCGA ovarian cancer samples were normalized and summarized using RMA, and the probe set "204531_s_at" was identified as the optimum probe set for measuring BRCA1 expression using the R package "JetSet" (Li, Q., et al., Jetset: selecting the optimal microarray probe set to represent a gene. BMC Bioinformatics 2011; 12:474).

INCORPORATION BY REFERENCE

All publications, patents, and patent applications mentioned in the specification, including the examples, are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following paragraphs.

What is claimed is:

1. A method of administering an anti-cancer treatment to a human patient, comprising:
   (a) detecting in a sample from a human patient, a plurality of chromosomal aberrations in chromosomal segments comprising a plurality of loci,
   wherein chromosomal aberrations are detected in at least one pair of human chromosomes of a cancer cell of the patient,
   wherein each of the chromosomal aberrations is at least 12 Mb in length, extends to and involves the telomere but does not cross the centromere, and
   (b) calculating a telomeric imbalance score (NtAI) by summing the number of chromosomal aberrations detected in step (a);
   (c) detecting an NtAI of at least 8; and
   (d) administering to said patient an anti-cancer therapy selected from the group consisting of: platinum-comprising therapy, DNA damaging agent-comprising therapy, anthracycline-comprising therapy, topoisomerase I inhibitor-comprising therapy and PARP inhibitor-comprising therapy.

2. The method of claim 1, wherein said detecting a plurality of chromosomal aberrations is in at least two, five, ten or 21 pairs of human chromosomes.

3. The method of claim 1, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, and/or said PARP inhibitor is iniparib, olaparib or velapirib.

4. The method of claim 1, wherein the cancer is selected from the group consisting of breast cancer, ovarian cancer, melanoma, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, colon cancer, or vagina.

5. The method of claim 1, wherein the number of chromosomal segments comprising a plurality of chromosomal aberrations is determined using major copy proportion (MCP).

6. The method of claim 5, wherein the number of chromosomal segments comprising a plurality of chromosomal aberrations for a given genomic region is counted when MCP is greater than 0.70.

7. The method of claim 1, wherein the NtAI score is at least 20.

* * * * *